US008063760B2

(12) United States Patent  
Volpi et al.

(10) Patent No.: US 8,063,760 B2
(45) Date of Patent: Nov. 22, 2011

(54) INTERROGATOR AND INTERROGATION SYSTEM EMPLOYING THE SAME

(75) Inventors: John P. Volpi, Garland, TX (US); Jimmy D. Laferney, Frisco, TX (US); David W. Hensley, Dallas, TX (US); Robert C. Hatch, Arroyo Grande, CA (US); Glenn W. Boisbrun, Richardson, TX (US)

(73) Assignee: Veroscan, Inc., Plano, TX (US)

( * ) Notice: Subject to any disclaimer, the term of this patent is extended or adjusted under 35 U.S.C. 154(b) by 978 days.

(21) Appl. No.: 11/838,077

(22) Filed: Aug. 13, 2007

(65) Prior Publication Data

US 2008/0018450 A1    Jan. 24, 2008

Related U.S. Application Data

(63) Continuation-in-part of application No. 11/357,225, filed on Feb. 17, 2006, now Pat. No. 7,760,097, which is a continuation of application No. 10/378,043, filed on Mar. 3, 2003, now Pat. No. 7,019,650, and a continuation-in-part of application No. 11/071,652, filed on Mar. 3, 2005.

(60) Provisional application No. 60/836,997, filed on Aug. 11, 2006.

(51) Int. Cl.
*G08B 26/00* (2006.01)
(52) U.S. Cl. .................. 340/505; 340/572.1; 340/573.1; 340/539.1; 340/539.11; 340/539.13
(58) Field of Classification Search ............. 340/825.36, 340/825.49, 572.1, 573.1, 539.1, 537.11, 340/539.13
See application file for complete search history.

(56) References Cited

U.S. PATENT DOCUMENTS

| 3,367,431 A | 2/1968 | Pollock et al. |
| 3,564,662 A | 2/1971 | Fabian et al. |
| 3,675,190 A | 7/1972 | Auer, Jr. et al. |
| 3,802,555 A | 4/1974 | Grasty et al. |
| 3,941,132 A | 3/1976 | Lenaghan |
| 3,965,907 A | 6/1976 | Hardy et al. |

(Continued)

FOREIGN PATENT DOCUMENTS

DE    199 23 983 A1    12/2000

(Continued)

OTHER PUBLICATIONS

U.S. Appl. No. 10/841,192, filed May 7, 2004, Roemerman, et al.

(Continued)

*Primary Examiner* — Daryl Pope
(74) *Attorney, Agent, or Firm* — Slater & Matsil, L.L.P.

(57) ABSTRACT

An interrogator, methods of discerning the presence of an object, and interrogation systems employing the same. In one embodiment, the interrogation systems include multiple interrogators that communicate with a base command unit to track a location of an object. In another embodiment wherein the object is an RFID object (e.g., an object with an RFID tag), the interrogators employ signal processing techniques such as precharging the RFID object, and correlating a reference code with a reply code from the RFID object using selected techniques to increase a sensitivity of the interrogator, especially for adverse environments. In other embodiments, the interrogation systems include variations of metal instruments and sponges employed therewith. In yet another embodiment, the interrogation system includes metal interrogators capable of discerning the presence of a metal object, especially in a presence of another metal object.

20 Claims, 49 Drawing Sheets

U.S. PATENT DOCUMENTS

| | | | |
|---|---|---|---|
| 4,114,601 A | 9/1978 | Abels |
| 4,151,913 A | 5/1979 | Freitag |
| 4,164,320 A | 8/1979 | Irazoqui et al. |
| 4,193,405 A | 3/1980 | Abels |
| 4,213,197 A | 7/1980 | Mágori |
| 4,249,128 A | 2/1981 | Karbowski |
| 4,289,032 A | 9/1981 | Tominaga et al. |
| 4,295,537 A | 10/1981 | McAvinn et al. |
| 4,342,391 A | 8/1982 | Schainholz |
| 4,359,015 A | 11/1982 | Ritchey |
| 4,361,231 A | 11/1982 | Patience |
| 4,422,548 A | 12/1983 | Cheesman et al. |
| 4,422,584 A | 12/1983 | Dashnier et al. |
| 4,498,076 A | 2/1985 | Lichtblau |
| 4,510,489 A | 4/1985 | Anderson, III et al. |
| 4,514,692 A | 4/1985 | Johnson et al. |
| 4,526,177 A | 7/1985 | Rudy et al. |
| 4,541,992 A | 9/1985 | Jerge et al. |
| 4,643,303 A | 2/1987 | Arp et al. |
| 4,650,464 A | 3/1987 | Ruiz et al. |
| 4,658,818 A | 4/1987 | Miller, Jr. et al. |
| 4,821,023 A | 4/1989 | Parks |
| 4,832,198 A | 5/1989 | Alikhan |
| 4,855,909 A | 8/1989 | Vincent et al. |
| 4,857,713 A | 8/1989 | Brown |
| 4,887,715 A | 12/1989 | Spahn et al. |
| 4,889,230 A | 12/1989 | Zachry |
| 4,903,837 A | 2/1990 | Duello |
| 4,907,000 A | 3/1990 | Tabourier |
| 4,922,922 A | 5/1990 | Pollock et al. |
| 4,943,939 A | 7/1990 | Hoover |
| 5,009,275 A | 4/1991 | Sheehan |
| 5,031,642 A | 7/1991 | Nosek |
| 5,057,095 A | 10/1991 | Fabian |
| 5,103,210 A | 4/1992 | Rode et al. |
| 5,105,829 A | 4/1992 | Fabian et al. |
| 5,107,862 A | 4/1992 | Fabian et al. |
| 5,186,322 A | 2/1993 | Harreld et al. |
| 5,188,126 A | 2/1993 | Fabian et al. |
| 5,190,059 A | 3/1993 | Fabian et al. |
| 5,231,273 A | 7/1993 | Caswell et al. |
| 5,241,568 A | 8/1993 | Fernandez et al. |
| 5,284,632 A | 2/1994 | Kudla et al. |
| 5,300,120 A | 4/1994 | Knapp et al. |
| 5,329,944 A | 7/1994 | Fabian et al. |
| 5,353,011 A | 10/1994 | Wheeler et al. |
| 5,354,975 A | 10/1994 | Ishibashi et al. |
| 5,357,240 A | 10/1994 | Sanford et al. |
| 5,374,261 A | 12/1994 | Yoon |
| 5,381,137 A | 1/1995 | Ghaem et al. |
| 5,382,784 A | 1/1995 | Eberhardt |
| 5,414,730 A | 5/1995 | Lundquist et al. |
| 5,433,929 A | 7/1995 | Riihimaki et al. |
| 5,443,082 A | 8/1995 | Mewburn |
| 5,451,380 A | 9/1995 | Zinnanti |
| 5,456,718 A | 10/1995 | Szymaitis |
| 5,460,178 A | 10/1995 | Hudon et al. |
| 5,491,468 A | 2/1996 | Everett et al. |
| 5,528,232 A | 6/1996 | Verma et al. |
| 5,594,384 A | 1/1997 | Carroll et al. |
| 5,610,811 A | 3/1997 | Honda |
| 5,629,498 A | 5/1997 | Pollock et al. |
| 5,650,596 A | 7/1997 | Morris et al. |
| 5,689,239 A | 11/1997 | Turner et al. |
| 5,781,442 A | 7/1998 | Engleson et al. |
| 5,792,138 A | 8/1998 | Shipp |
| 5,793,324 A | 8/1998 | Aslanidis et al. |
| 5,801,371 A | 9/1998 | Kahn et al. |
| 5,827,215 A | 10/1998 | Yoon |
| 5,864,323 A | 1/1999 | Berthon |
| 5,923,001 A | 7/1999 | Morris et al. |
| 5,931,824 A | 8/1999 | Stewart et al. |
| 5,979,941 A | 11/1999 | Mosher, Jr. et al. |
| 5,986,550 A | 11/1999 | Rapaport et al. |
| 6,026,818 A | 2/2000 | Blair et al. |
| 6,037,870 A | 3/2000 | Alessandro |
| 6,097,374 A | 8/2000 | Howard |
| 6,150,921 A | 11/2000 | Werb et al. |
| D435,557 S | 12/2000 | Eisenberg et al. |
| 6,169,483 B1 | 1/2001 | Ghaffari et al. |
| 6,211,672 B1 | 4/2001 | Bauman et al. |
| 6,230,888 B1 | 5/2001 | Frieze et al. |
| 6,264,106 B1 | 7/2001 | Bridgelall |
| 6,265,962 B1 | 7/2001 | Black et al. |
| 6,294,997 B1 | 9/2001 | Paratore et al. |
| 6,300,872 B1 | 10/2001 | Mathias et al. |
| 6,305,605 B1 | 10/2001 | Goetz et al. |
| 6,307,517 B1 | 10/2001 | Lee |
| 6,342,187 B1 | 1/2002 | Jacob et al. |
| 6,366,206 B1 | 4/2002 | Ishikawa et al. |
| 6,377,176 B1 | 4/2002 | Lee |
| 6,394,355 B1 | 5/2002 | Schlieffers et al. |
| D459,246 S | 6/2002 | Power et al. |
| 6,424,262 B2 | 7/2002 | Garber et al. |
| 6,424,263 B1 | 7/2002 | Lee et al. |
| 6,429,776 B1 | 8/2002 | Alicot et al. |
| 6,446,794 B1 | 9/2002 | Hacikyan |
| 6,448,886 B2 | 9/2002 | Garber et al. |
| 6,483,427 B1 | 11/2002 | Werb |
| 6,484,050 B1 | 11/2002 | Carroll et al. |
| 6,486,783 B1 | 11/2002 | Hausladen et al. |
| 6,492,905 B2 | 12/2002 | Mathias et al. |
| 6,492,933 B1 | 12/2002 | McEwan |
| 6,496,112 B1 | 12/2002 | Vega |
| 6,496,113 B2 | 12/2002 | Lee et al. |
| 6,509,217 B1 | 1/2003 | Reddy |
| 6,512,478 B1 | 1/2003 | Chien |
| 6,516,272 B2 | 2/2003 | Lin |
| 6,523,681 B1 | 2/2003 | Hacikyan |
| 6,535,175 B2 | 3/2003 | Brady et al. |
| 6,600,905 B2 | 7/2003 | Greeff et al. |
| 6,609,656 B1 | 8/2003 | Elledge |
| 6,618,024 B1 | 9/2003 | Adair et al. |
| 6,659,344 B2 * | 12/2003 | Otto et al. .................. 235/381 |
| 6,686,829 B1 | 2/2004 | Hohberger et al. |
| 6,696,954 B2 | 2/2004 | Chung |
| 6,698,285 B1 | 3/2004 | Hacikyan |
| 6,708,881 B2 | 3/2004 | Hartmann |
| 6,720,866 B1 | 4/2004 | Sorrells et al. |
| 6,724,309 B2 | 4/2004 | Grose et al. |
| 6,753,782 B2 | 6/2004 | Power |
| 6,756,880 B2 | 6/2004 | Hartmann |
| 6,757,068 B2 | 6/2004 | Foxlin |
| 6,759,789 B2 | 7/2004 | Hartmann |
| 6,777,623 B2 | 8/2004 | Ballard |
| 6,812,707 B2 | 11/2004 | Yonezawa et al. |
| 6,838,874 B1 | 1/2005 | Franklin |
| 6,853,194 B2 | 2/2005 | Nelson et al. |
| 6,859,190 B2 | 2/2005 | Pillai et al. |
| 6,861,954 B2 | 3/2005 | Levin |
| 6,940,408 B2 | 9/2005 | Ferguson et al. |
| 6,959,031 B2 | 10/2005 | Haynes et al. |
| 6,967,574 B1 | 11/2005 | Nelson |
| 6,987,451 B2 | 1/2006 | McKeown et al. |
| 6,989,750 B2 | 1/2006 | Shanks et al. |
| 6,998,541 B2 | 2/2006 | Morris et al. |
| 7,001,366 B2 | 2/2006 | Ballard |
| 7,005,968 B1 | 2/2006 | Bridgelall |
| 7,009,519 B2 | 3/2006 | Leonard et al. |
| 7,019,650 B2 | 3/2006 | Volpi et al. |
| 7,023,356 B2 * | 4/2006 | Burkhardt et al. ....... 340/825.49 |
| 7,079,034 B2 | 7/2006 | Stilp |
| 7,100,052 B2 | 8/2006 | Ghazarian |
| 7,126,479 B2 | 10/2006 | Claessens et al. |
| 7,129,840 B2 * | 10/2006 | Hull et al. .................. 340/568.1 |
| 7,158,034 B2 | 1/2007 | Corbett |
| 7,193,504 B2 | 3/2007 | Carrender et al. |
| 7,301,648 B2 | 11/2007 | Foxlin |
| 7,307,530 B2 | 12/2007 | Fabian et al. |
| 7,411,506 B2 | 8/2008 | Volpi et al. |
| 7,501,948 B2 | 3/2009 | Roemerman et al. |
| 7,541,933 B2 | 6/2009 | Volpi et al. |
| 7,557,711 B2 | 7/2009 | Volpi et al. |
| 7,600,613 B2 | 10/2009 | Kang et al. |
| 7,671,744 B2 | 3/2010 | Volpi et al. |
| 7,755,491 B2 | 7/2010 | Volpi et al. |
| 7,760,097 B2 | 7/2010 | Volpi et al. |

| | | |
|---|---|---|
| 7,893,840 B2 | 2/2011 | Volpi et al. |
| 2001/0004237 A1 | 6/2001 | Lake et al. |
| 2001/0008390 A1 | 7/2001 | Berquist et al. |
| 2001/0013830 A1 | 8/2001 | Garber et al. |
| 2001/0034530 A1 | 10/2001 | Malackowski et al. |
| 2002/0005774 A1 | 1/2002 | Rudolph et al. |
| 2002/0008623 A1 | 1/2002 | Garber et al. |
| 2002/0010679 A1 | 1/2002 | Felsher |
| 2002/0044096 A1 | 4/2002 | Chung |
| 2002/0048330 A1 | 4/2002 | Schetelig et al. |
| 2002/0060630 A1 | 5/2002 | Power |
| 2002/0067263 A1 | 6/2002 | Tafoya et al. |
| 2002/0070845 A1 | 6/2002 | Reisinger et al. |
| 2002/0093431 A1 | 7/2002 | Zierolf |
| 2002/0105424 A1 | 8/2002 | Alicot et al. |
| 2002/0158120 A1 | 10/2002 | Zierolf |
| 2003/0006762 A1 | 1/2003 | Clements |
| 2003/0007473 A1 | 1/2003 | Strong et al. |
| 2003/0025604 A1 | 2/2003 | Freeman |
| 2003/0031819 A1 | 2/2003 | Adams et al. |
| 2003/0076230 A1 | 4/2003 | Runyon et al. |
| 2003/0083964 A1* | 5/2003 | Horwitz et al. .................. 705/28 |
| 2003/0111540 A1 | 6/2003 | Hartmann |
| 2003/0128100 A1* | 7/2003 | Burkhardt et al. .............. 340/5.8 |
| 2003/0141366 A1 | 7/2003 | Hartmann |
| 2003/0142691 A1 | 7/2003 | Hartmann |
| 2003/0142741 A1 | 7/2003 | Hartmann |
| 2003/0142742 A1 | 7/2003 | Hartmann |
| 2003/0145036 A1 | 7/2003 | Hartmann et al. |
| 2003/0179072 A1 | 9/2003 | Hartmann |
| 2003/0179077 A1 | 9/2003 | Hartmann et al. |
| 2003/0179093 A1 | 9/2003 | Hartmann et al. |
| 2003/0179150 A1 | 9/2003 | Adair et al. |
| 2003/0192722 A1 | 10/2003 | Ballard |
| 2003/0214389 A1 | 11/2003 | Arneson et al. |
| 2004/0031626 A1 | 2/2004 | Morris et al. |
| 2004/0046643 A1 | 3/2004 | Becker et al. |
| 2004/0075361 A1 | 4/2004 | Hartmann |
| 2004/0075560 A1 | 4/2004 | Hartmann et al. |
| 2004/0085192 A1 | 5/2004 | Hartmann |
| 2004/0090868 A1 | 5/2004 | Endo et al. |
| 2004/0100376 A1 | 5/2004 | Lye et al. |
| 2004/0129279 A1 | 7/2004 | Fabian et al. |
| 2004/0142660 A1 | 7/2004 | Churan |
| 2004/0155651 A1 | 8/2004 | Britton |
| 2004/0174261 A1 | 9/2004 | Volpi et al. |
| 2004/0250819 A1 | 12/2004 | Blair et al. |
| 2005/0021172 A1 | 1/2005 | Winter et al. |
| 2005/0088299 A1 | 4/2005 | Bandy et al. |
| 2005/0110614 A1 | 5/2005 | Coates et al. |
| 2005/0116033 A1 | 6/2005 | Moore |
| 2005/0128519 A1 | 6/2005 | Yamauchi |
| 2005/0201450 A1 | 9/2005 | Volpi et al. |
| 2005/0207617 A1 | 9/2005 | Sarnoff |
| 2005/0230110 A1 | 10/2005 | Ellison et al. |
| 2005/0240305 A1 | 10/2005 | Bogash et al. |
| 2005/0248456 A1 | 11/2005 | Britton, Jr., et al. |
| 2005/0282558 A1 | 12/2005 | Choi et al. |
| 2006/0006986 A1 | 1/2006 | Gravelle et al. |
| 2006/0017545 A1 | 1/2006 | Volpi et al. |
| 2006/0044137 A1 | 3/2006 | Morris et al. |
| 2006/0077036 A1 | 4/2006 | Roemerman et al. |
| 2006/0132351 A1 | 6/2006 | Le Sesne |
| 2006/0202827 A1 | 9/2006 | Volpi et al. |
| 2006/0241399 A1 | 10/2006 | Fabian |
| 2006/0265164 A1 | 11/2006 | Clark |
| 2007/0032224 A1* | 2/2007 | Boyer et al. .................. 455/417 |
| 2007/0035383 A1 | 2/2007 | Roemerman et al. |
| 2007/0210921 A1 | 9/2007 | Volpi et al. |
| 2007/0216526 A1 | 9/2007 | Volpi et al. |
| 2008/0018432 A1 | 1/2008 | Volpi et al. |
| 2008/0018468 A1 | 1/2008 | Volpi et al. |
| 2008/0018469 A1 | 1/2008 | Volpi et al. |
| 2008/0024276 A1 | 1/2008 | Volpi et al. |
| 2008/0024277 A1 | 1/2008 | Volpi et al. |
| 2008/0024278 A1 | 1/2008 | Volpi et al. |
| 2009/0040025 A1 | 2/2009 | Volpi et al. |
| 2009/0045917 A1 | 2/2009 | Volpi et al. |

FOREIGN PATENT DOCUMENTS

| | | |
|---|---|---|
| EP | 0 639 817 A1 | 2/1995 |
| EP | 0 948 940 A1 | 10/1999 |
| FR | 2 625 258 A1 | 2/1990 |
| WO | WO 96/04530 | 2/1996 |
| WO | WO 99/11086 A1 | 3/1999 |

OTHER PUBLICATIONS

U.S. Appl. No. 10/997,617, Nov. 24, 2004, Tepera, et al.

"EPC™ Radio-Frequency Identity Protocols Class-1 Generation-2 UHF RFID Protocol for Communications at 860 MHz—960 MHz," Version 1.0.9, Jan. 31, 2005, pp. 1-94, EPCglobal Inc.™, Lawrenceville, NJ.

"Technical Report: 860MHz-930MHz Class I Radio Frequency Identification Tag Radio Frequency & Logical Communication Interface Specification Candidate Recommendation," Version 1.0.1, Nov. 14, 2002, pp. 1-17, Auto-ID Center, Massachusetts Institute of Technology, Cambridge, MA.

Wald, H., et al., "Making Health Care Safer: A Critical Analysis of Patient Safety Practices," Evidence Report/Technology Assessment No. 43, Jul. 20, 2001, Ch. 43, pp. 487-499, University of California at San Francisco (UCSF—Stanford University, San Francisco, CA.

"Whitepaper: EPCglobal Class 1 Gen 2 RFID Specification," 2005 (approved Dec. 2004), pp. 1-7, http://www.alientechnology.com/docs/AT_wp_EPCGlobal_WEB.pdf, Alien Technology Corporation, Morgan Hill, CA.

"Automatic Identification—Radio Frequency Identification for Item Management," Part 6: Mode 3—Physical Layer, Anti Collision System and Protocols for Ultra High Frequency (UHF) Systems, Feb. 1, 2002, pp. 48-50, Reference Number of Document: ISO/IEC WD 18000-6 Mode 3, Committee Identification: ISO/IEC SC31/WG 4, Secretariat: ANSI.

Codd, E.F., "A Relational Model of Data for Large Shared Data Banks," Communications of the ACM, Jun. 1970, pp. 377-387, vol. 13, No. 6, Association for Computing Machinery, New York, NY.

* cited by examiner

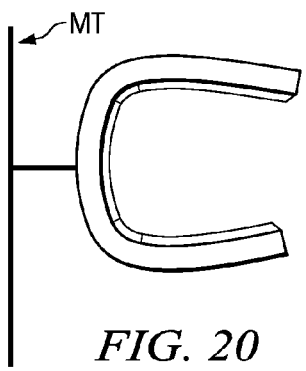
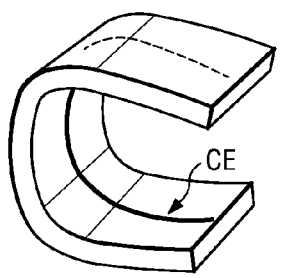
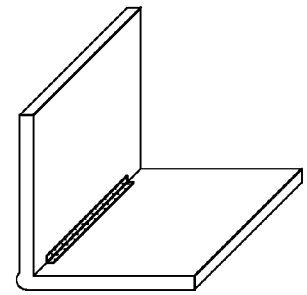
FIG. 20  FIG. 21  FIG. 22
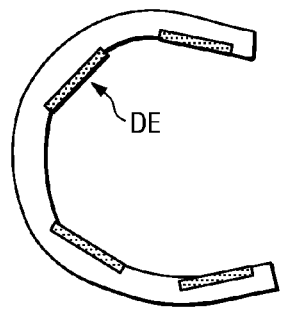
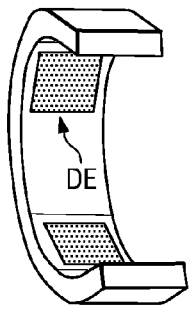
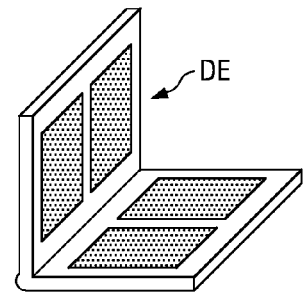
FIG. 23  FIG. 24  FIG. 25
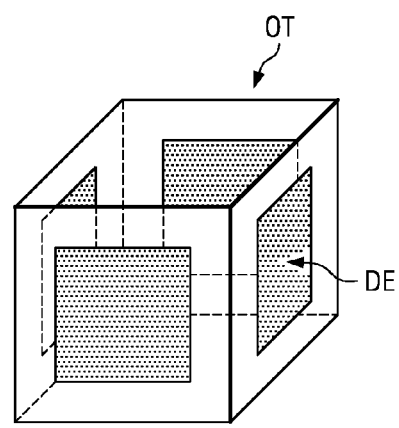
FIG. 26

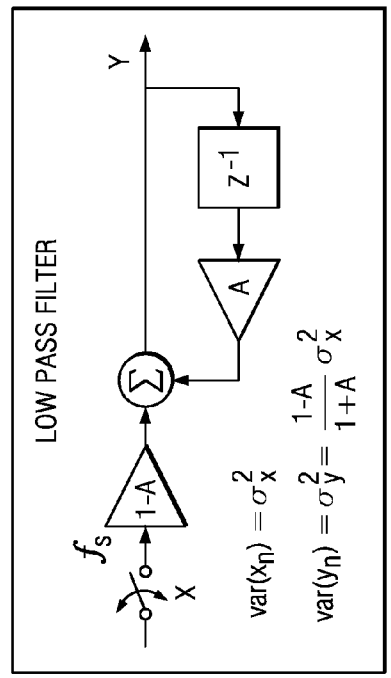
*FIG. 43*
*FIG. 42*
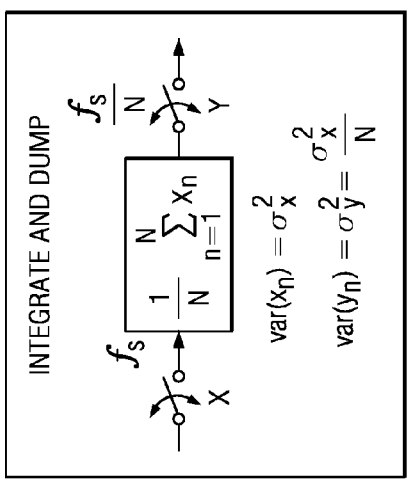
*FIG. 45*

6620

6730
6740

6860  6850

INTERROGATOR AND INTERROGATION SYSTEM EMPLOYING THE SAME

This application claims the benefit of U.S. Provisional Application No. 60/836,997, entitled "Interrogation Systems," filed on Aug. 11, 2006, and is a continuation in part of U.S. patent application Ser. No. 11/357,225 (also U.S. Patent Application Publication No. 2006/0202827), entitled "Interrogator and Interrogation System Employing the Same," filed Feb. 17, 2006 now U.S. Pat. No. 7,760,097, which is a continuation of U.S. patent application Ser. No. 10/378,043 (also U.S. Pat. No. 7,019,650, the '650 patent), entitled "Interrogator and Interrogation System Employing the Same," filed Mar. 3, 2003 now U.S. Pat. No. 7,019,650, and is a continuation in part of U.S. patent application Ser. No. 11/071,652 (also U.S. Patent Application Publication No. 2005/0201450, the '450 Publication), entitled "Interrogator and Interrogation System Employing the Same," filed Mar. 3, 2005. All of the aforementioned applications are incorporated by reference.

TECHNICAL FIELD

The present invention is directed, in general, to communication systems and, more specifically, to an interrogator, method of discerning the presence of an object, and an interrogation system employing the same.

BACKGROUND

Asset tracking for the purposes of inventory control or the like is employed in a multitude of industry sectors such as in the food industry, apparel markets and any number of manufacturing sectors, to name a few. In many instances, a bar coded tag or radio frequency identification ("RFID") tag is affixed to the asset and a reader interrogates the item to read the tag and ultimately to account for the asset being tracked. Although not readily adopted, an analogous system may be employed in a medical environment to track equipment such as an Electrocardiogram ("EKG") machine or other modular patient monitoring equipment.

Of particular note is a surgical environment in which for preparation for surgery a previously sterilized instrument kit of surgical instruments and disposable items (collectively referred to as surgical items) is brought into a surgical suite. The instrument kit contains an assortment of surgical items including hemostats, clamps, forceps, scissors, sponges, and the like, based on the type of surgery to be performed. Typically, a scrub nurse removes the surgical items from the kit and arranges them on a back table located behind the operating table. The surgical items are organized in rows on rolled toweling for ease of access and handling by a surgeon and supporting team. During the course of a surgical procedure, the surgical items are often positioned on a "Mayo" stand proximate the operating table, while the unused surgical items remain on the back table. During the course of and at the conclusion of the surgery, all of the surgical items must be carefully counted to, among other things, avoid leaving any surgical items in a patient.

In view of the consequences, surgical items are typically counted at least three times during the course of a surgical procedure. The first count is performed prior to the start of the procedure; the second count is performed prior to a closure of the patient; the third count is performed at the conclusion of the procedure. In many instances, such as when more than one surgical team is assigned to a procedure, many more counts of the surgical items, often involving different personnel (e.g., a circulating nurse and a scrub nurse), are performed. As a matter of fact, the Association of PeriOperative Registered Nurses ("AORN") advocates four counts of the surgical items as part of its recommended practices for surgical procedures. Additionally, to keep track of the counts of the surgical items, rudimentary systems such as visual records scribbled on whiteboards or other more progressive computer tallying systems to designate the count of the surgical items are often employed.

In common practice, access to and from an operating room in the surgical suite is restricted during the counting process, thereby resulting in a detention of valuable professional personnel. A discrepancy in the count must be resolved by additional counts, physical examination of the patient or x-ray examination, if necessary. Although it is unusual for a discrepancy in the count to result from a surgical item remaining in the patient, counting and recounting occurs in every surgical procedure and the repercussions associated with the loss of a surgical item is of grave concern to a medical facility and the professionals.

Thus, the multiple manual counting of surgical items is time consuming, ties up key professional personnel, contributes to surgical suite down time, distracts personnel from the surgical procedure, lengthens the time the patient is exposed to anesthesia leading to an increase in mortality and morbidity risk, is generally distasteful to all involved, and still results in errors wherein materials are left in the patient. It should be quite understandable that the average cost overruns of such delays associated with the personnel, capital equipment and the surgical suite itself can run into the tens of thousands of dollars per procedure. On an annual basis, the loss of productivity associated with the surgical suite is quite sizeable and should be addressed to bolster the bottom line of a medical facility.

Even with the degree of caution cited above, the problem associated with the loss of surgical items, especially surgical items retained within patients, is a serious one and has a significant influence on the costs of malpractice insurance. As a matter of fact, retained foreign bodies within a patient is one of the most prevalent categories of malpractice claims and the most common retained foreign body is a sponge. In accordance therewith, there is a diagnosis known as "gossypiboma" (wherein gossypium is Latin for cotton and boma is Swahili for place of concealment) for the retention of a sponge-like foreign body in a patient. The medical literature is scattered with reports of presentations of retained sponges found days, months, or even years after a surgical procedure.

The sponge is typically made of gauze-like material with dimensions often covering a four-inch square or a two-inch by four-inch rectangle. At one time sponges were commonly made of cotton, but now a number of filament materials are used. Occasionally, a filament of radiopaque material [e.g., barium sulfate ("$BaSO_4$")] is woven into the surgical sponge, or a tab of that material is attached to the surgical sponge. The filament or tab is provided to produce a distinct signature on an x-ray machine for the purpose of determining if a sponge is present in the patient. While this is generally effective, even these filaments or tabs are not 100% effective in aiding the location of the sponges. Different researchers report that x-ray methods to supplement manual counting are fallible.

Moreover, in cases when a sponge remains in the body for a long time, the radiopaque filament can become difficult to locate and may even conform to internal structures. Some have suggested that a computerized tomography ("CT") scan can be more effective than an x-ray examination because the CT scans and ultrasonography may detect the reduced density of a sponge and its characteristic pattern of air or gas bubbles trapped within the sponge. Many radiologists have published a number of papers over the years on the problem of finding lost sponges and these are generally known in the field of medicine.

As mentioned above, there is a widespread practice in other fields for counting, tracking and accounting for items and two of the more prevalent and lowest cost approaches involve various types of bar coding and RFID techniques. As with bar coding, the RFID techniques are primarily used for automatic data capture and, to date, the technologies are generally not compatible with the counting of surgical items. A reason for the incompatibility in the medical environment for the bar coding and RFID techniques is a prerequisite to identify items covered in fluids or waste, and the exigencies associated with the sterilizing of surgical items including a readable tag. Even in view of the foregoing limitations for the application of RFID techniques in the medical environment wherein less than ideal conditions are prevalent, RFID tags have been compatible with a number of arduous environments. In the pharmaceutical industry, for instance, RFID tags have survived manufacturing processes that require products to be sterilized for a period of time over 120 degrees Celsius. Products are autoclaved while mounted on steel racks tagged with an RFID tag such that a rack identification ("ID") number and time/date stamp can be automatically collected at the beginning and end of the process as the rack travels through the autoclave on a conveyor. The RFID tags can be specified to withstand more than 1000 hours at temperatures above 120 degrees Celsius. This is just one example of how RFID tags can withstand the arduous environment including the high temperatures associated with an autoclave procedure, whereas a bar code label is unlikely to survive such treatment.

While identification tags or labels may be able to survive the difficult conditions associated with medical applications, there is yet another challenge directed to attaching an identification element to a surgical item or any small device. The RFID tags are frequently attached to devices by employing mechanical techniques or may be affixed with sewing techniques. A more common form of attachment of an RFID tag to a device is by bonding techniques including encapsulation or adhesion.

While medical device manufacturers have multiple options for bonding, critical disparities between materials may exist in areas such as biocompatibility, bond strength, curing characteristics, flexibility and gap-filling capabilities. A number of bonding materials are used in the assembly and fabrication of both disposable and reusable medical devices, many of which are certified to United States Pharmacopoeia Class VI requirements. These products include epoxies, silicones, ultraviolet curables, cyanoacrylates, and special acrylic polymer formulations.

In many instances, the toughness and versatile properties of biocompatible epoxies make them an attractive alternative. Epoxies form strong and durable bonds, fill gaps effectively and adhere well to most types of substrates. Common uses for medical epoxies include a number of applications which require sterilization compatibility such as bonding lenses in endoscopes, attaching plastic tips to tubing in disposable catheters, coating implantable prosthetic devices, bonding balloons to catheters for balloon angioplasty, and bonding diamond scalpel blades for coronary bypass surgery, to name a few. A wide range of such materials are available and some provide high strength bonds which are tough, water resistant, low in outgassing, and dimensionally stable over a temperature range of up to 600 degrees Fahrenheit. Some epoxies can withstand repeated sterilization such as autoclaving, radiation, ethylene oxide and cold (e.g., chemical) sterilization methods.

As previously mentioned, familiar applications for RFID techniques include "smart labels" in airline baggage tracking and in many stores for inventory control and for theft deterrence. In some cases, the smart labels may combine both RFID and bar coding techniques. The tags may include batteries and typically only function as read only devices or as read/write devices. Less familiar applications for RFID techniques include the inclusion of RFID tags in automobile key fobs as anti-theft devices, identification badges for employees, and RFID tags incorporated into a wrist band as an accurate and secure method of identifying and tracking prison inmates and patrons at entertainment and recreation facilities. Within the medical field, RFID tags have been proposed for tracking patients and patient files, employee identification badges, identification of blood bags, and process management within the factories of manufacturers making products for medical practice.

Typically, RFID tags without batteries (i.e., passive devices) are smaller, lighter and less expensive than those that are active devices. The passive RFID tags are typically maintenance free and can last for long periods of time. The passive RFID tags are relatively inexpensive, generally as small as an inch in length, and about an eighth of an inch in diameter when encapsulated in hermetic glass cylinders. Recent developments indicate that they will soon be even smaller. The RFID tags can be encoded with 64 or more bits of data that represent a large number of unique ID numbers (e.g., about 18,446,744,073,709,551,616 unique ID numbers). Obviously, this number of encoded data provides more than enough unique codes to identify every item used in a surgical procedure or in other environments that may benefit from asset tracking.

An important attribute of RFID interrogation systems is that a number of RFID tags should be interrogated simultaneously stemming from the signal processing associated with the techniques of impressing the identification information on the carrier signal. A related and desirable attribute is that there is not typically a minimum separation required between the RFID tags. Using an anti-collision algorithm, multiple RFID tags may be readily identifiable and, even at an extreme reading range, only minimal separation (e.g., five centimeters or less) to prevent mutual de-tuning is generally necessary. Most other identification systems, such as systems employing bar codes, usually impose that each device be interrogated separately. The ability to interrogate a plurality of closely spaced RFID tags simultaneously is desirable for applications requiring rapid interrogation of a large number of items.

In general, the sector of radio frequency identification is one of the fastest growing areas within the field of automatic identification and data collection. A reason for the proliferation of RFID systems is that RFID tags may be affixed to a variety of diverse objects (also referred to as "RFID objects") and a presence of the RFID tags may be detected without actually physically viewing or contacting the RFID tag. As a result, multiple applications have been developed for the RFID systems and more are being developed every day.

The parameters for the applications of the RFID systems vary widely, but can generally be divided into three significant categories. First, an ability to read the RFID tags rapidly. Another category revolves around an ability to read a significant number of the RFID tags simultaneously (or nearly simultaneously). A third category stems from an ability to read the RFID tags reliably at increased ranges or under conditions wherein the radio frequency signals have been substantially attenuated. While significant progress has been made in the area of reading multiple RFID tags almost simultaneously (see, for instance, U.S. Pat. No. 6,265,962 entitled "Method for Resolving Signal Collisions Between Multiple RFID Transponders in a Field," to Black, et al., issued Jul. 24, 2001, which is incorporated herein by reference), there is still room for significant improvement in the area of reading the RFID tags reliably at increased ranges or under conditions when the radio frequency signals have been substantially attenuated.

Accordingly, what is needed in the art is an interrogator, interrogation system and related method to identify and account for all types of items regardless of the environment or application that overcomes the deficiencies of the prior art.

SUMMARY OF THE INVENTION

These and other problems are generally solved or circumvented, and technical advantages are generally achieved, by advantageous embodiments of the present invention which includes an interrogator and interrogation systems employing the same. In one embodiment, the interrogation systems include multiple interrogators that communicate with a base command unit to track a location of an object. In another embodiment wherein the object is an RFID object (e.g., an object with an RFID tag), the interrogators employ signal processing techniques such as precharging the RFID object, and correlating a reference code with a reply code from the RFID object using selected techniques to increase a sensitivity of the interrogator, especially for adverse environments. In other embodiments, the interrogation systems include variations of metal instruments and sponges employed therewith. In yet another embodiment, the interrogation system includes metal interrogators capable of discerning the presence of a metal object, especially in a presence of another metal object.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, reference is now made to the following descriptions taken in conjunction with the accompanying drawings, in which:

FIGS. 18 to 28 illustrate diagrams of exemplary antennas employable with an interrogation system constructed according to the principles of the present invention;

FIGS. 42 and 43 illustrate diagrams of embodiments of filters employable with a control and processing subsystem of an interrogator constructed according to the principles of the present invention;

FIG. 45 illustrates a diagram of a filter structure employable with a control and processing subsystem of an interrogator constructed according to the principles of the present invention;

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention. The present invention will be described with respect to exemplary embodiments in a specific context, namely, an interrogator, methods of discerning metal objects (e.g., objects that include metal), RFID objects (e.g., objects that include an RFID tag or radio frequency identification), and other objects, and an interrogation system employing the same. The principles of the present invention are applicable to many fields including, without limitation, the medical environment, supply chain management systems in the retail industry, and the defense industry.

Referring initially to FIGS. 1 to 14, illustrated are system level diagrams of embodiments of interrogation systems constructed according to the principles of the present invention. The interrogation systems include multiple interrogators (designated "INT") with corresponding antennas (designated "ANT") that define an active area for detecting, without limitation, RFID objects (e.g., objects such as a sponge with an RFID tag attached thereto), metal objects (e.g., objects including metal), and bar coded objects (e.g., objects such as a blood bag with a bar code thereon). The interrogators illustrated with respect to the interrogation systems of FIGS. 1 to 7 include far field antennas. The interrogators are located at stations (such as a back table, a soiled consumable (or disposable) and instrument station, a dirty basin station, and an operating station of an operating room).

Figure 6:
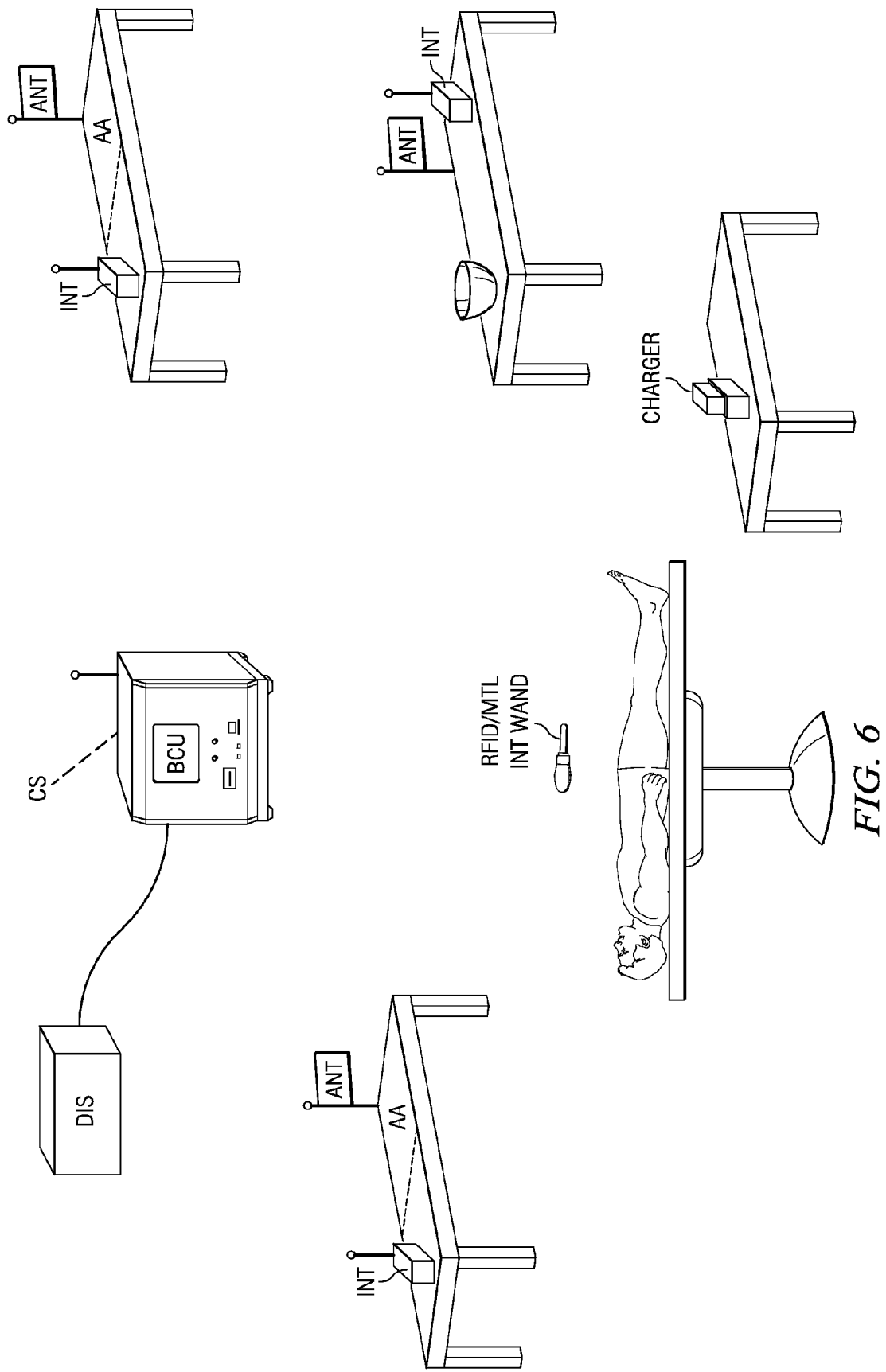

Additionally, ones of the interrogators form mobile interrogators with, for instance, an RFID wand (designated "RFID WAND;" see, e.g., FIG. 2), a metal wand (designated "MTL WAND;" see, e.g., FIG. 3), an integrated RFID and metal wand (designated "RFID/MTL WAND;" see, e.g., FIG. 5) or combinations thereof, located at a station such as an operating station. As illustrated in FIG. 6, selected ones of the mobile interrogators may be integrated RFID and metal interrogator wands (designated "RFID/MTL INT WAND") chargeable through a charger (designated "CHARGER"). While the illustrated mobile interrogators include RFID and metal wands, it should be understood that other technologies may be employed in conjunction with the mobile interrogators such as, without limitation, bar code, optical, optical recognition, microelectromechanical systems, radio frequency and dot-peening. As an example, optical scanning may be employed to detect and account for small items such as needles.

Figure 1:
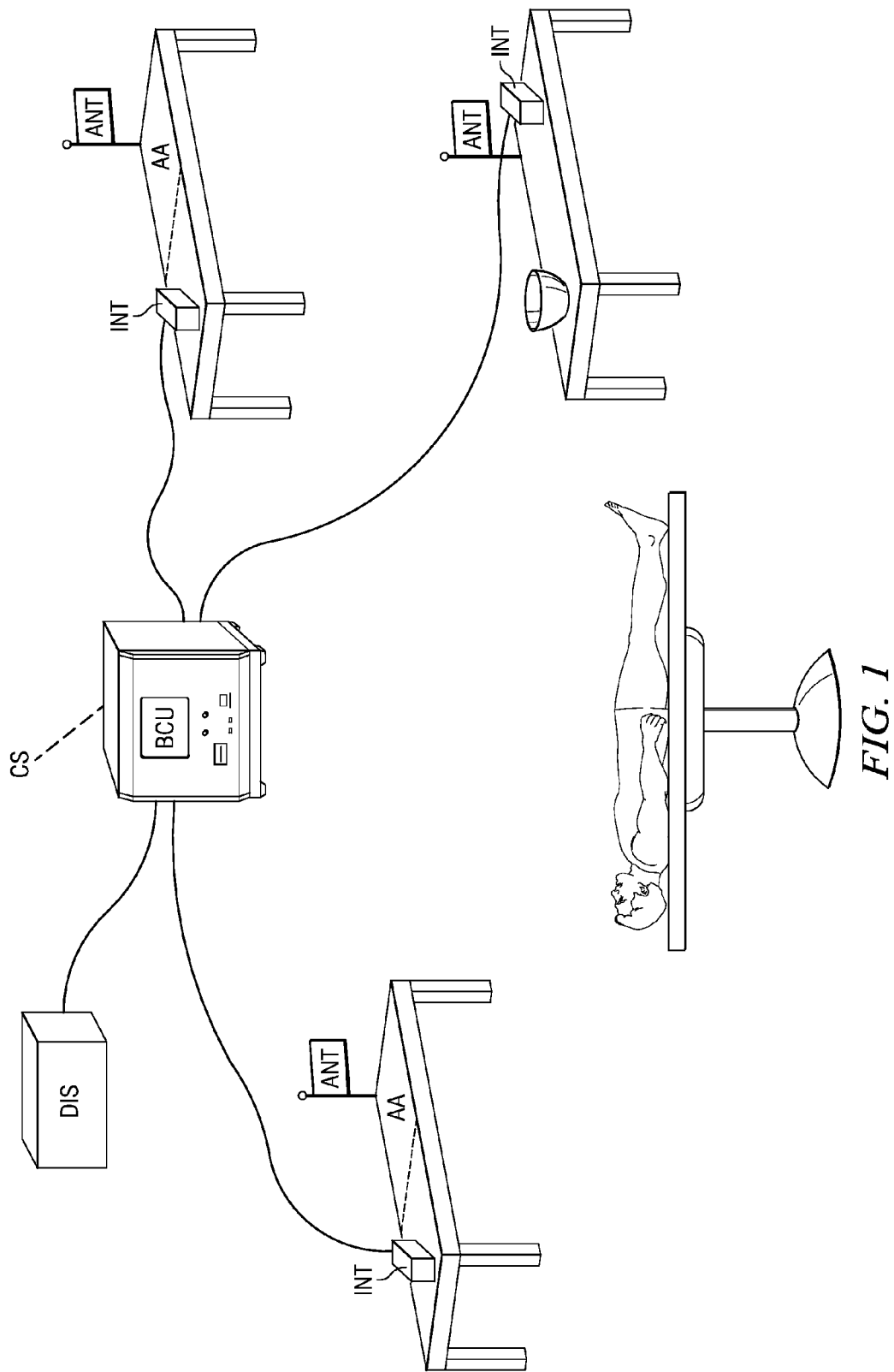
FIGS. 1 to 14 illustrate system level diagrams of embodiments of interrogation systems constructed according to the principles of the present invention.
Figure 2:
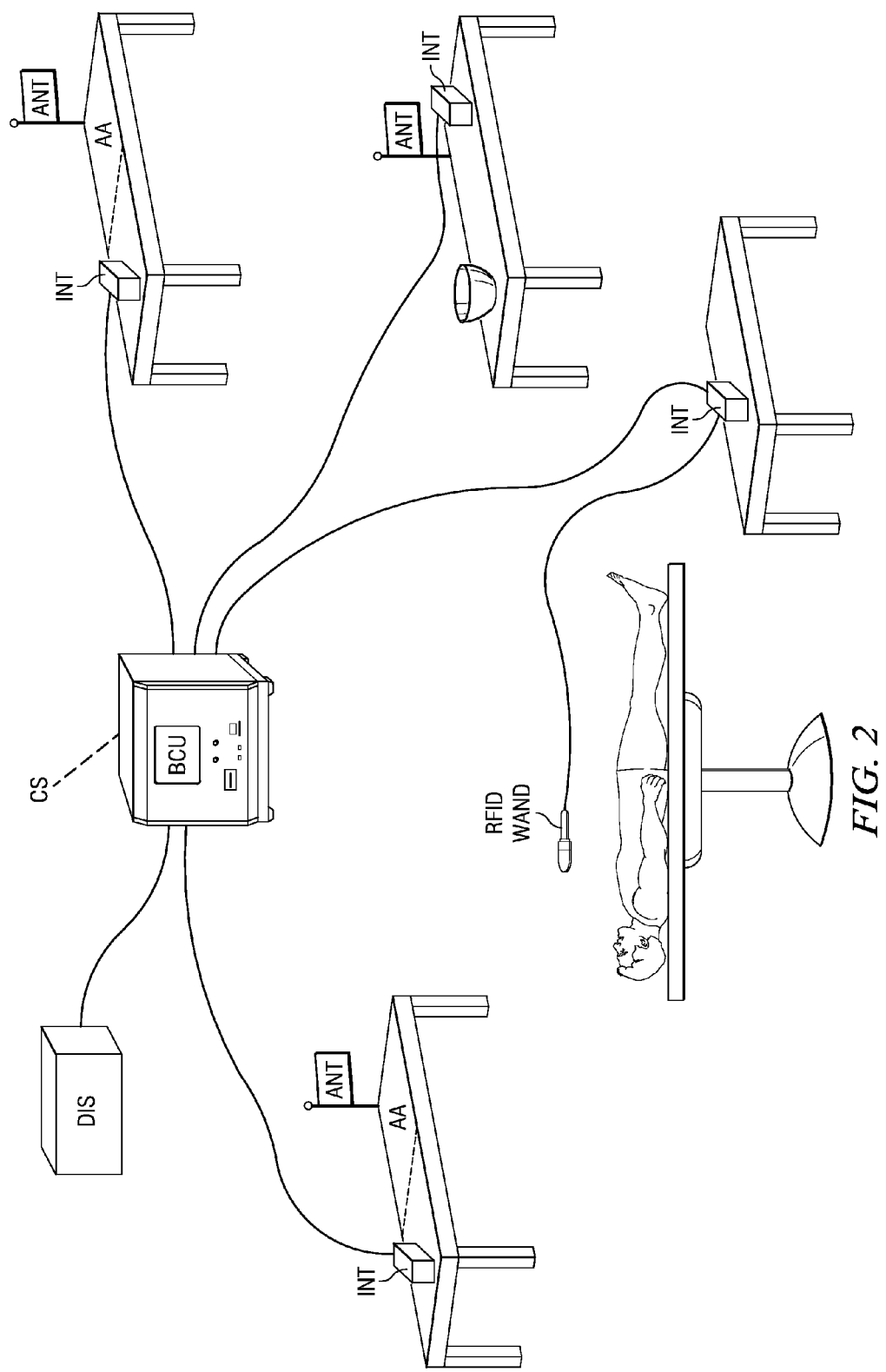
Figure 3:
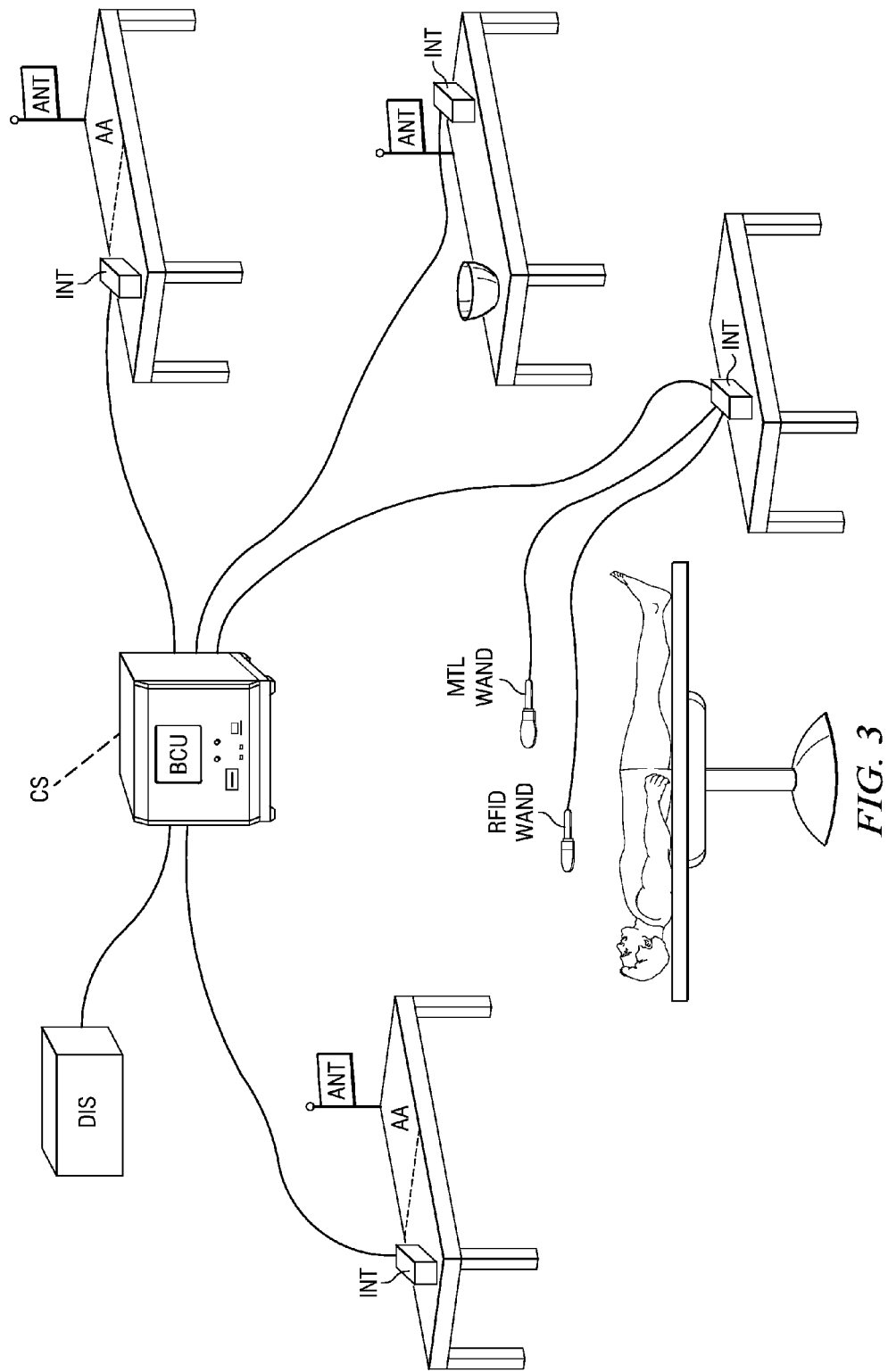
Figure 4:
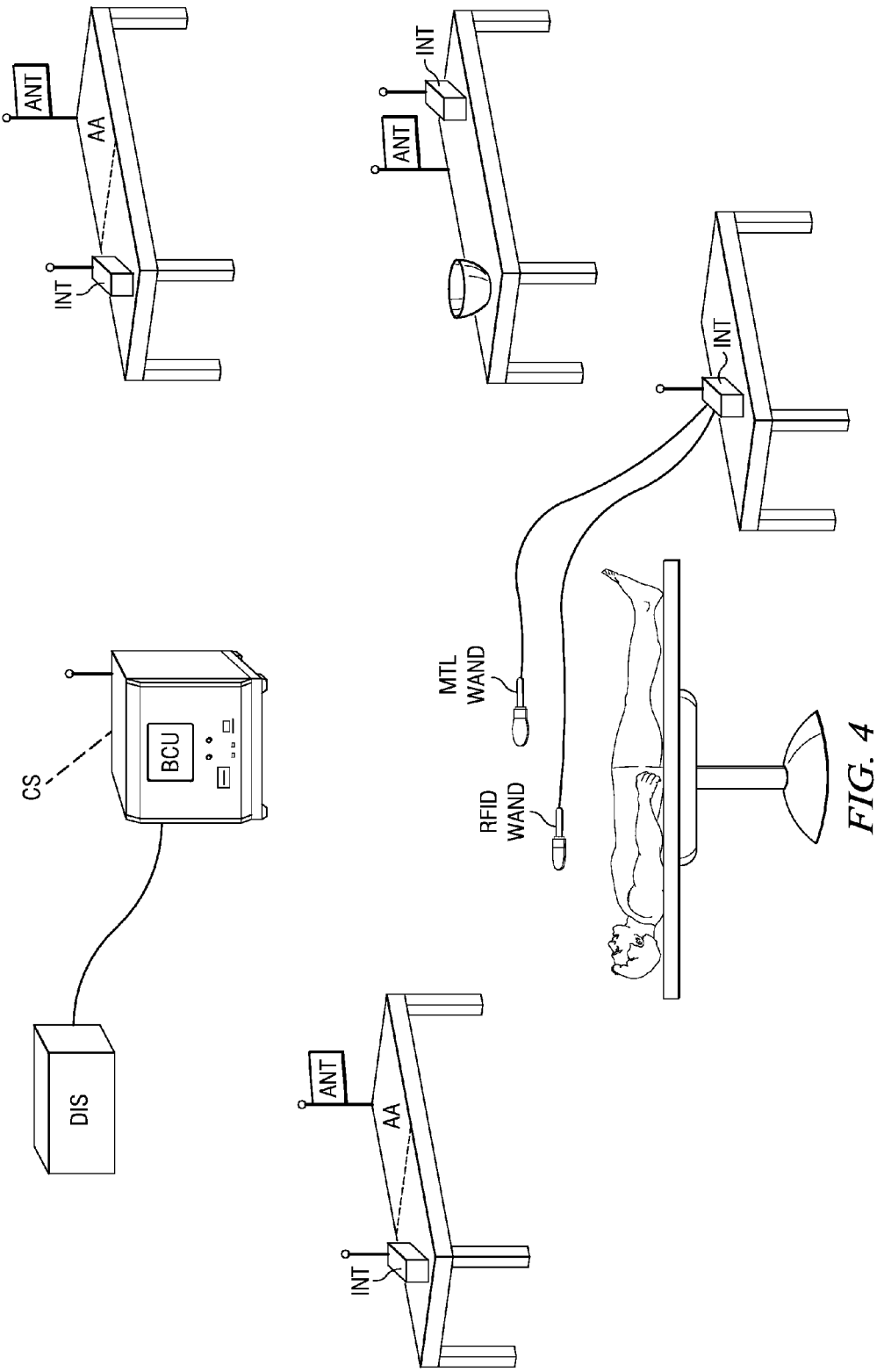
Figure 5:
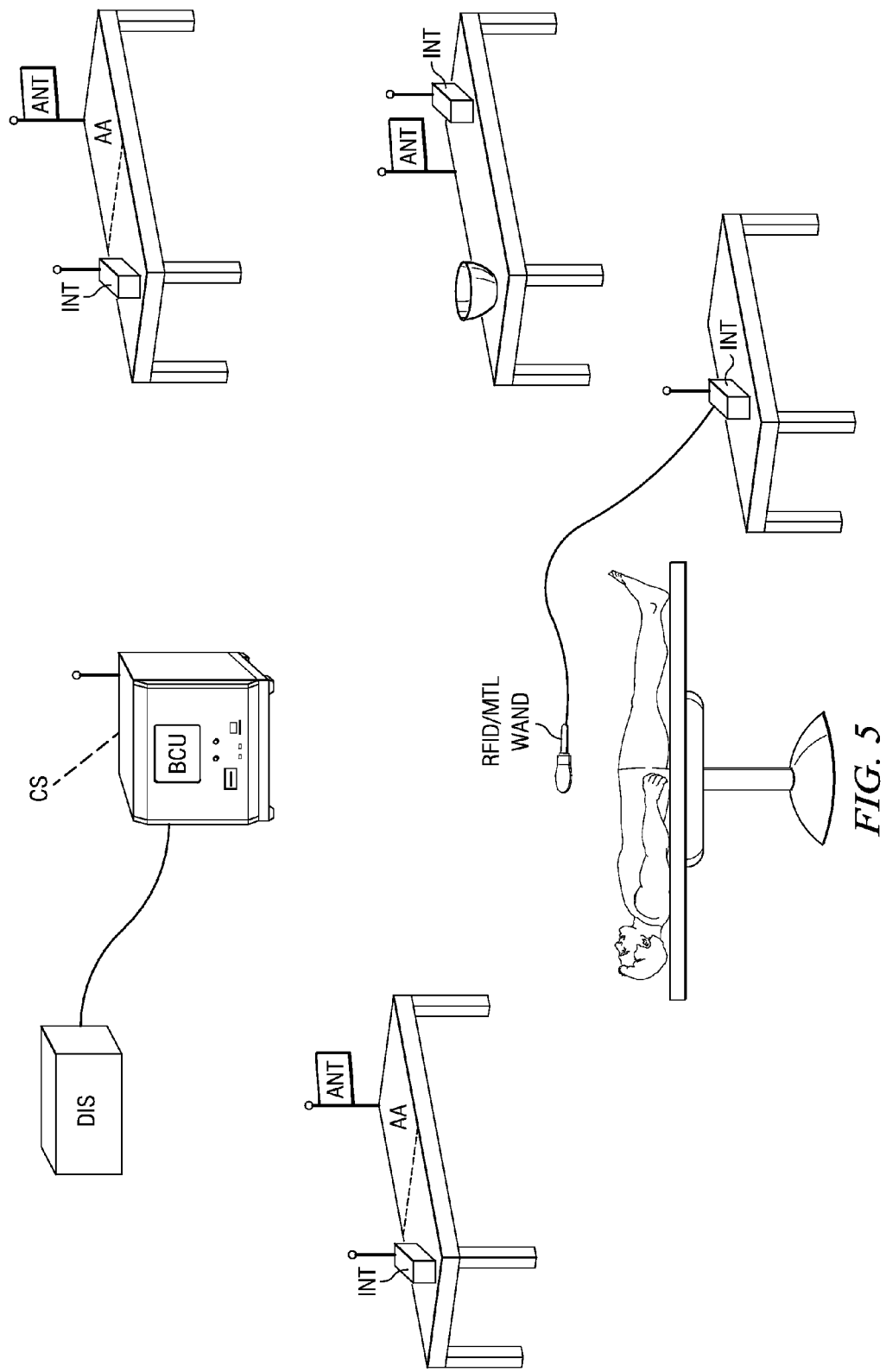

The interrogators are coupled to a base command unit (e.g., wirelessly as illustrated in FIG. 4) such as personal computer, a laptop computer, a server, or any computer processing system. The base command unit (designated "BCU") is coupled to another computer system (designated "CS") such as a hospital information technology system and a display (e.g., a wall mounted display designated "DIS"). The base command unit includes control and processing subsystems for the interrogation system.

Figure 7:
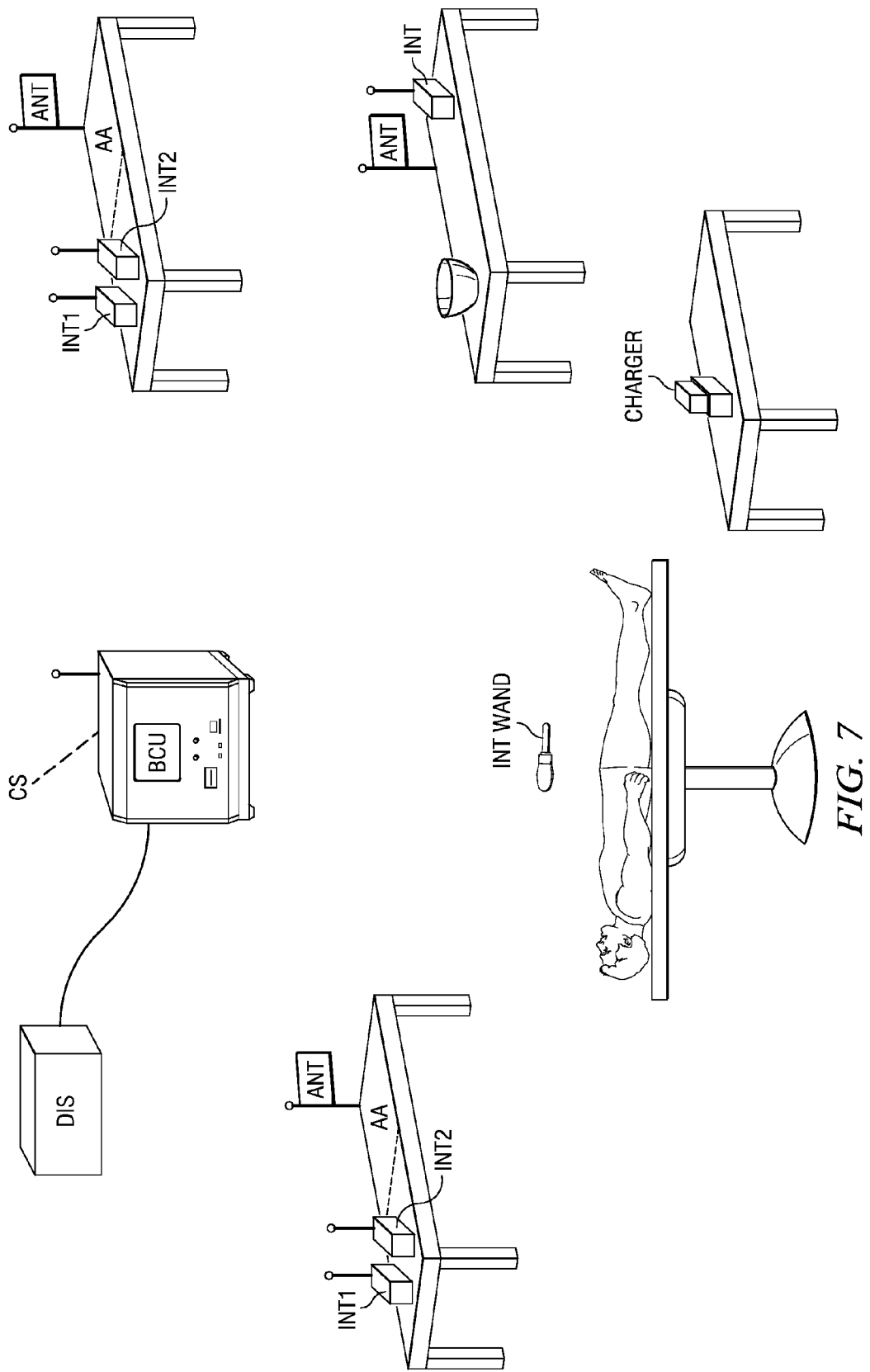
Figure 8:
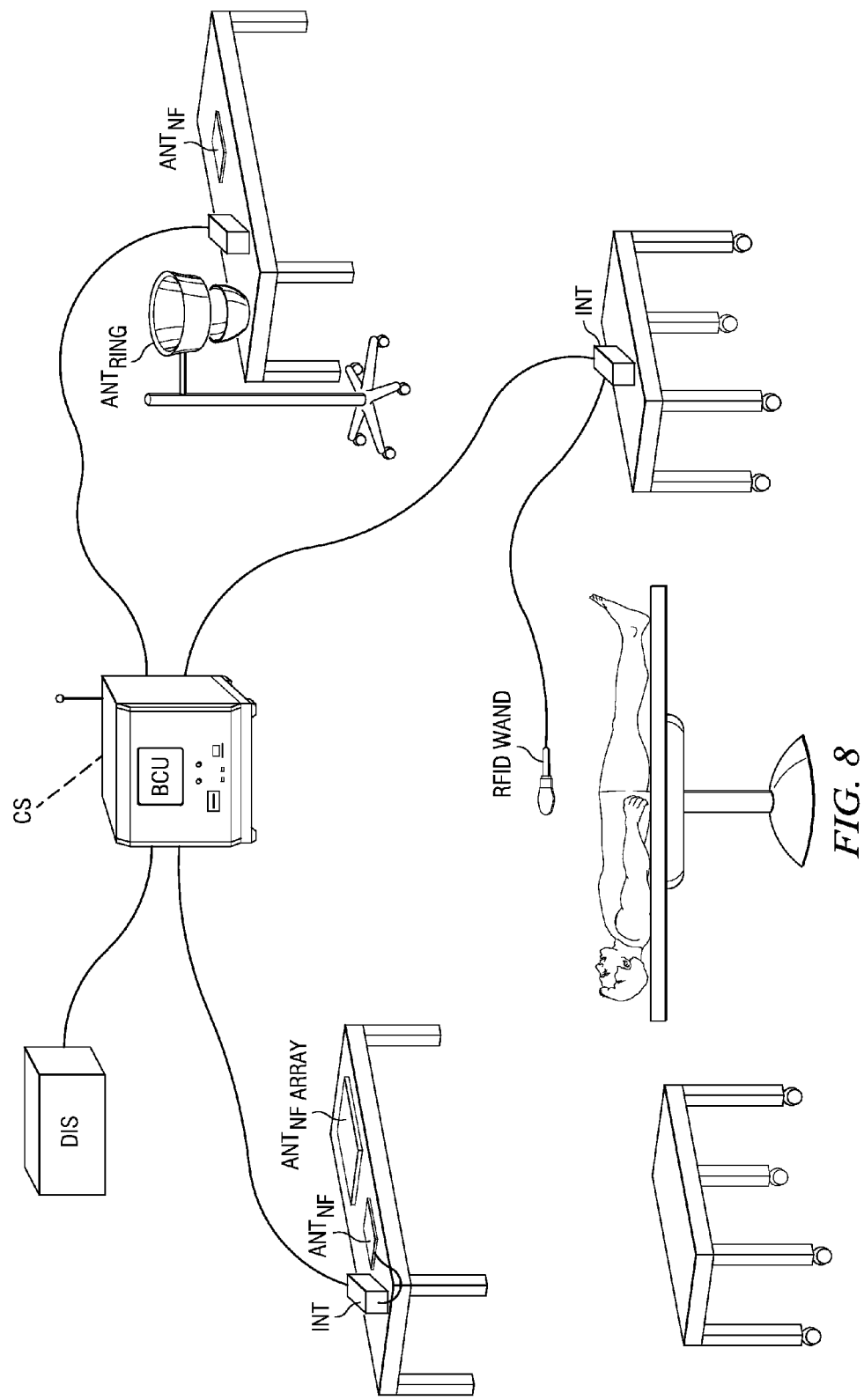

As illustrated in FIG. 7, the interrogation system may also incorporate multiple interrogators (designated "INT1" and "INT2") employing different types of technologies that accommodate different technologies such as, without limitation, RFID, metal, bar code, optical, optical recognition, microelectromechanical systems, radio frequency and dot-peening. Of course, the function of detecting different types of technologies may be integrated into a single interrogator. Thus, the interrogation systems can detect, count and account for objects such as, without limitation, RFID objects (e.g., object with an RFID tag), metal objects and bar coded objects (e.g., objects with a bar code). The interrogation systems allow an RFID object or other object to be read into the base command unit via an interrogator and reconciled, at a later time, by being read by the same or a different interrogator into the base command unit. The base command unit receives signals from the interrogators to track a location of an object, preferably in real time, which may be shown on a display. As illustrated in FIG. 8, the interrogators are operable with different types of antennas such as, without limitation, near field antennas (designated "$ANT_{NF}$"), ring antennas (designated "$ANT_{RING}$"), near field antenna arrays (designated "$ANT_{NF\ ARRAY}$") and bi-static antennas.

Another problem encountered is the ability to detect and read an RFID object at any location within a defined area. One method of accomplishing this function is to specifically place an antenna, for example, over a specific area so that that area may be monitored. However, in doing so, other RFID objects that may be in areas adjacent to the desired area can also be inadvertently read due to coverage overlap in the antennas thereby generating erroneous data. In addition, some environments strictly forbid antennas over areas wherein objects need to be detected. Also, the dimensions of the specific areas are not standardized and are required in various sizes and shapes that are not defined apriori. Therefore, what is needed is an interrogation system capable of reliably detecting and counting RFID objects in a well defined area while not erroneously counting them in adjacent areas and additionally able to easily define and modify this area both in size and shape.

Figure 9:
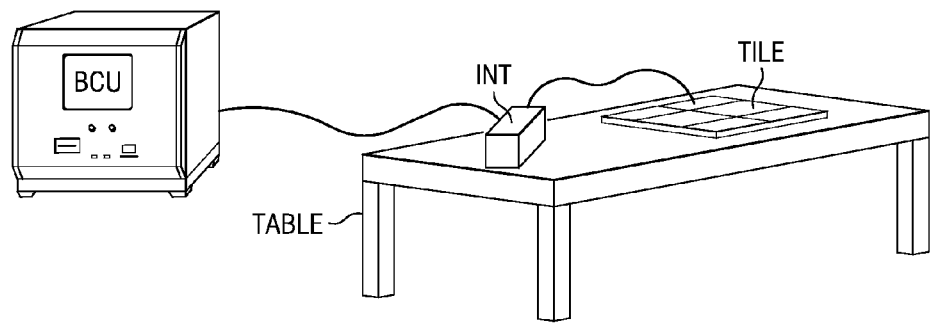

Turning now to FIG. 9, illustrated is a diagram of an interrogation system capable of providing interrogation (such as RFID interrogation) coverage to a specific and well defined area. An array of tiles (a tile of which is designated "TILE") is located on a surface of a table (designated "TABLE"). Each tile is individually capable of detecting and counting an object (e.g., an RFID object) if the RFID object is placed on or above that tile. The array is connected to an interrogator (designated "INT") via cabling that individually directs each tile to interrogate its specific area and reports the results back to a base command unit via cabling. The individual tiles are reconfigurable with respect to each other so that both the shape and size of the active area can be easily changed.

Figure 10:
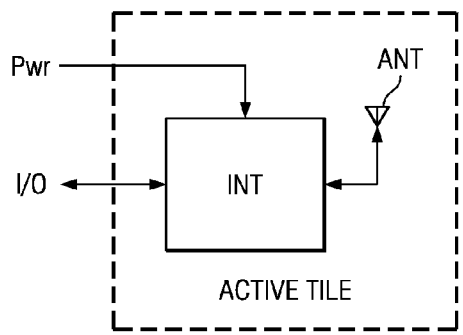

Turning now to FIG. 10, illustrated is a diagram of an embodiment of an active tile according to the principles of this invention. The active tile (designated "Active Tile") includes an integrated interrogator (designated "INT") connected to an antenna (designated "ANT"). The interrogator derives prime power (designated "Pwr") and input commands as well as outputting results (via an input/output bus designated "I/O") digitally to a controller.

Figure 11:
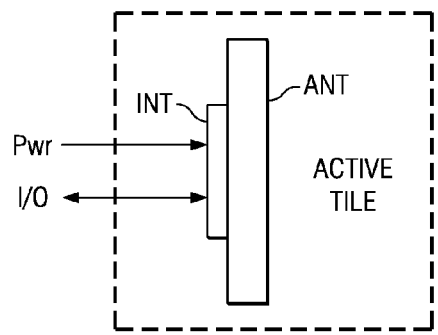

Turning now to FIG. 11, illustrated is a diagram of an embodiment of an active tile (designated "Active Tile") illustrating how an interrogator (designated "INT") is connected directly to an antenna (designated "ANT"). The side of the antenna opposite that side to which the interrogator is connected forms the radiating face of the antenna. Multiple tiles can be mounted side by side in various configurations to establish a desired area and size of desired coverage.

Figure 12:
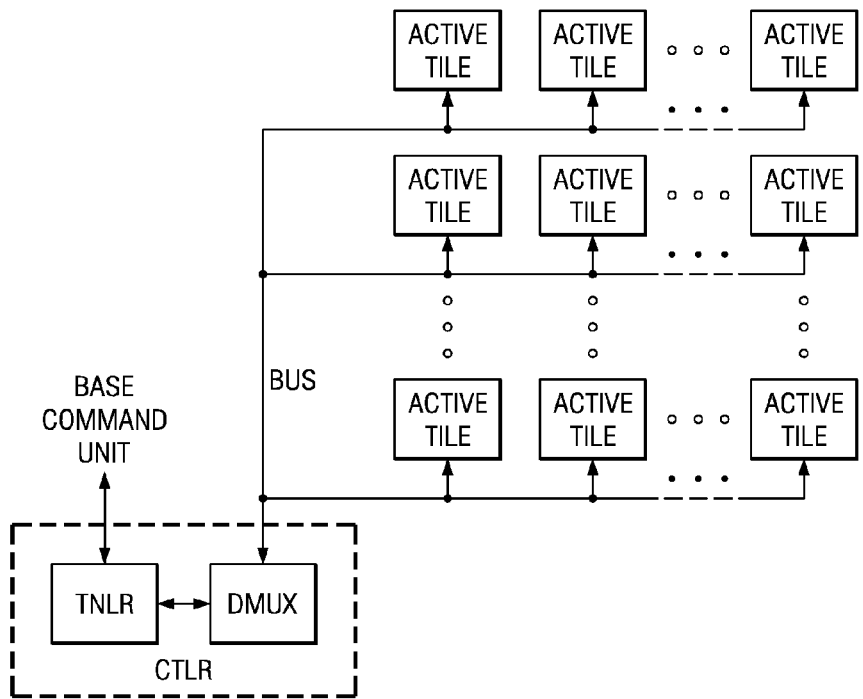
Figure 13:
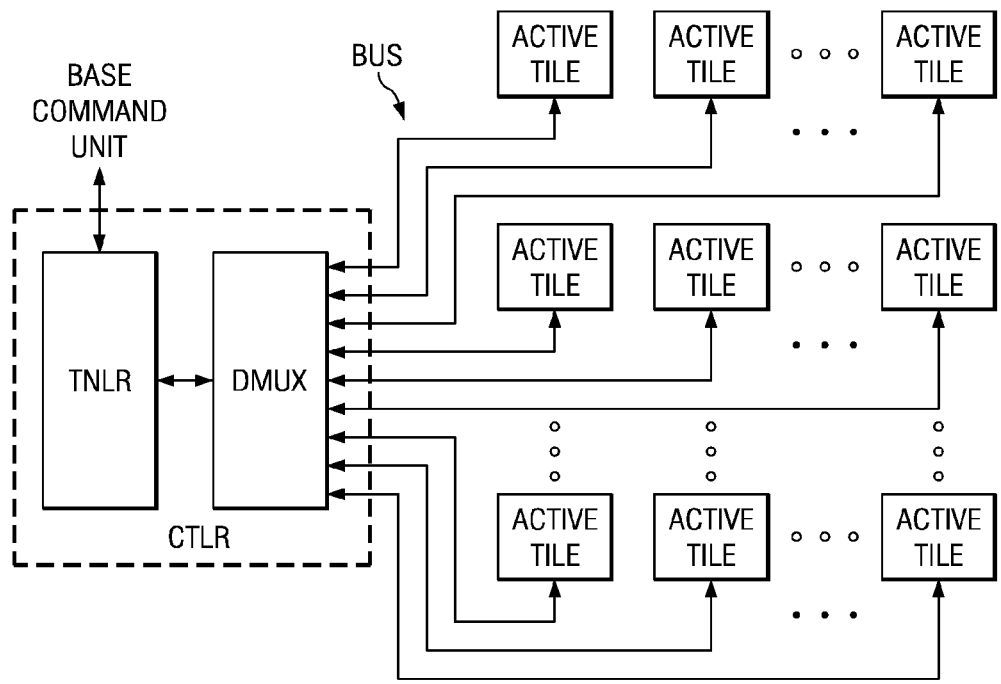

Turning now to FIG. 12, illustrated is a diagram wherein active tiles (designated "Active Tile") are individually addressable via a bus (designated "BUS"). The active tiles communicate via the bus with a controller (designated "CTLR") that includes a digital multiplexer (designated "DMUX") connected to a translator (designated "TNLR"), which communicates with a base command unit. The controller polls the active tiles to obtain the results therefrom and provides a translation for communication with the base command unit.

Figure 14:
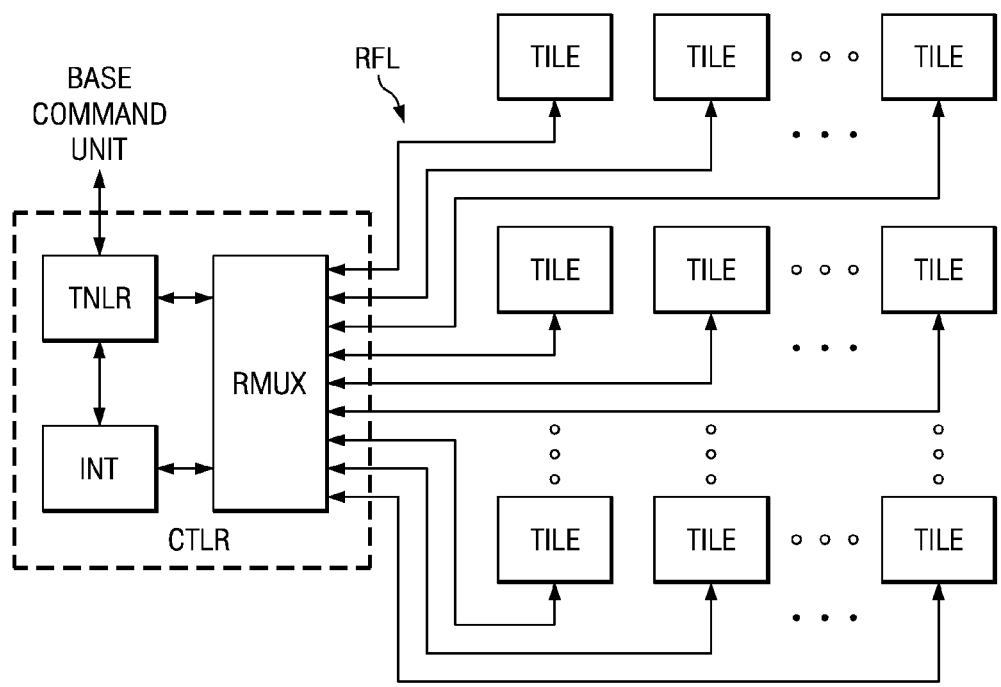

Turning now to FIG. 14, illustrated is a diagram wherein an antenna of tiles (designated "TILE") individually communicate via an RF link (one of which is designated "RFL") to an RF multiplexer (designated "RMUX") of a controller (designated "CTLR"). The controller also includes an interrogator (designated "INT") and a translator (designated "TNLR"), which communicates with a base command unit. Thus, the controller transmits/receives RF signals from the tiles, performs the interrogation function, and provides a translation for communication with the base command unit.

In addition to logging the continuous presence of an object such as an RFID object within a given area as discussed above, it is also often required to log items in at individual stations. Again, it is important to reliably perform the logging function for the desired objects while not erroneously detecting and therefore erroneously logging in any undesired objects. Therefore, what is needed is an interrogation system that reliably and easily logs in desired objects while automatically rejecting extraneous and, therefore, undesired objects that may be in the vicinity.

Figure 15:
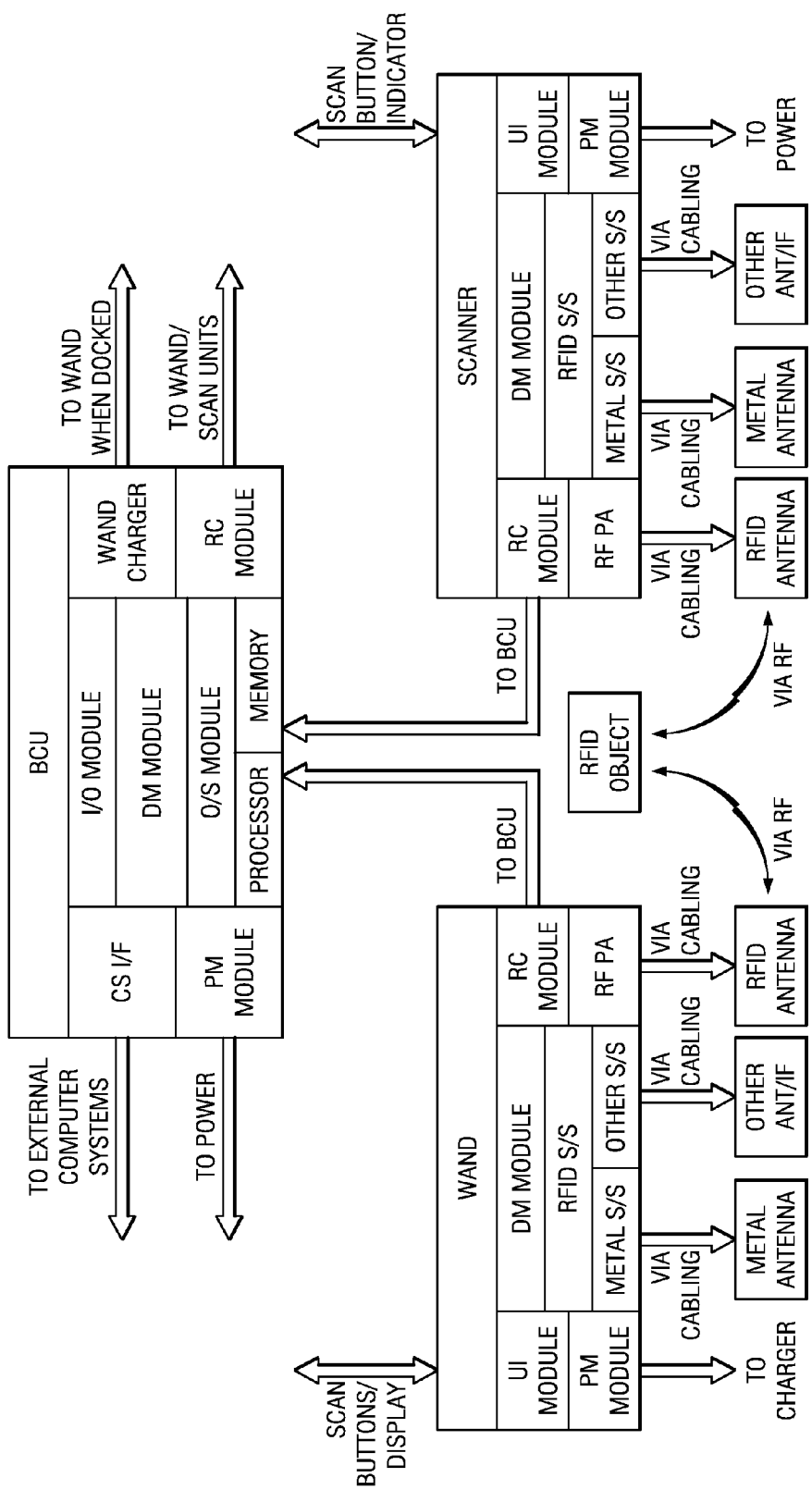
FIG. 15 illustrates a functional block diagram of an embodiment of an interrogation system constructed according to the principles of the present invention.

Turning now to FIG. 15, illustrated is a functional block diagram of an embodiment of an interrogation system constructed according to the principles of the present invention. The interrogation system includes a base command unit (designated "BCU") including an input/output module (designated "I/O module" including, without limitation, a display or monitor, keyboard, mouse and printer), a device management module (designated "DM module" including, without limitation, a user interface, accountable object management, remote scanner/detection management, fault tolerance, external interfaces, continuous diagnostics, maintenance and configuration), an operating system (designated "O/S module" such as an MS Windows operating system), a processor (designated "processor"), and memory (designated "memory" including, without limitation, a hard drive). The base command unit also includes an external computer system interface (designated "CS I/F" including, without limitation, a PCMCIA interface) to external computer systems such as, without limitation, an information technology system or supply chain management system. The base command unit also includes a power management module (designated "PM module") coupleable to an external source of power. The base command unit also includes a wand charger (designated "wand charger") coupleable to a wand when docked. The base command unit also includes a remote communications module (designated "RC module") to communicate with the wand and scan units via, for instance, bluetooth. In the illustrated embodiment, the wand unit represents a mobile interrogator and the scan unit represents a fixed interrogator.

The wand unit (designated "wand") and the scan unit (designated "scanner") include a device management module (designated "DM module") including, without limitation, device state management and configuration, maintenance interface, fault tolerance, external interfaces and continuous diagnostics. The wand and scan units also include an RFID sensing subsystem (designated "RFID S/S") coupled to an RFID antenna (designated "RFID ANT") via a radio frequency power amplifier (designated "RF PA"). The wand and scan units also include a metal sensing subsystem ("metal S/S") coupled to a metal antenna (designated "metal ANT") and another sensing subsystem ("other S/S" including, without limitation, bar code, optical, optical recognition, microelectromechanical systems, radio frequency and dot-peening) coupled to another antenna/interface (designated "other ANT/IF"). In the illustrated embodiment, the wand and scan units are detecting or scanning for an RFID object (designated "RFID object" such as, without limitation, a sponge with an RFID tag) via radio frequency ("RF") energy. Of course, an analogous principles apply for metal objects or other objects as well.

The wand and scan units also include a user interface module (designated "UI module") and a remote communications module (designated "RC module") to communicate with the base command unit. The scan unit also includes a power management module (designated "PM module") coupleable to an external source of power and the wand unit includes a power management module (designated "PM module") coupleable to a charger.

Figure 16:
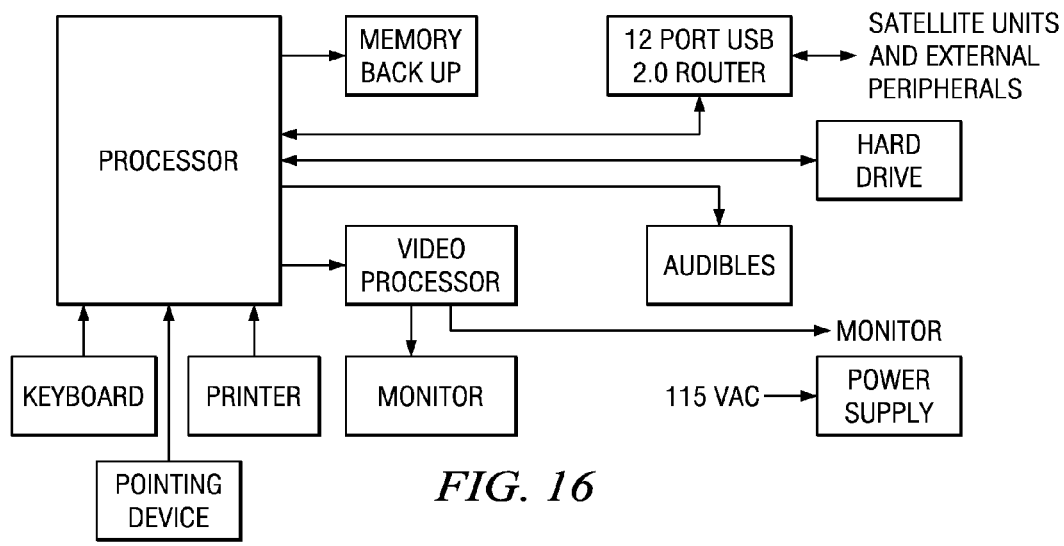
FIG. 16 illustrates a block diagram of an embodiment of a base command unit constructed according to the principles of the present invention.

Turning now to FIG. 16, illustrated is a block diagram of an embodiment of a base command unit constructed according to the principles of the present invention. The base command unit includes a processor, a video processor, memory (e.g., hard drive and memory backup), a router (e.g., a 12 port universal serial bus 2.0 router), a power supply, and input/output devices such as a monitor or display, a printer, an audible device, a keyboard and a pointing device.

Figure 17:
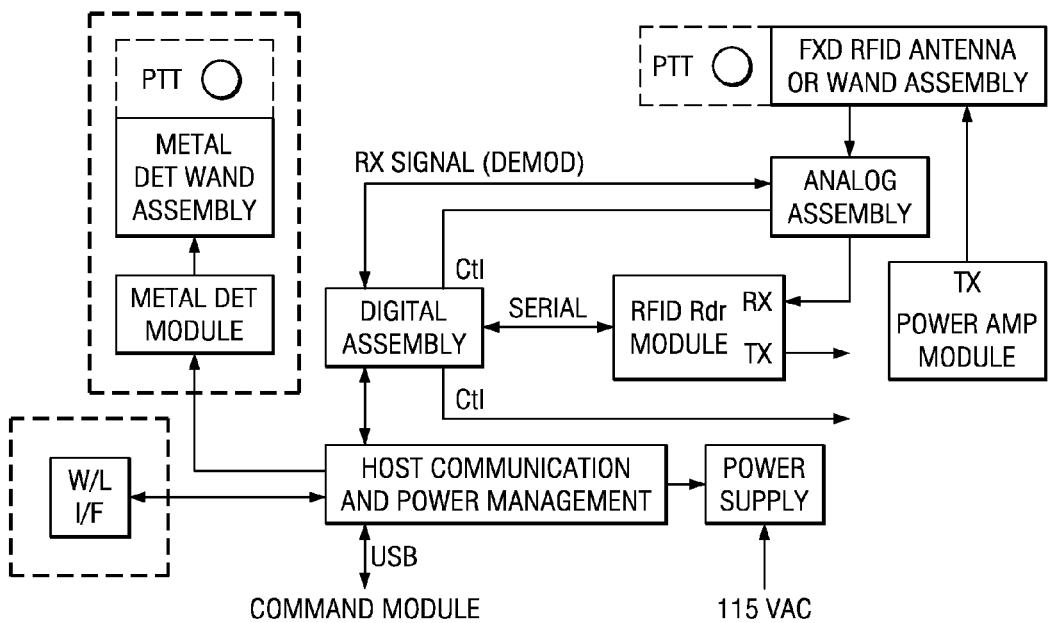
FIG. 17 illustrates a block diagram of an embodiment of an interrogator constructed according to the principles of the present invention.

Turning now to FIG. 17, illustrated is a block diagram of an embodiment of an interrogator constructed according to the principles of the present invention. The interrogator includes a metal sensing subsystem (including a metal detection wand assembly and metal detector), an RFID sensing subsystem (including an RFID reader module, fixed RFID antenna or wand assembly, power amplifier, digital and analog assemblies), a host communication and power management module, a power supply and remote communications module such as a wireless interface. While the illustrated interrogator includes RFID and metal sensing subsystems and modules, it should be understood that the interrogator may include other sensing subsystems and modules such as, without limitation, bar code, optical, optical recognition, microelectromechanical systems, radio frequency and dot-peening.

Turning now to FIGS. 18 to 28, illustrated are diagrams of exemplary antennas employable with an interrogation system constructed according to the principles of the present invention. Often in detection, an object (e.g., an RFID object) to be detected is fixed and the interrogator is scanned over an area where an RFID tag of the RFID object might be located. One approach to this problem is to simply use an existing antenna in a monostatic configuration and extend it via radio frequency ("RF") cabling so that the antenna can in effect be scanned over an area. The problem with this approach is that should the antenna be of a near field design, its range may only be on the order of a few inches and therefore render it ineffective for many applications. On the other hand, a conventional bistatic antenna using far field antennas is large and the area of detection can also be sufficiently large so as to render it useless for any detection that also requires location information. Therefore, what is needed is an antenna that both provides good location information and maintains good detection sensitivity beyond several inches.

Figure 18:
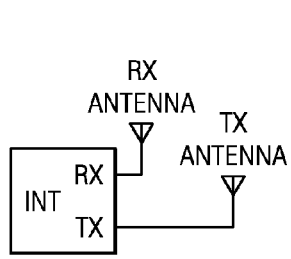

Turning now to FIG. 18, illustrated is a diagram of an RFID interrogator (designated "INT") employing a bistatic antenna configuration where a first antenna (designated "RX ANT") is connected to a receiver port (designated "RX") and a second antenna (designated "TX ANT") is connected to a transmitter port (designated "TX"). This approach allows for greater isolation between the transmitted and received signals and also allows for different antenna characteristics for the transmit and receive functions of the interrogator.

Figure 19:
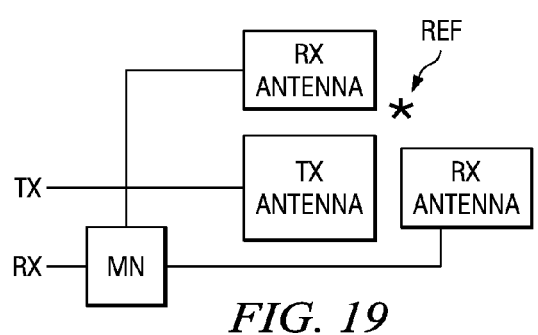

Turning now to FIG. 19, illustrated is an embodiment of a bistatic antenna configuration used with RFID interrogator specifically configured to provide both good detection sensitivity at ranges of several feet while also maintaining good location detection capability. In this embodiment, a transmit antenna (designated "TX ANT") is connected to the transmit port (designated "TX") of the interrogator and is a single antenna about which is placed two (2) receive antennas (designated "RX ANT") which are then connected to a matching network (designated "MN") and then to the receive port (designated "RX") of the interrogator. The transmit antenna and receive antennas need not be of the same type as illustrated in this embodiment. By mounting the bistatic antennas in this configuration, in addition to improved RF isolation between transmit and receive ports, the interrogator attains substantially greater capability for specifically locating the RFID object with respect to a known reference point (designated "REF") that is uniquely defined.

Turning now to FIGS. 20 to 26, illustrated are embodiments of antenna configurations constructed according to the principles of the present invention. Regarding FIGS. 20 and 21, a curved metallic structure contains a single continuous element (designated "CE"). This structure, therefore, places a much higher field strength for detection within the curved structure than without. Additionally, a mounting structure (designated "MT") such as a pole supports the antenna. Of course, other mounting structures are well within the broad scope of the present invention. As illustrated in FIG. 22, the curved metallic structure has been replaced by straight surfaces. This antenna configuration offers a more open configuration so that the object can be logged at greater distances. As illustrated in FIGS. 23 and 24, the continuous element discussed above is replaced by individual discrete elements (designated "DE") and mounted to the curved conducting surfaces. As illustrated in FIG. 25, individual discrete elements (designated "DE") are located on straight conducting surfaces.

Turning now to FIG. 26, a closed metal structure having an open top (designated "OT") and open bottom has mounted onto its inner surfaces discrete antenna elements (designated "DE"). In this manner, an object when passing through the structure shall have a higher probability of being detected due to the multiple opportunities for the RFID object to be both illuminated and read by the multiple antennas and the RF multipath generated within this relatively closed environment. This environment also provides excellent localized RFID interrogation, while at the same time not extraneously reading RFID objects in adjacent areas.

Figure 27:
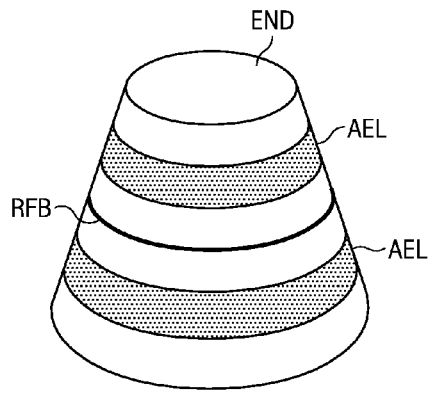
Figure 28:
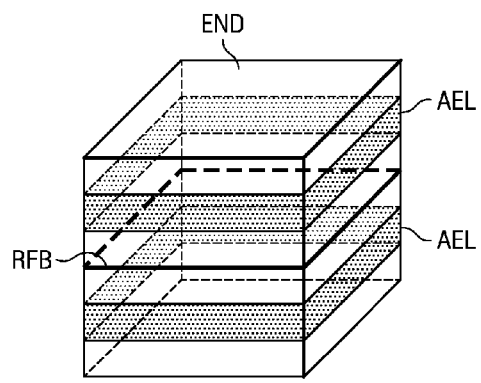

Turning now to FIGS. 27 and 28, illustrated are other embodiments of antenna configurations constructed according to the principles of the present invention. In addition to detecting an RFID object when passing therethrough, the antenna configurations may also detect a direction by which that RFID object passed therethrough. Applications of this added capability include the ability to accept or log in an object by placing the object therethrough in one direction and rejecting or logging out an object by placing the object therethrough in the opposite direction. Other applications for this added capability are comprehended herein.

Regarding FIG. 27, the antenna configuration is a generally cylindrical metallic structure open at both ends (one of which is designated "END") and includes two bands of antenna elements (designated "AEL"), which may be either continuous or discrete. Additionally, an RF barrier (designated "RFB") is also included so that radiation from one antenna element (or set thereof) does not impinge or excite the other antenna element (or set thereof). Therefore, an object passing through the structure is detected first by one antenna element and then the other at different times, defining uniquely the direction of the RFID object.

Regarding FIG. 28, the cylindrical shape discussed above is replaced by a generally square shape open at both ends (one of which is designated "END"). Here, the antenna elements (designated "AEL") also encompass the structure and are also separated by an RF barrier (designated "RFB"). It should be noted that the exemplary embodiments of the antennas introduced herein are provided for illustrative purposes only and other embodiments that include arrays for both transmit and receive antennas as well as antennas mounted in different configurations with respect to each other to achieve specific desirable properties such as that discussed above for specific applications are well within the broad scope of the present invention.

Thus, an interrogation system and method of operating the same has been introduced herein. In an aspect, the interrogation system includes an interrogator configured to detect an object at a first time and a second time, and a base command unit is configured to receive signals from the interrogator to track a location of the object, advantageously in real time. In another aspect, the interrogation system includes a first fixed interrogator, located at a first station, configured to detect an object at a first time, a second fixed interrogator, located at a second station, configured to detect the object at a second time, and a mobile interrogator, located at a third station, configured to detect the object at a third time. A base command unit of the interrogation system is configured to receive signals from the first and second fixed interrogators and the mobile interrogator to track a location of the object, advantageously in real time. The base command unit may be coupled to a display to show a location of the object and communicate with another computer system.

In a related embodiment, the object is selected from the group consisting of a radio frequency identification object, a radio frequency object, a metal object, a bar coded object, a microelectromechanical systems object, an optical recognition object and a dot-peening object. Additionally, the interrogators employ antennas selected from the group consisting of far field antennas, near field antennas, near field antenna arrays, ring antennas and bi-static antennas. In a medical environment, ones of the locations mentioned above are located in an operating room selected from the group consisting of a back table, a soiled consumable and instrument station, a dirty basin station and an operating station. In accordance therewith, the object may be a radio frequency identification object in the form of a sponge with a radio frequency identification tag.

In another related embodiment, ones of the interrogators are radio frequency identification interrogators and the object is a radio frequency identification object and the interrogation system further includes another interrogator configured to detect a different object. Thus, the base command unit can receive signals from the another interrogator to track a location of the different object. In a related embodiment, ones of the interrogators are an integrated radio frequency identification and other interrogator configured to detect a radio frequency identification object and a different object. Thus, the base command unit is configured to receive signals from the interrogator to track a location of the radio frequency identification and different objects.

In one aspect, the base command unit is a laptop computer. Additionally, the base command unit may include an input/output device, a device management module, an operating system, a processor, a memory, an external computer system interface, a power management module and a remote communications module. Also, ones of the interrogators may include a device management module, a sensing subsystem, a power management module, a remote communications module and a user interface module. In applications wherein the object is a radio frequency identification object, ones of the interrogators generate radio frequency energy in accordance with a radio frequency identification sensing subsystem and a radio frequency power amplifier to detect the radio frequency identification object. Additionally, the interrogation system may include a charger for the mobile interrogator mentioned above.

Figure 29:
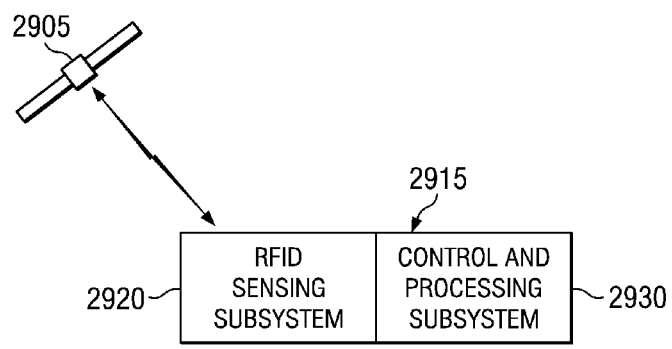
FIG. 29 illustrates a block diagram of another embodiment of an interrogation system demonstrating the capabilities associated with radio frequency identification according to the principles of the present invention.

Turning now to FIG. 29, illustrated is a block diagram of another embodiment of an interrogation system demonstrating the capabilities associated with radio frequency identification according to the principles of the present invention. The interrogation system includes an interrogator 2915 including an RFID sensing subsystem 2920 and a control and processing subsystem 2930 that energizes an RFID tag 2905 and then receives, detects and decodes the encoded RF energy (reflected or transmitted) from the RFID tag 2905. The control and processing subsystem 2930 provides overall control of the functions of the interrogator 2915 as well as any reporting functions. The interrogator 2915 may also include a user interface, communications subsystem, a power source and other subsystems as described above.

Additionally, the interrogation system may be employed with multiple RFID objects and with different types of RFID tags. For example, the RFID tags may be passive, passive with active response, and fully active. For a passive RFID tag, the transmitted energy provides a source to charge an energy storage device within the RFID tag. The stored energy is used to power a response from the RFID tag wherein a matching impedance and thereby a reflectivity of the RFID tag is altered in a coded fashion of ones ("1") and zeros ("0"). At times, the RFID tag will also contain a battery to facilitate a response therefrom. The battery can simply be used to provide power for the impedance matching/mismatching operation described above, or the RFID tag may even possess an active transmitting function and may even respond at a frequency different from a frequency of the interrogator. Any type of tag (e.g., RFID tag) whether presently available or developed in the future may be employed in conjunction with the interrogation system. Additionally, the RFID objects may include more than one RFID tag, each carrying different information (e.g., object specific or sensors reporting on the status of the object) about the RFID object. The RFID tags may also include more than one integrated circuit, each circuit including different coded information for a benefit of the interrogation system.

Figure 30:
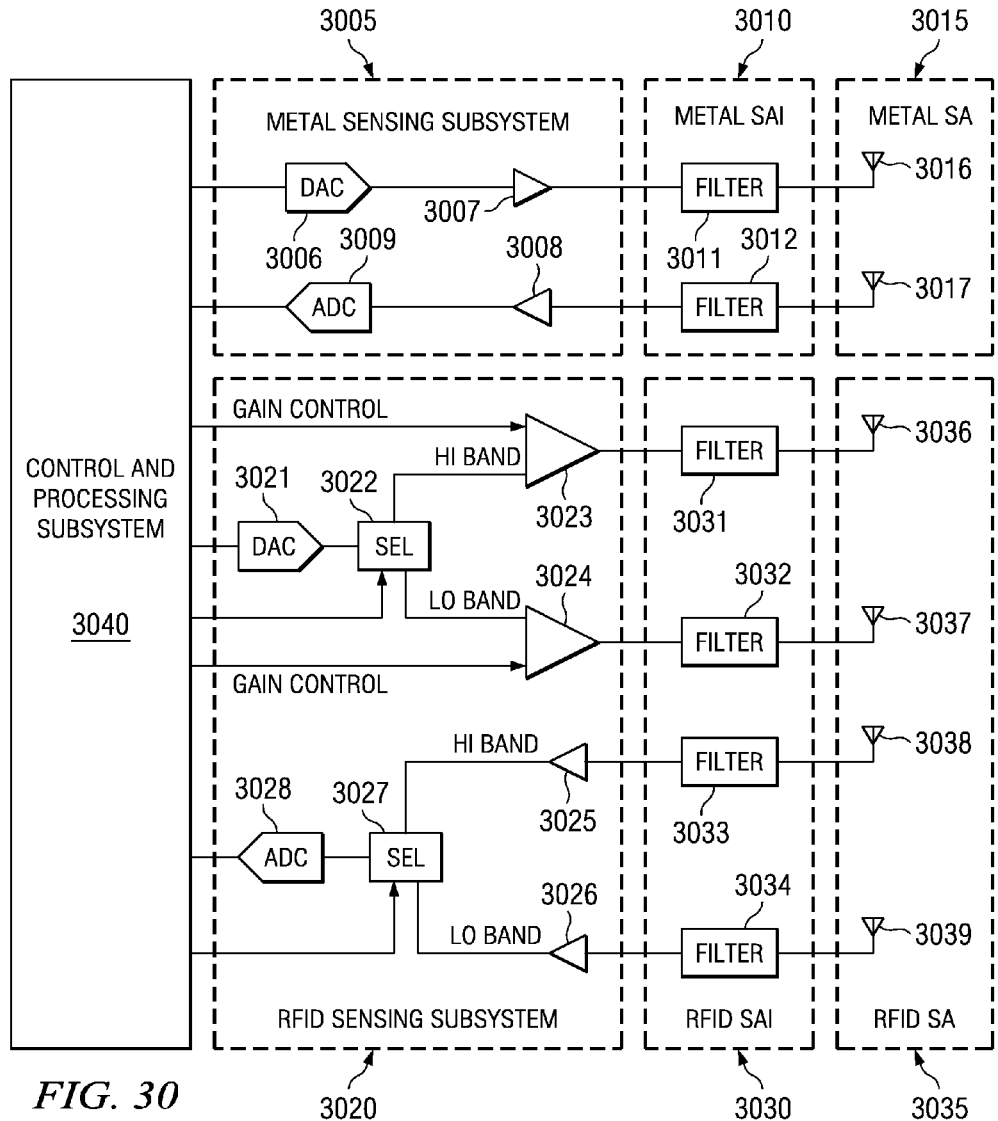
FIG. 30 illustrates a block diagram of another embodiment of an interrogator constructed in accordance with the principles of the present invention.

Referring to FIG. 30, illustrated is a block diagram of another embodiment of an interrogator constructed in accordance with the principles of the present invention. The interrogator includes a metal sensing subsystem 3005, a metal sensing antenna interface 3010, a metal sensing antenna 3015, an RFID sensing subsystem 3020, an RFID sensing antenna interface 3030, an RFID sensing antenna 3035 and a control and processing subsystem 3040. While the illustrated embodiment provides for an integrated metal and RFID detection capability, those skilled in the art should understand that portions of the interrogator may be omitted or rendered inactive to provide a metal or RFID interrogator. Additionally, different types of sensing subsystems may be incorporated into the interrogator to detect other types of objects, as well.

The metal sensing subsystem 3005 includes a metal sensing digital-to-analog converter ("DAC") 3006, a metal sensing transmit amplifier 3007, a metal sensing receive amplifier 3008 and a metal sensing analog-to-digital converter ("ADC") 3009. The metal sensing antenna interface 3010 includes a metal sensing transmit conditioning filter 3011 and a metal sensing receive conditioning filter 3012. The metal sensing antenna 3015 includes a metal sensing transmit antenna 3016 and a metal sensing receive antenna 3017.

The RFID sensing subsystem 3020 includes an RFID sensing DAC 3021, an RFID sensing transmit selector switch 3022, a first RFID sensing transmit amplifier 3023, a second RFID sensing transmit amplifier 3024, a first RFID sensing receive amplifier 3025, a second RFID sensing receive amplifier 3026, an RFID sensing receive selector switch 3027 and an RFID sensing ADC 3028. The RFID sensing antenna interface 3030 includes first and second RFID sensing transmit conditioning filters 3031, 3032 and first and second RFID sensing receive conditioning filters 3033, 3034. The RFID sensing antenna 3035 includes first and second RFID sensing transmit antennas 3036, 3037 and first and second RFID sensing receive antennas 3038, 3039. "HI band" and "LO band" capabilities are present to accommodate the wide frequency range necessary to detect the various types of RFID tags.

In an alternative embodiment, a mixing or heterodyning function may be included within the RFID sensing ADC 3028 or the RFID sensing DAC 3021 functions. These techniques are known to those skilled in the pertinent art and may be employed to translate signal processing to a more desirable frequency range thereby allowing less expensive or more readily available components to be used. Additionally, the specific nature and function of the first and second transmit conditioning filters 3031, 3032 and first and second RFID sensing receive conditioning filters 3033, 3034 may vary depending on the specific algorithms employed for control and processing and for signal generation and recovery. Also, some embodiments may not require some or all of the filters shown.

In the illustrated embodiment, the control and processing subsystem 3040 may be a software defined structure that allows features and functions of the interrogator to be easily modified or tailored by altering software functions. The control and processing subsystem 3040 employs a crystal oscillator to provide a precise frequency reference for both the metal and RFID sensing subsystems 3005, 3020.

The control and processing subsystem 3040 generates a metal sensing digital excitation signal based on a metal sensing mode of operation selected and provides this signal to the metal sensing DAC 3006. The metal sensing digital excitation signal may be in the form of a continuous tone. Alternatively, the digital excitation signal may vary in amplitude, frequency, or phase and may also be of a pulsed nature wherein the waveform duty cycle is less than 100 percent. The frequency of the metal sensing digital excitation signal may generally be in the range of five to 100 kilohertz ("kHz"). Different waveforms may be used to optimize a detection of both ferrous and non-ferrous metals. These waveforms may be selected for different sizes and masses of metals and for metals at different locations and depths within a patient. Algorithmic information employed in generating these excitation signals may be part of the control and processing subsystem 3040.

The metal sensing DAC 3006 converts the metal sensing digital excitation signal into an analog signal that, except for its amplitude, is the metal sensing transmit signal. The analog signal is provided to the metal sensing transmit amplifier 3007, which amplifies the analog signal to a correct amplitude for transmission. The output of the metal sensing transmit amplifier 3007 is provided to the metal sensing transmit conditioning filter 3011, which sufficiently attenuates all out-of-band signals and provides a proper impedance match to the metal sensing transmit antenna 3016. The metal sensing transmit antenna 3016 launches the metal sensing transmit signal.

A metal object present in the vicinity of the metal sensing transmit antenna 3016 and the metal sensing transmit signal will generate a metal sensing return signal wherein the metal sensing return signal may be based on a change in a field characteristic of the metal sensing transmit signal. The field characteristic may be altered in the vicinity of the metal object such that a distinctive metal sensing receive signal impinges on and excites the metal sensing receive antenna 3017. The output of the metal sensing receive antenna 3017 is provided to the metal sensing receive conditioning filter 3012, which sufficiently attenuates all out-of-band energy and provides a proper impedance match between the metal sensing receive antenna 3017 and the metal sensing receive amplifier 3008.

The metal sensing receive amplifier 3008 amplifies the metal sensing receive signal to a level sufficient for processing and provides it to the metal sensing ADC 3009. The metal sensing ADC 3009 provides a metal sensing digital signal, proportional to the metal sensing receive signal, to the control and processing subsystem 3040, which determines if the metal sensing digital signal has a signature representing a presence of a metal object in the vicinity of the metal sensing antenna 3015.

The control and processing subsystem 3040 generates an RFID sensing digital excitation signal based on an RFID mode of operation selected and outputs this signal to the RFID sensing DAC 3021. The RFID sensing digital excitation signal may be in the form of a code that excites and energizes an RFID object present including an RFID tag. The carrier frequency associated with this code may be in one of two frequency bands. A first frequency band may be centered around 133-135 kHz and is designated as the "LO band." A second frequency band may be centered around 10-13 megahertz ("MHz") and is designated the "HI band." Alternatively, a "HI band" around 902-928 MHz may also be employed. Alternatively, the 133-135 kHz and the 10-13 MHz bands may be combined in the "LO band" and some specific implementations may require only a single band. A frequency band is selected based on the RFID mode of operation selected. Each frequency band corresponds to different types of RFID tags present, which may be based on its size or other factors. Of course, the broad scope of the present invention is not limited to a particular frequency band. Generally, algorithmic information to generate the RFID sensing digital excitation signal is contained in the control and processing subsystem 3040.

The RFID sensing DAC 3021 converts the RFID sensing digital excitation signal into an analog signal that, except for amplitude, is the RFID sensing transmit signal. The RFID sensing transmit signal is provided to the RFID sensing transmit selector switch 3022, which is controlled by the control and processing subsystem 3040. The RFID sensing transmit selector switch 3022 directs the RFID sensing transmit signal to the first RFID sensing transmit amplifier 3023 or the second RFID sensing transmit amplifier 3024, respectively, based on whether the RFID sensing transmit signal is "HI band" or "LO band." The first RFID sensing transmit amplifier 3023 and the second RFID sensing transmit amplifier 3024 increase the amplitude of the "HI band" and "LO band" signals to a correct amplitude for transmission.

The first RFID sensing transmit amplifier 3023 provides the "HI band" signal to the first RFID sensing transmit conditioning filter 3031 and the second RFID sensing transmit amplifier 3024 provides the "LO band" signal to the second RFID sensing transmit conditioning filter 3032. The first and second RFID sensing transmit conditioning filters 3031, 3032 employ differing center frequencies and sufficiently attenuate associated out-of-band signals. Additionally, they provide a proper impedance match to their respective first or second RFID sensing transmit antennas 3036, 3037, which launch their respective RFID sensing transmit signals.

An RFID object, including an RFID tag, in the vicinity of the first or second RFID sensing transmit antenna 3036, 3037 generates an RFID sensing return signal. The RFID sensing return signal impinges on and excites the appropriate first or second RFID sensing receive antenna 3038, 3039, respectively, to provide an RFID sensing receive signal. An output of the first or second RFID sensing receive antenna 3038, 3039 is provided to the first or second RFID receive conditioning filter 3033, 3034, respectively. The first or second RFID receive conditioning filter 3033, 3034 sufficiently attenuates the out-of-band energy and provides a proper impedance match between the first or second RFID sensing receive antenna 3038, 3039 and the first or second RFID sensing receive amplifier 3025, 3026, respectively.

The first or second RFID sensing receive amplifier 3025, 3026 amplifies the small RFID sensing receive signal to a level sufficient for processing and provides an amplified RFID sensing receive signal to the RFID sensing receive selector switch 3027, which is controlled by the control and processing subsystem 3040. The control and processing subsystem 3040 selects the appropriate reception path through the RFID sensing receive selector switch 3027 for input to the RFID sensing ADC 3028, based on the excitation signal transmitted. The RFID sensing ADC 3028 provides an RFID sensing digital signal, proportional to the RFID sensing receive signal, to the control and processing subsystem 3040, which determines if the RFID sensing receive signal has a signature representing a presence of an RFID object in the vicinity of the RFID sensing antenna 3035. For an example of such an interrogator, see U.S. Pat. No. 7,019,650 (the '650 patent), entitled "Interrogator and Interrogation System Employing the Same," to Volpi, et al., issued Mar. 28, 2006, which is incorporated herein by reference.

Figure 31:
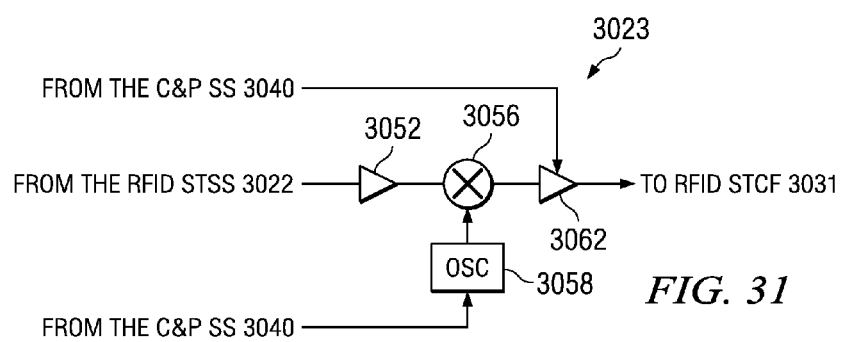
FIG. 31 illustrates a block diagram of an embodiment of portions of the RFID sensing subsystem of FIG. 30 constructed in accordance with the principles of the present invention.

Turning now to FIG. 31, illustrated is a block diagram of an embodiment of portions of the RFID sensing subsystem 3020 of FIG. 30 constructed in accordance with the principles of the present invention. For purposes of illustration, the illustrated embodiment and related description is directed to the "Hi band" signals. Of course, the principles described herein are equally applicable to the "LO band" signals. More specifically, the illustrated embodiment provides an exemplary RFID sensing transmit amplifier (e.g., the first RFID sensing transmit amplifier 3023) of the RFID sensing subsystem 3020 of FIG. 30 and will hereinafter be described with continuing reference thereto.

The first RFID sensing transmit amplifier 3023 includes first and second amplifiers 3052, 3062, a mixer 3056 and an oscillator 3058. The first amplifier 3052 (acting as a buffer and amplifier) receives a signal from the RFID sensing transmit selector switch 3022 and provides a modulated signal to the mixer 3056. The oscillator 3058 receives a control signal from the control and processing subsystem 3040 and provides a carrier signal to the mixer 3056 to set an RF carrier frequency. The control signal determines the basic RF carrier frequency that can change according to a specific air interface specification. For example, the United States ultra-high frequency ("US UHF") standard specifies a basic carrier frequency between 902 and 928 MHz. Of course, other standards and carrier frequencies are well within the broad scope of the present invention. The mixer 3056 adds the modulated signal to the carrier signal and provides a mixed signal to the second amplifier 3062. The second amplifier 3062 is a variable gain amplifier whose output signal amplitude is determined by a gain control signal from the control and processing subsystem 3040. The gain control signal sets an output power level of the signal from the second amplifier 3062. The signal from the second amplifier 3062 is provided to the first RFID sensing transmit conditioning filter 3031. The RFID sensing subsystem 3020 otherwise operates as set forth above with respect to FIG. 30. Alternatively, the modulated signal may be applied directly to an output amplifier by a gain control signal and thereby eliminate the need for the mixer 3056.

Figure 32:
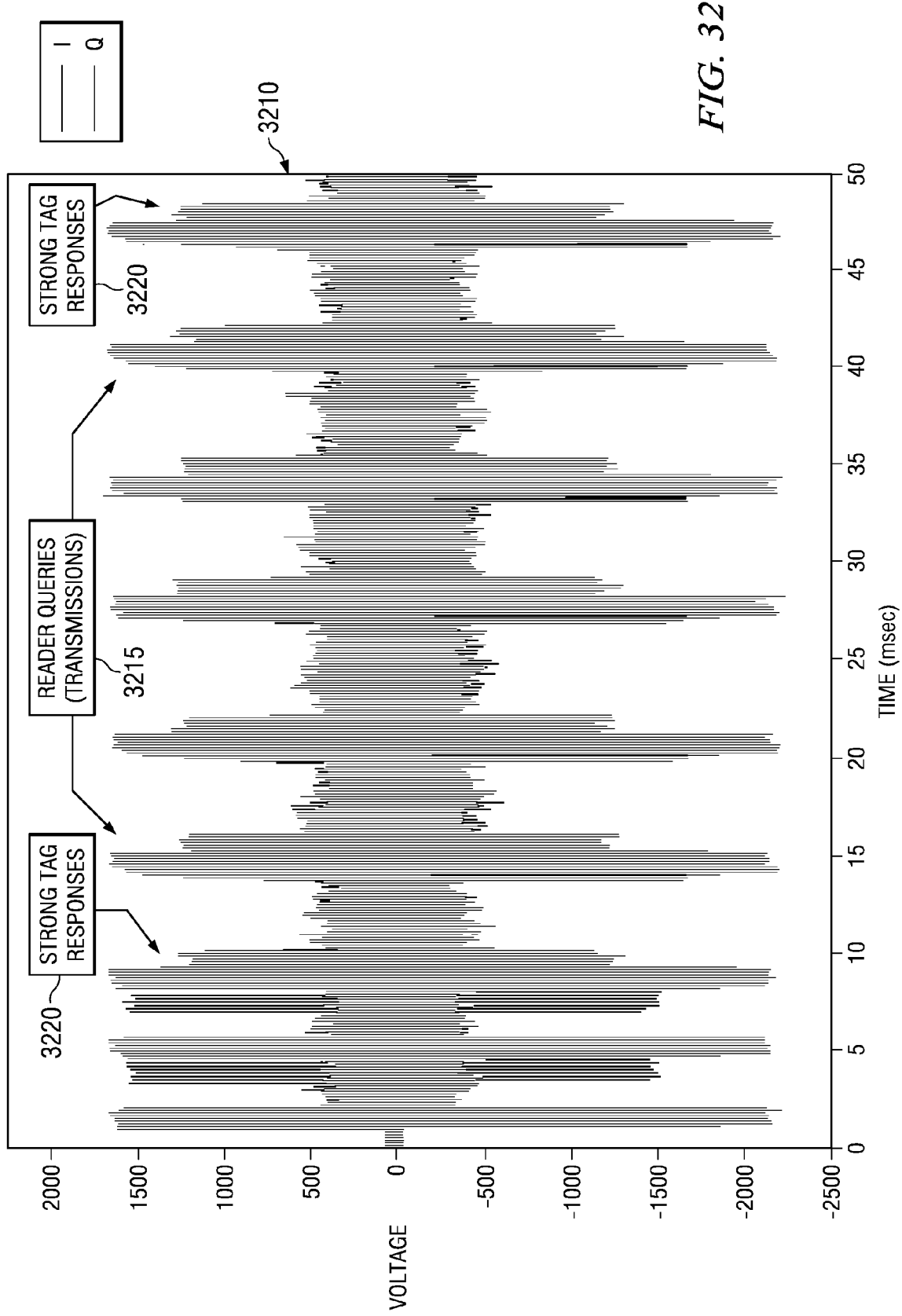
FIG. 32 illustrates a waveform diagram of an exemplary response from an RFID tag of an RFID object in accordance with the principles of the present invention.

Turning now to FIG. 32, illustrated is a waveform diagram of an exemplary response from an RFID tag of an RFID object in accordance with the principles of the present invention. The exemplary response includes recorded transmissions 3215 and backscatter return signals 3220 from the RFID tag under docile conditions. Under docile conditions, the response from the RFID tag is quite strong and substantially above the ambient noise level 3210 and an interrogator can more readily detect the response on an individual bit-by-bit basis.

Figure 33:
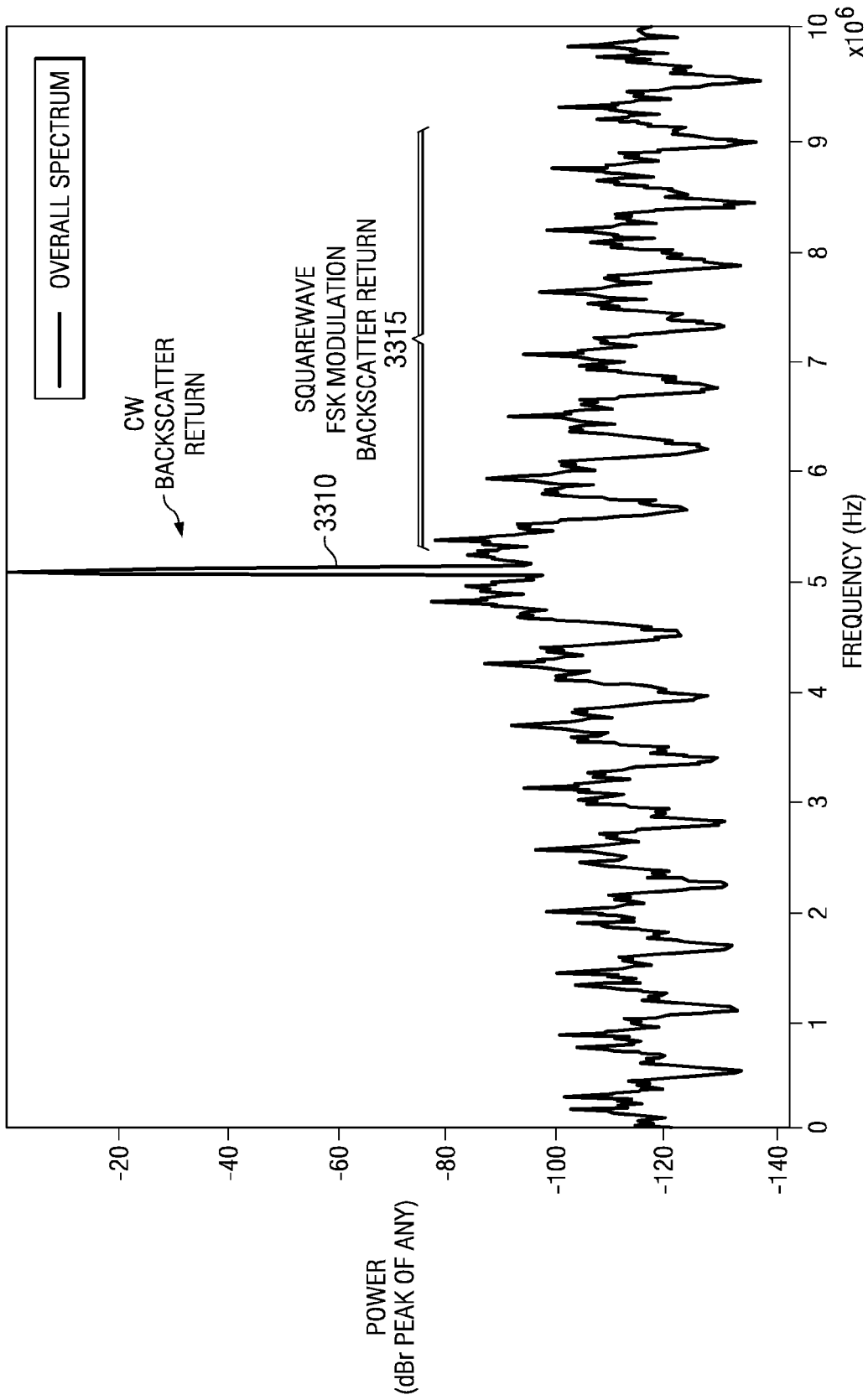
FIG. 33 illustrates a waveform diagram of a spectral response associated with the response from the RFID tag illustrated in FIG. 32.

Turning now to FIG. 33, illustrated is a waveform diagram of a spectral response associated with the response from the RFID tag illustrated in FIG. 32. As illustrated, the spectral response provides a strong signal in accordance with the response from the RFID tag under docile conditions. The signal is essentially in two distinct components. The first component is a strong backscatter return 3310, which is strongest in amplitude and at the center of the response. The second component is the lower amplitude frequency shift keying ("FSK") modulation backscatter return 3315 consisting of a series of peaks. In hostile environments or, more generally, when the response from the RFID tag is not as strong, such as when the RFID tag is located at an increased range from the interrogator or the RFID tag is obstructed from the interrogator by absorptive or reflective materials, the backscatter return signals 3315 from the RFID tag to the interrogator are substantially weakened. Consequently, the detection and identification of the RFID tag is much more difficult and an interrogator architecture that can accommodate an improved signal to noise detection capability under adverse conditions while not increasing the probability of erroneous responses would be advantageous. As will become more apparent, an interrogator and interrogation system constructed according to the principles of the present invention accommodates reliable identification of the RFID tag under docile conditions and in hostile environments.

By way of example, consider a response from an RFID tag and the existence thereof to be a one-bit message, namely, the RFID tag is either present or not. Then, the presence of the RFID tag may be a logical "1" and an absence thereof may be a logical "0," or vice versa. Then, further consider the bits of the reply code to be a spreading code for the one-bit message. Spreading codes are used in spread spectrum communications to provide additional gain from signal processing for weak signals. For a better understanding of spread spectrum technology, see an "Introduction to Spread Spectrum Communications," by Roger L. Peterson, et al., Prentice Hall Inc. (1995) and "Modern Communications and Spread Spectrum," by George R. Cooper, et al., McGraw-Hill Book Inc. (1986), both of which are incorporated herein by reference.

Further assume that a reference code [representing a reply code or portions thereof such as a tag identification ("ID") code] is preloaded into an interrogator and the reply code from the RFID tag plus any noise are correlated against the reference code by a correlation subsystem within the interrogator. If a match occurs, an increase in a gain [in decibels ("dB")] for the matched signal within the interrogator follows the relationships as set forth below:

$$\text{Gain Increase (dB)} = 10 \times \text{Log } 10(N),$$

wherein "N" is the number of bits used in the correlation.

In a numerical example, if an RFID tag with a 64 bit tag ID code is used for the correlation, then the gain would be 18.06 dB. Additionally, if an RFID tag with a 96 bit tag ID code and an eight bit preamble and 16 bit cyclic redundancy check ("CRC") is used for the correlation, then the gain would be 20.79 dB. The gain corresponds to an improvement in the signal to noise ratio ("SNR") as set forth above.

Figure 34:
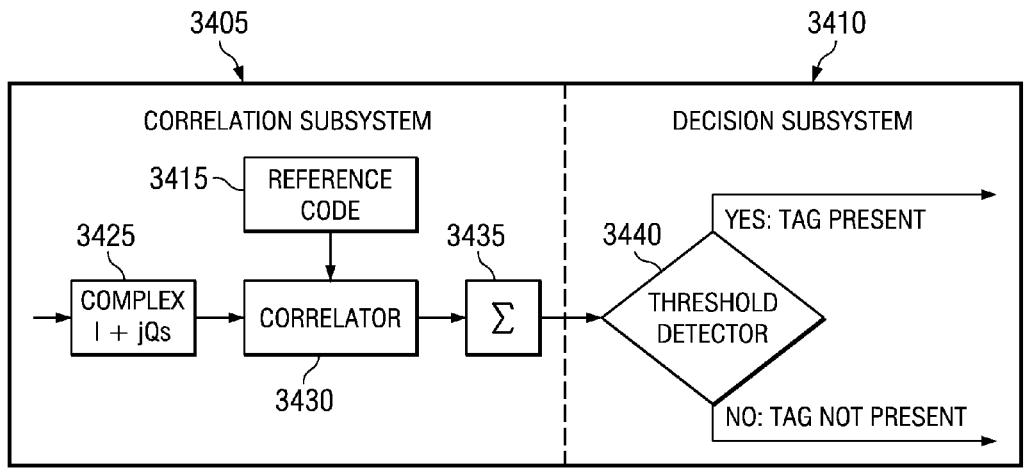
FIG. 34 illustrates a block diagram of portions of a control and processing subsystem of an interrogator constructed according to the principles of the present invention.

Turning now to FIG. 34, illustrated is a block diagram of portions of a control and processing subsystem of an interrogator constructed according to the principles of the present invention. The control and processing subsystem includes a correlation subsystem 3405 and a decision subsystem 3410. While in the illustrated embodiment the correlation subsystem and the decision subsystem form a portion of the control and processing subsystem such as within a digital signal processor thereof, those skilled in the art should understand that the subsystems may be discrete subsystems of the control and processing subsystem of the interrogator or located in other locations of an interrogation system.

The interrogator may employ a correlation operation to correlate between reference codes (generally designated 3415) corresponding to reply codes (generally designated 3425) from the RFID tags of RFID objects and subsequently received and digitized reply codes from the RFID tags to enhance a sensitivity of the interrogator. The reply codes are typically generated as complex I+jQ signals, where I signifies the in phase portion of the signal and Q signifies its quadrature counterpart. The reference codes may be scanned in during the initialization stage or derived synthetically as hereinafter described. To derive the reference code synthetically, the amplitude, phase and delay (e.g., timing of a response to an excitation signal) information of a particular type of RFID tag may be employed by the interrogator to derive the synthetic reference code. The correlation occurs in a correlator 3430 wherein the reply code is correlated (e.g., compared or matched) with the reference code during a post-initialization stage of operation. The correlation is mathematically analogous to a convolution operation. For a better understanding of convolution theory, see "An Introduction to Statistical Communication Theory," by John B. Thomas, published by John Wiley & Sons, Inc. (1969), which is incorporated herein by reference.

A stream of incoming data in the form of a response to the interrogator (e.g., corresponding to responses in the form of reply codes from the RFID tags) is correlated against preloaded reference codes loaded into a reference code database in time. Alternatively, samples of the incoming data may be gated in a block by the interrogator and then the data is correlated in block manner against the reference codes. In the latter example, a gating process is employed to gate the incoming data properly. Under such circumstances, apriori knowledge of a timing of the responses from the RFID tag in connection with a query by the interrogator better serves the process of gating the block of incoming data (e.g., the responses) from the RFID tags. Any known delay in the responses from the RFID tags can be preloaded in the interrogator during the initialization stage. An external sensor such as a position sensor (e.g., inertial sensor) may be employed by the interrogator to aid the correlation subsystem in predicting the timing of a response from the RFID tag. A synchronization pulse (e.g., derived from the transmit excitation signal) may also be employed to better define a timing of a response from an RFID tag.

The output of the correlator 3430 representing individual correlations of the reference code with incoming data is summed in a summer 3435 providing a correlation signal to improve the signal to noise ratio of the correlated signal. The correlation signal from the summer 3435 is typically input into a threshold detector 3440 within the decision subsystem 3410 to verify a presence of an RFID tag. The threshold detector 3440 typically compares the correlation signal with at least one threshold criteria or value (also referred to as threshold). The threshold may be fixed or dynamically determined. In one exemplary embodiment, where only a single threshold is present, an RFID tag is declared present if the correlation signal from the summer 3435 exceeds the threshold, and not present if the converse is true. In other embodiments, multiple thresholds may be used to indicate various levels of probabilities as to the likelihood that an RFID tag is present or not. This information may then be used to initiate selected or additional search modes so as to reduce remaining ambiguities.

Regarding the timing of the responses from the RFID tag, a tracking of the reply codes may suggest that the reply code is early, prompt or late. If the tracking suggests that the reply code is prompt (prompt output greater than early and later output), then a gating function is properly aligned to provide a significant correlator output. If the tracking suggests that the reply code is early, then the early correlator output is significant as compared to the late correlator output and the correlation subsystem 3405 is tracking too early and the requisite adjustment may be performed. An opposite adjustment may be performed if the tracking suggests that the reply code is late.

Another approach is to use a tracking loop that uses past successful detection performance to establish a gating process for subsequent correlations. In yet another embodiment relating to the correlation of the reply codes from the RFID tags is to perform Fast Fourier Transforms ("FFTs") on both the reference code and a gated sample of the reply codes from the RFID tags. Then, a convolution operation in "Fourier Space" may be performed employing the convolution theorem. The convolution theorem states that the convolution of two functions is the product of the Fourier transforms thereof. An output of the correlation operation is typically envelope detected and several outputs may be averaged in a summing operation that preserves time characteristics of each individual detection. For an example of such a control and processing subsystem, see U.S. Publication No. 2005/0201450 (the "450 Publication), entitled "Interrogator and Interrogation System Employing the Same," to Volpi, et al., filed Mar. 3, 2005, which is incorporated herein by reference.

Figure 35:
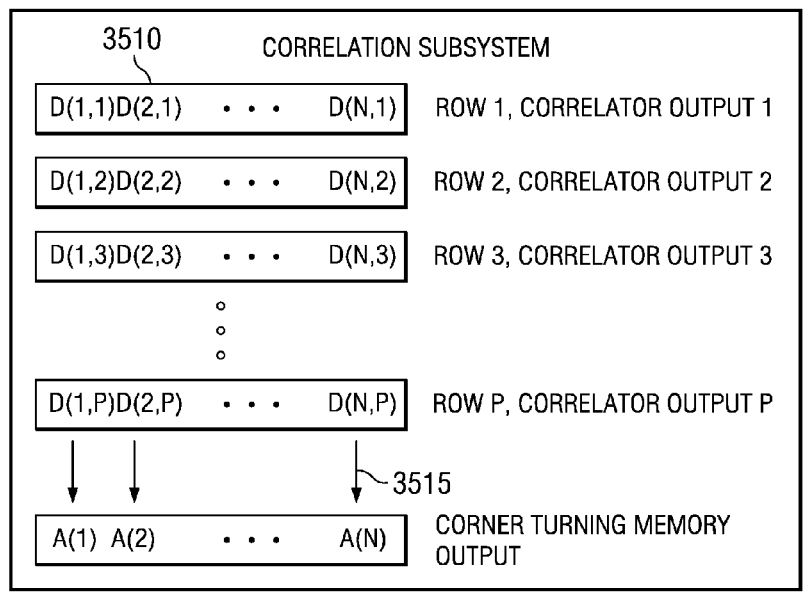
FIG. 35 illustrates a block diagram of an embodiment of portions of a correlation subsystem associated with a control and processing subsystem of an interrogator demonstrating an exemplary operation thereof in accordance with the principles of the present invention.

Turning now to FIG. 35, illustrated is a block diagram of an embodiment of portions of a correlation subsystem associated with a control and processing subsystem of an interrogator demonstrating an exemplary operation thereof in accordance with the principles of the present invention. In the present embodiment, a technique referred to as a "corner turning memory" is used in accordance with the correlation subsystem allowing a summing and averaging process for multiple correlations. An output of a correlator is read into memory by rows (one of which is designated 3510) with each row designating a single correlation. Then an output from the summing process (which embodies the memory or a function thereof) is generated by summing across individual columns (generally designated 3515, hence the name corner turning) applying an appropriate scaling factor. An output from the memory represents an average of "P" outputs of the correlation subsystem wherein "P" is the number of rows in the corner turning memory. Assuming a signal is located in every row of the corner turning memory, the improvement in signal to noise ratio ("SNR") is increased by the square root of "P."

Using this approach, several options for enhancing performance of the interrogator are possible. For example, the results of different averaging times can be almost simultaneously compared and the modes of operation of the interrogator adjusted for enhanced performance. Also, this approach allows the sliding average technique (as described above) to be employed so that the output from the memory is an average over a predetermined period of time. Also, other averaging techniques in addition to the use of the corner turning memory are well within the broad scope of the present invention.

Figure 36:
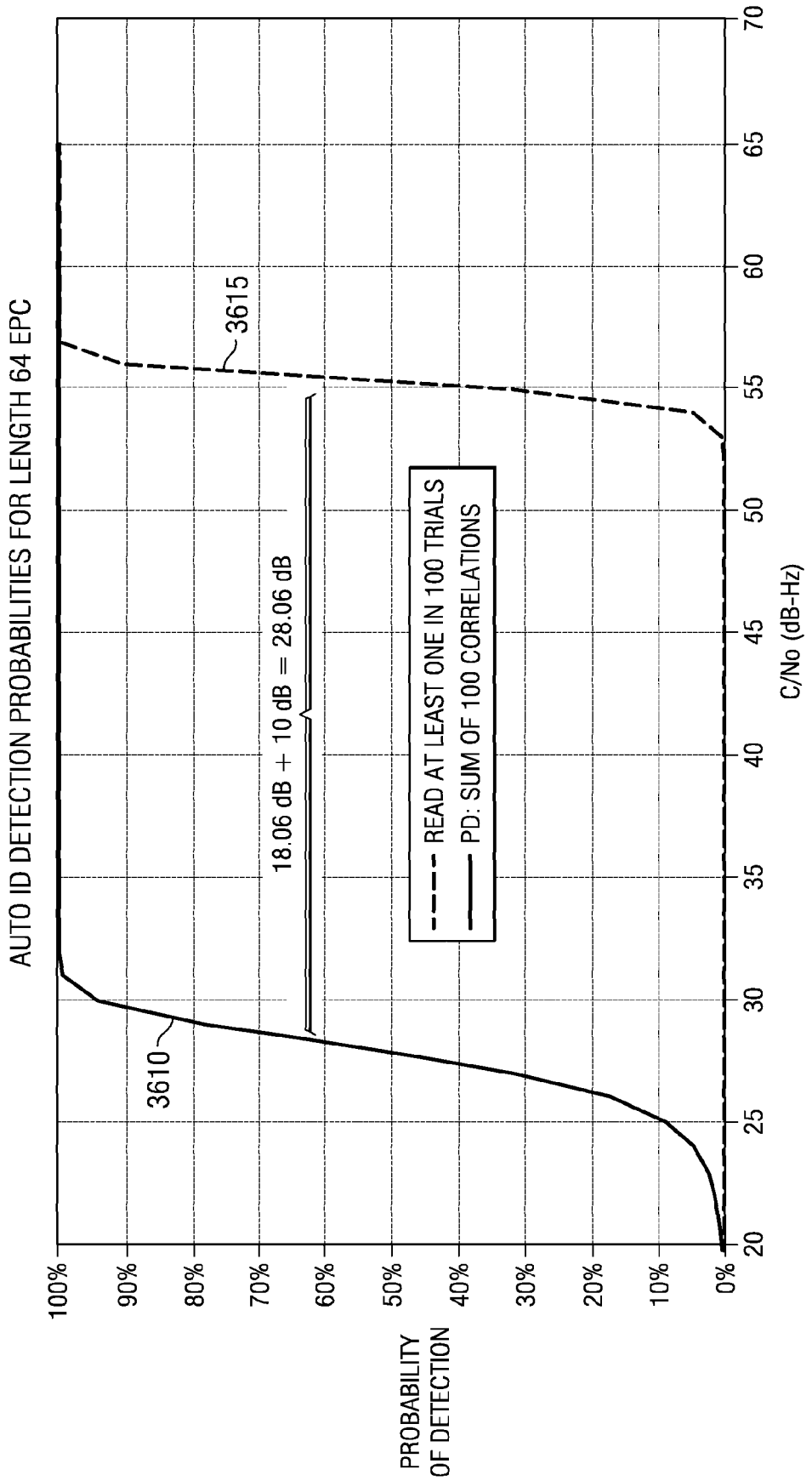
FIG. 36 illustrates a waveform diagram demonstrating exemplary advantages associated with the correlation subsystem described with respect to FIGS. 34 and 35.

Turning now to FIG. 36, illustrated is a waveform diagram demonstrating exemplary advantages associated with the correlation subsystem described with respect to FIGS. 34 and 35. In the illustrated embodiment, a conventional waveform 3615 represents the probability of detection for a given carrier to noise ratio ("C/No") of a conventional reader reading at least one out of 100 possible attempts. A total of 100 trials were averaged in accordance with the correlation subsystem and an improved waveform 3610 represents the increased probability of detection for a given C/No of an interrogator thereby demonstrating an improvement in SNR of 28.06 dB. This represents 18.06 dB due to correlation operation wherein a length 64 electronic product code ("EPC") code was used, plus an additional 10 dB due to non-coherent averaging. A purpose of the correlation operation is to determine whether or not the output or averaged output of the interrogator represents a presence of an RFID tag. A threshold detector as herein described then interprets a correlation signal from the correlation subsystem and provides a decision if the output is of sufficient quality to indicate if an RFID tag is present or not and, if indeterminate, to perform a "deeper" or more "focused" search.

Figure 37:
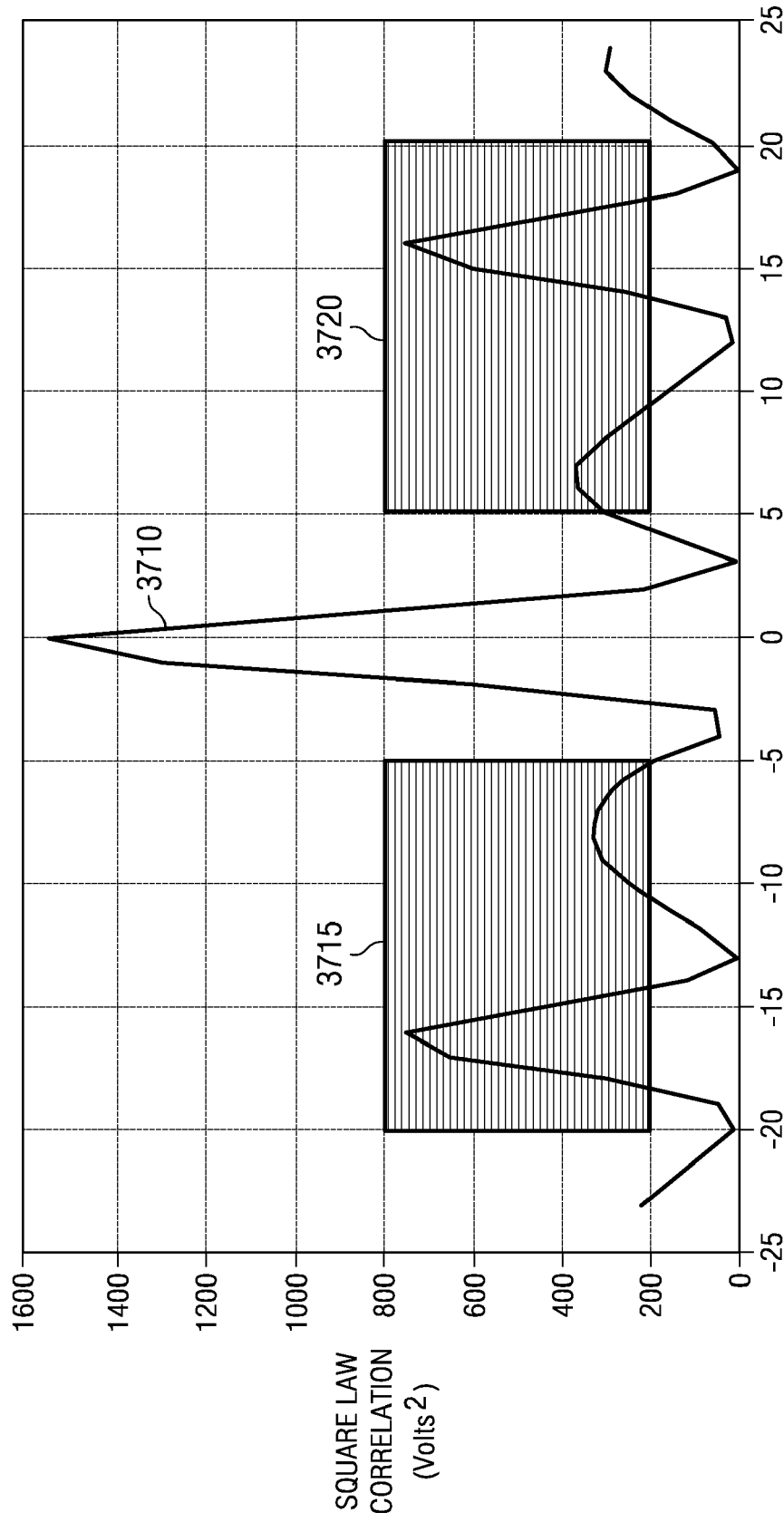
FIG. 37 illustrates a waveform diagram demonstrating the sidelobes associated with the correlation subsystem in accordance with the principles of the present invention.

Turning now to FIG. 37, illustrated is a waveform diagram demonstrating the sidelobes associated with the correlation subsystem in accordance with the principles of the present invention. Understanding the nature of the sidelobes and using their characteristics within a predetecting function can enhance the correlation subsystem of the interrogator. As illustrated, the correlation includes a major peak 3710 (referred to as "prompt") and two smaller peaks (generally referred to as "early" 3715 and "late" 3720) about the major peak. By averaging the noise in the early and late regions and comparing those values to noise levels recorded when it was known that no signal was present, additional confirmation is obtained that, in fact, an RFID tag is responding even if the RFID tag is not uniquely identifiable in a single response at the present signal levels. Then, by averaging multiple responses that correspond to RFID tag responses, the SNR will be raised to a level wherein substantially unambiguous detection occurs.

In this instance, the reply code of an RFID tag is not being detected, but the interrogator is detecting a change in ambient noise that substantially increases the probability that an RFID tag is indeed present. For example, sampling in all three regions and having the noise level be the same is a good indication that an RFID tag is not present and therefore that the sample should be discarded. However, sampling in all three areas and finding that the early and late levels are about equal and the middle level is larger is a good indication that a response from an RFID tag is in fact present and that this sample should be added into the averaging function. Clearly discarding samples that do not pass the early/late noise test will certainly discard data of actual RFID tags. That is a small price to pay, however, for not unduly corrupting the average with samples that do not in fact contain a reply code from an RFID tag. Sampling for slightly longer times compensates for the reduction in samples used. The control and processing subsystem can maintain a running total of how many samples were discarded so that the number of samples averaged will remain valid.

Regarding the timing of the responses from the RFID tag, a tracking of the reply codes may suggest that the reply code is early, prompt or late. If the tracking suggests that the reply code is prompt (prompt output greater than early and late output), then a gating function is properly aligned to provide a significant correlator output. If the tracking suggests that the reply code is early, then the early correlator output is significant as compared to the late correlator output and the correlation subsystem is tracking too early and the requisite adjustment may be performed. An opposite adjustment may be performed if the tracking suggests that the reply code is late.

Another approach is to use a tracking loop that uses past successful detection performance to establish a gating process for subsequent correlations. In yet another embodiment relating to the correlation of the reply codes from the RFID tags, FFTs are performed on both the reference code and a gated sample of the reply codes from the RFID tags. Then, a convolution operation in "Fourier Space" may be performed employing the convolution theorem. The convolution theorem states that the convolution of two functions is the product of the Fourier transforms thereof. An output of the correlation operation is typically envelope detected and several outputs may be averaged in a summing operation that preserves time characteristics of each individual detection.

Figure 38:
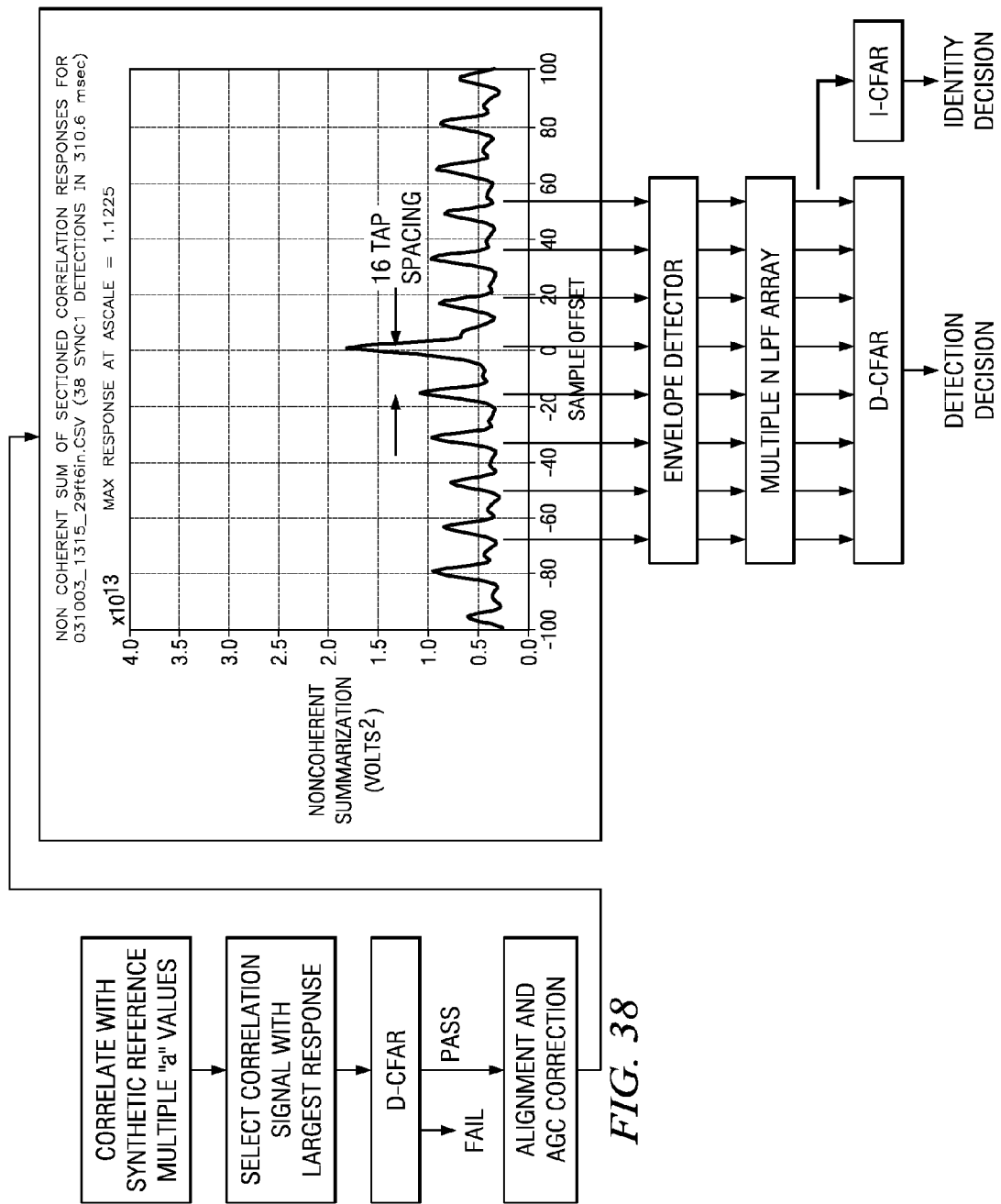
FIG. 38 illustrates a block diagram of portions of an embodiment of a control and processing subsystem of an interrogator constructed according to the principles of the present invention.

Turning now to FIG. 38, illustrated is a block diagram of portions of an embodiment of a control and processing subsystem of an interrogator constructed according to the principles of the present invention. The correlation subsystem of the control and processing subsystem correlates using multiple "a" values and then selects a correlation signal yielding the largest correlation value. The resultant is then run through an initial constant false alarm rate ("CFAR") subsystem whose principle function is to decide whether an RFID tag of an RFID object has fired. Additionally, it is advantageous to filter out burst interference signals from the correlation signals. The correlation signals that pass the initial detection ("D-CFAR") subsystem then enter a decision subsystem.

The next step is to align the correlation signals so the maximum response lag is at lag 0. An automatic gain control ("AGC") correction is also applied wherein the signal is normalized to have a peak power of one (at lag 0) and then the other lags are normalized by the same constant. This has the effect of making the correlation signals have the same weight in the subsequent steps.

The correlation signals are then envelope detected when employing noncoherent multiple tag response integration. The result is passed into an array of low pass filters ("LPF"). Finally, the LPF filter outputs are fed into a final detection CFAR ("D-CFAR") subsystem that makes the final decision as to whether the RFID tag is present and an identification CFAR ("I-CFAR") subsystem that decides if the right RFID tag is present, given a detection from the final D-CFAR subsystem.

Figure 39:
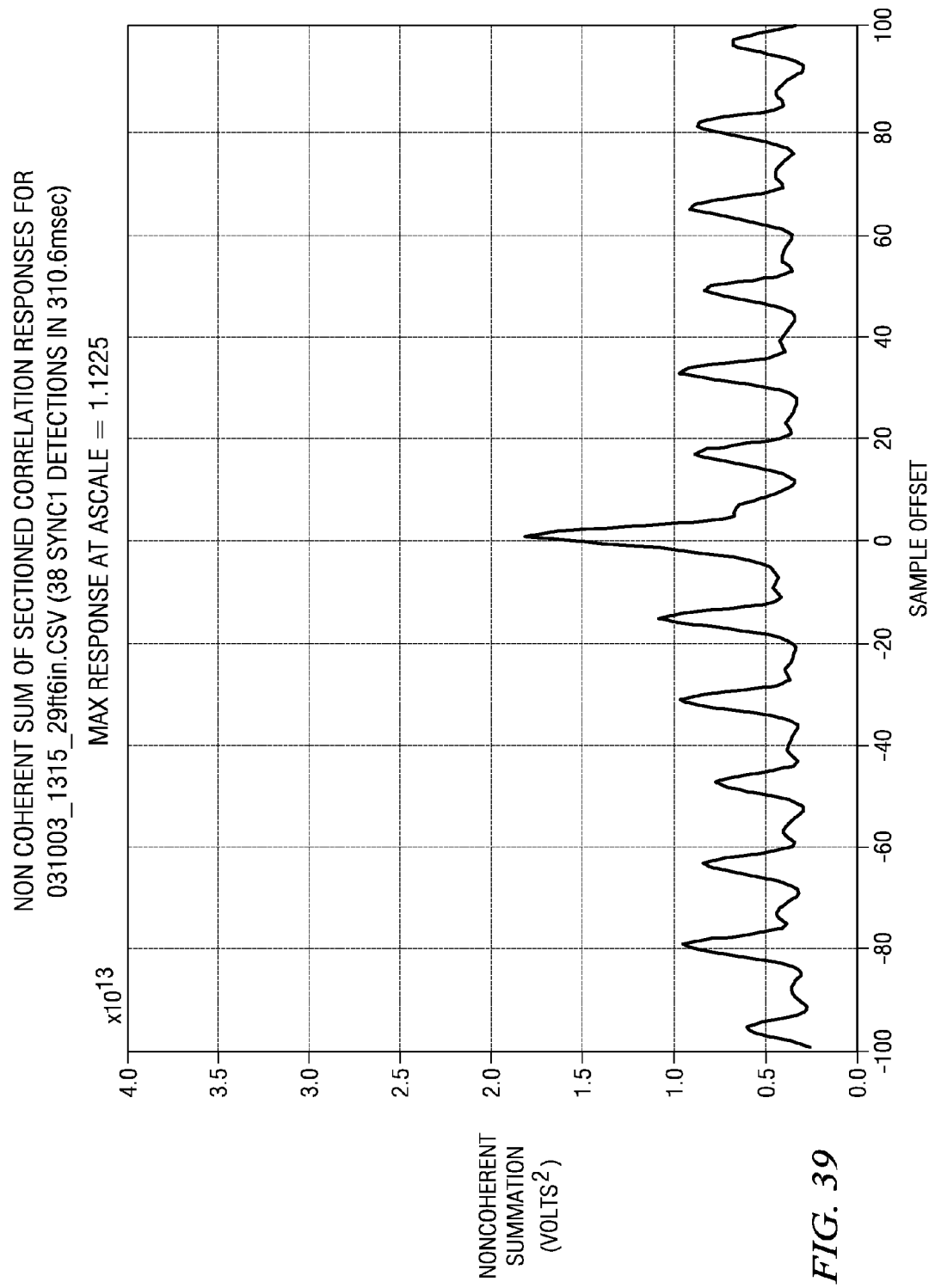
FIG. 39 illustrates a waveform diagram demonstrating an application of a cell averaging constant false alarm rate with an interrogator according to the principles of the present invention.

Turning now to FIG. 39, illustrated is a waveform diagram demonstrating an application of a cell averaging constant false alarm rate with an interrogator according to the principles of the present invention. More particularly, the waveform diagram demonstrates an application of a cell averaging CFAR to RFID detection wherein an analog to digital sample timing is setup to produce 16 samples per bit. The temporal sidelobe structure seen is a consequence of the frequency shift keying ("FSK") backscatter modulation used in autoID tags. Absent a strong correlation response, the central spike will not be seen.

A basic idea of the cell averaging CFAR is to average responses at lag values of $\{-64,-48,-32,-16, 16, 32, 48, 64\}$ with respect to the central 0 lag point and use this as a threshold for testing the central lag for signal presence. In CFAR parlance, the central cell is called the cell under test ("CUT"). The average of the cells used to obtain the threshold is called the cell average ("CA").

Figure 40:
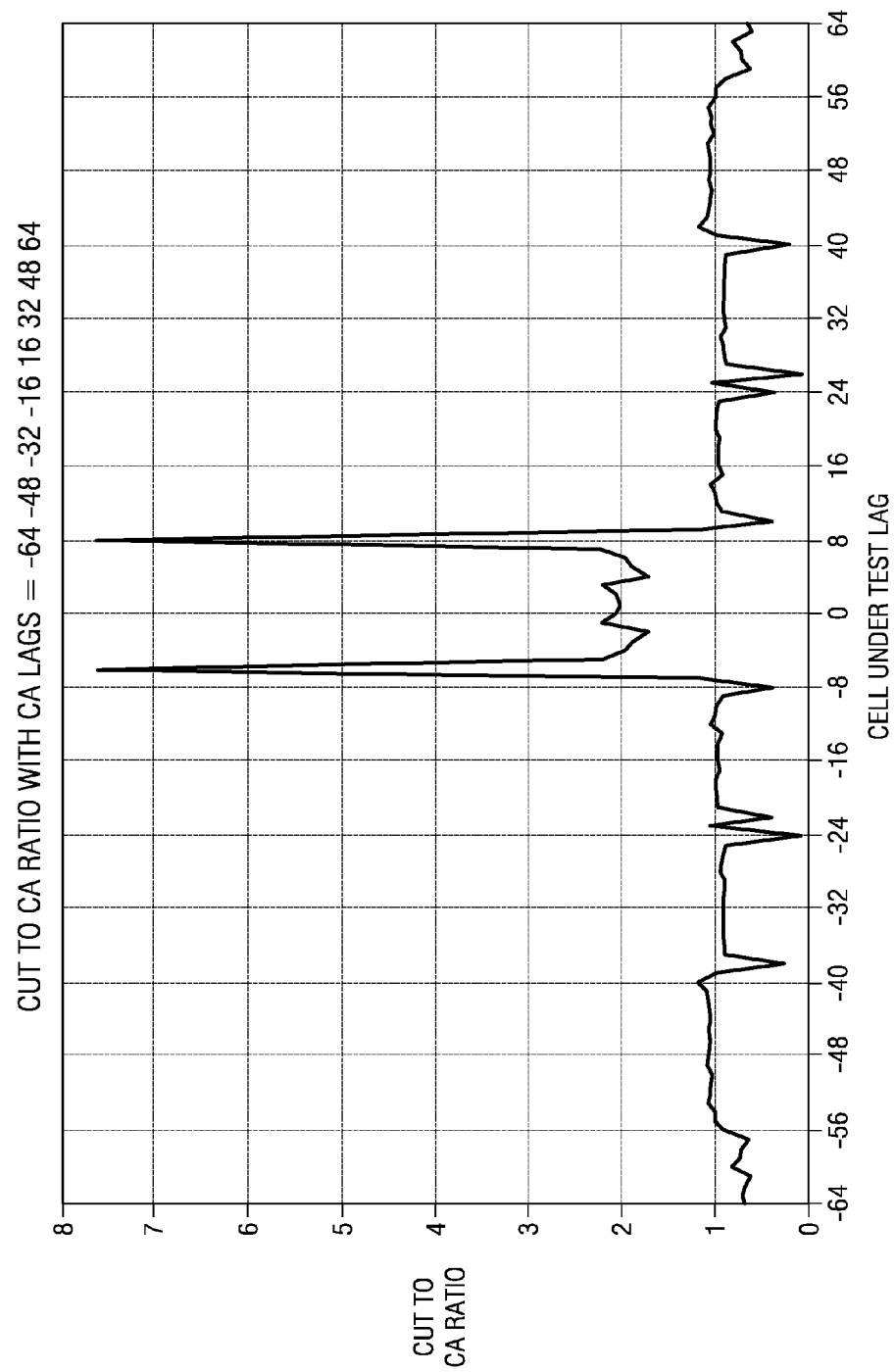
FIG. 40 illustrates a waveform diagram of a cell under test to a cell average ratio as a function of a cell under test lag using an unfiltered reference in accordance with a constant false alarm rate in accordance with the principles of the present invention.

Turning now to FIG. 40, illustrated is a waveform diagram of a cell under test to a cell average ratio as a function of a cell under test lag using an unfiltered reference in accordance with a constant false alarm rate in accordance with the principles of the present invention. Clearly, the ratio increases in the neighborhood of the central peak. The big ears at −6 & 8 lags are an artifact of the test signal used being unfiltered and will tend to disappear with real signals. The above D-CFAR subsystem decides whether an RFID tag is present.

Figure 41:
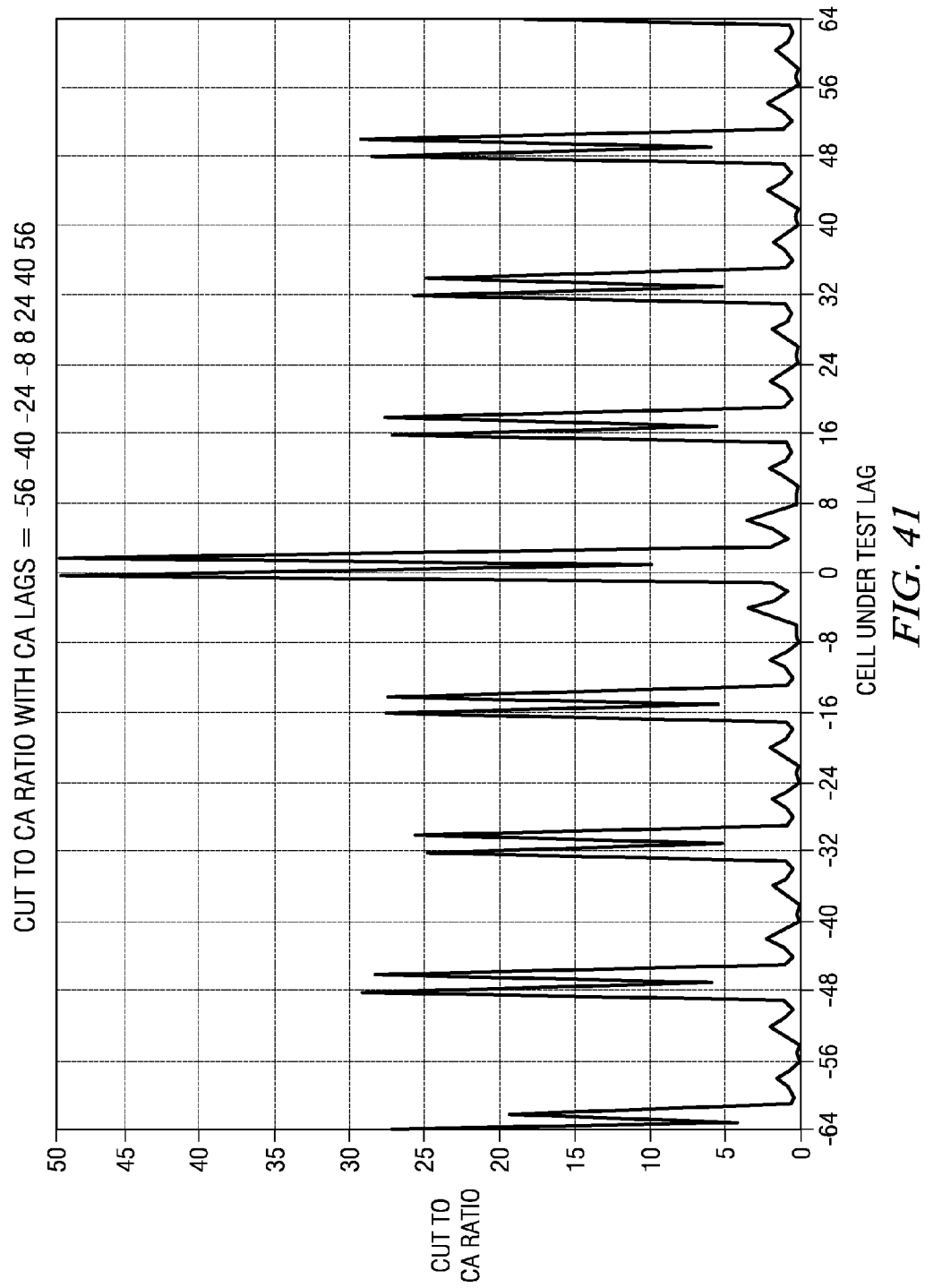
FIG. 41 illustrates a waveform diagram of a cell under test to a cell average ratio for another constant false alarm rate in accordance with the principles of the present invention.

Turning now to FIG. 41, illustrated is a waveform diagram of a cell under test to a cell average ratio for another constant false alarm rate in accordance with the principles of the present invention. In the illustrated embodiment, the current average lags are $\{-56, -40, -24, -8, 8, 24, 40, 56\}$. These lags yield small correlation values when the signal is present and so act more like a noise level reference. Again, this D-CFAR subsystem decides whether an RFID tag is present.

With continuing reference to FIG. 38, as gain is made larger; the threshold is higher and thus the noise is rejected more effectively. This lowers the probability of false alarm, but it also lowers probability of detection in the presence of the desired signal. The initial D-CFAR subsystem has a gain setup so that the correlation signal passes, even if it is pretty weak, but at the cost of increased false alarm rates. Occasionally, the correlation signal will pass in noise. The final D-CFAR subsystem has had the benefit of some filtering from the LPF array and so has its gain value tuned to a larger value so as to have a low false alarm rate. When it declares a detection, the I-CFAR subsystem declares the right RFID tag.

As mentioned above, a corner turning memory is an important element in building up SNR for weak signal detection purposes. Once the corner turning memory is filled, an integrate and dump "filter" averages the contents of each column of the corner turning memory and the resultant vector is presented to a CFAR subsystem for a detection decision as described above. FIG. 42 illustrates an integrate and dump filter and its statistical properties. In the alternative, the integrate & dump filter can be replaced by a low pass filter as illustrated with respect to FIG. 43. The "1-A" multiplication provides a filter with unity DC gain.

From a noise perspective, the two approaches are statistically equivalent if:

$$A = \frac{N-1}{N+1}, \text{ and}$$

| N | Equivalent A |
|---|---|
| 1 | 0.000000 |
| 3 | 0.500000 |
| 10 | 0.818182 |
| 30 | 0.935484 |
| 100 | 0.980198 |

The low pass filter approach has the advantage that it weights more recent samples more heavily and gradually "forgets" about the older samples. To see this aspect, note how once a sample is inside the filter it re-circulates around the loop, each time being multiplied by A. After K iterations, the input value has been attenuated by a factor $A^K$.

Figure 44:
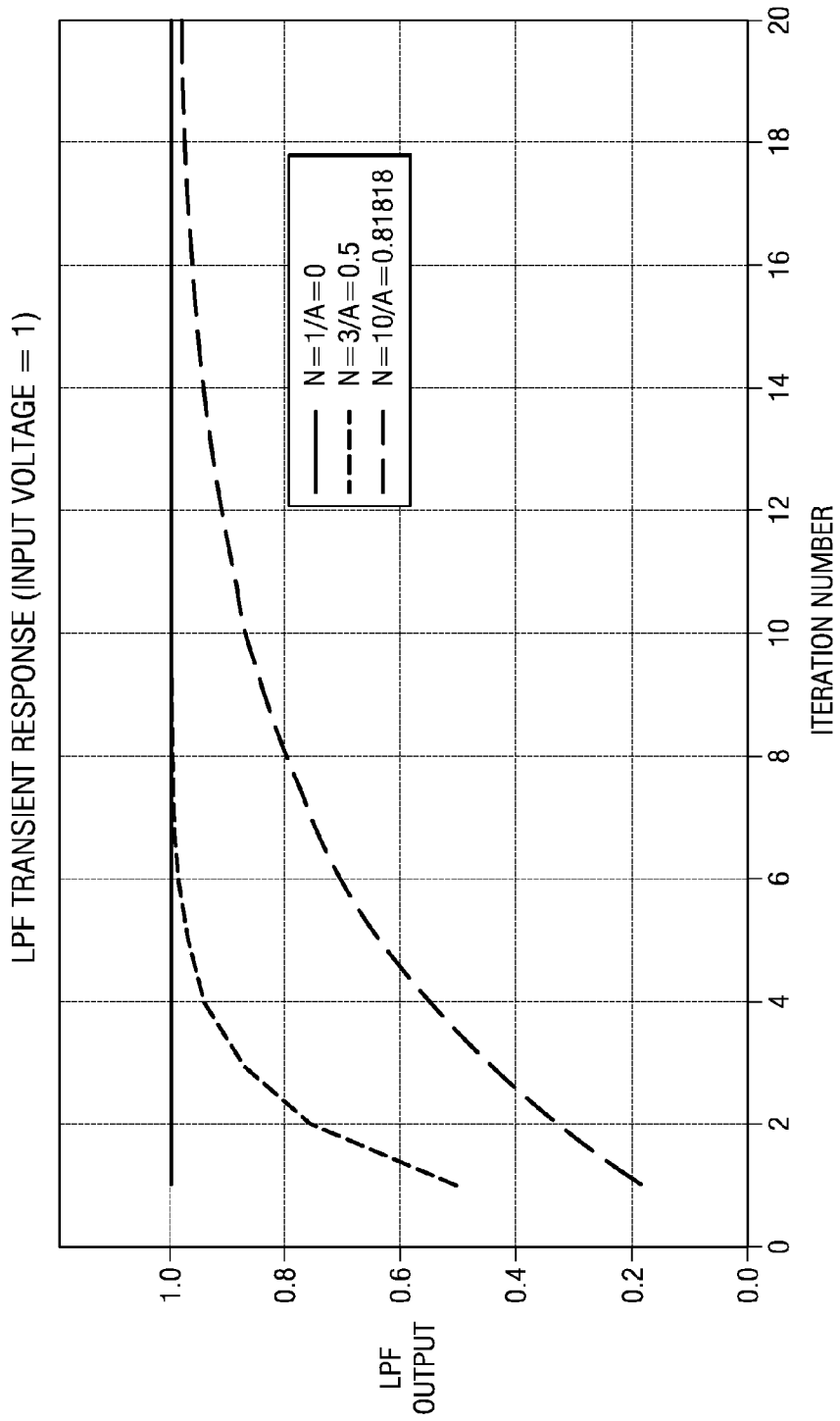
FIG. 44 illustrates a waveform diagram of a response from a low pass filter employable with a control and processing subsystem of an interrogator constructed according to the principles of the present invention.

As a corollary to this, the low pass filter also has a charging time, prior to which, insufficient averaging has taken place. FIG. 44 illustrates low pass filter transient responses for three different "N" values. As N increases, the filter becomes more sluggish in its response because it is, in effect, averaging more samples. As a rule of thumb, the filter should be charged with N samples before accepting its output as valid.

Inasmuch as the interrogator may be moving when detecting an RFID tag of an RFID object, multiple time constant filters may be employed to advantage. The short time constant filters (small N) would have faster response, but less sensitivity, while longer time constant filters (larger N) would respond slowly to weak RFID tag responses, but would eventually respond. Each bank of filters (e.g., three banks having a time constant) would be followed by a CFAR subsystem and should provide a unique output to an operator.

Turning now to FIG. 45, illustrated is an embodiment of a filter structure for supporting multiple channels, with an indication of how it relates to the D-CFARs and I-CFAR subsystems. Of particular note, once alignment has occurred (see, e.g., alignment and AGC correction in FIG. 38), extraneous cells that do not contribute to the decision process may be discarded. Also, the lag structure is based on a presumption that the analog to digital sample rates are tied to nominal 16 samples per data bit. Again, it is preferable that the filter first be charged with N samples before using its output to drive the CFAR subsystems. If throughput is an issue, the inputs of the low pass filters can be operated in series with decimation and yield essentially the same performance. Similarly, the medium and slow channel CFAR subsystems may not be run every time a correlation signal passes the initial CFAR tests. Now that exemplary control and processing systems and subsystems and interrogation systems have been introduced, various systems and methodologies will be introduced to enhance a sensitivity of the interrogator and the interrogation systems.

It would be advantageous to the interrogation system to increase the effective reading range in free space, and increase the ability to read RFID tags of an RFID object when an attenuating object is interposed between the RFID tag and the interrogator, of both passive and semi-active RFID tags, by an approach to power management of the transmitted signals from the interrogator. The system of power management works with all interrogators, and is especially effective when used in conjunction with interrogators employing correlators or correlation subsystems.

As an example, an interrogator can control the transmitted RF signal such that the amplitude of the signal may be varied under control of the interrogator. The interrogator may increase the amplitude of any or all portions of the RFID tag interrogation sequence to deliver increased energy to the RFID tag to control the amount of energy delivered to the RFID tag before interrogation (e.g., allowing the RFID tag to store energy to be used during its response, also called "precharging"), during interrogation, or during the RFID tag's response to interrogation. In so doing, the interrogator increases (e.g., maximizes) RFID tag detectability while at the same time reducing (e.g., minimizing) the average amplitude of radiated energy.

In another aspect, an interrogator increases the time of unmodulated (also known as "continuous wave") signal used to provide the energy to initially activate the RFID tag from the minimum specified by standards applicable to the specific class of RFID tag being used. Current industry practice is to reduce the period of continuous wave transmission to near the minimum required for standards compliance in order to facilitate the rapid reading of RFID tags. The ability to extend the duration of the initial continuous wave period allows more time for the RFID tag to accumulate energy for activation and backscatter response. Additionally, an initial pilot tone return of the RFID tag can also be detected and aid in locating the presence of an RFID tag in weak signal conditions as provided above, even if the response is too weak to be completed or detected.

In another aspect, an interrogator allows precharging of the RFID tag to occur by sending a sequence of messages, with no intervening time delay, to which the RFID tag cannot respond, followed immediately by an interrogation command (e.g., a single interrogation command). The initial sequence of messages will result in a relatively long period in which energy is presented to the RFID tag while the RFID tag is not required to expend energy to respond, resulting in energy accumulation within the RFID tag. The single interrogation command that follows causes the RFID tag to expend the energy in a single response.

Thus, the interrogator is managing power in an intelligent way in order to get more performance out of the interrogation system while still maintaining full standards compatibility with whatever type of RFID tag is used and while still being fully compliant with any and all maximum transmit power specifications so long as those specifications are defined over times that are long with respect to a single interrogation/reply sequence. For a better understanding of RFID tags, see "Technical Report 860 MHz-930 MHz Class I Radio Frequency Identification Tag Radio Frequency & Logical Communication Interface Specification Candidate Recommendation," Version 1.0.1, November 2002, promulgated by the Auto-ID Center, Massachusetts Institute of Technology, 77 Massachusetts Avenue, Bldg 3-449, Cambridge, Mass. 02139-4307, and "EPC Radio-Frequency Identity Protocols Class-1 Generation 2-2 UHF RFID Protocol for Communications at 860-960 MHz," Version 1.09, January 2005, promulgated by EPC-global Inc., Princeton Pike Corporate Center, 1009 Lenox Drive, Suite 202, Lawrenceville, N.J. 08648, which are incorporated herein by reference.

A protocol independent interrogation system (e.g. an RFID interrogation system) is described that includes at least one RFID excitation source, typically embodied in a transmit function, and a corresponding RFID receive function. The transmit and receive functions may be employed in an interrogator that includes control and processing subsystems and sensing subsystems embodied in a software defined architecture wherein a significant portion of the signal processing is done in the digital domain after an incoming signal plus any associated noise has been appropriately digitized. The interrogator can deliver power to the RFID tag to permit the RFID tag to fully or partially respond to excitation under conditions of attenuation of the transmitter signal that preclude operation of presently available readers. This enhanced ability to excite the RFID tag has applications in both extending the useful detection range for RFID tags in free space, and in detecting RFID tags when signal attenuating objects are present between the RFID tag and the interrogator.

Figure 46:
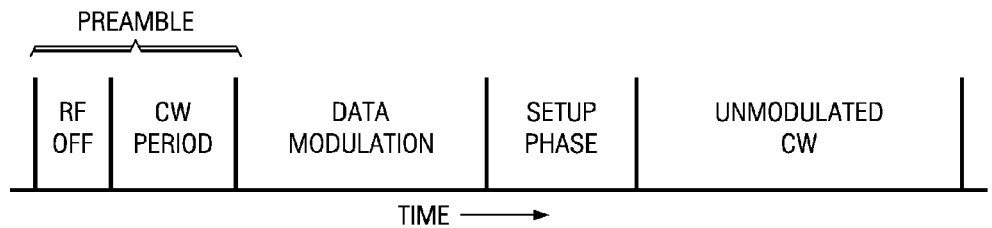
FIGS. 46 and 47 illustrate diagrams of an interrogation sequence in accordance with an interrogator.
Figure 47:
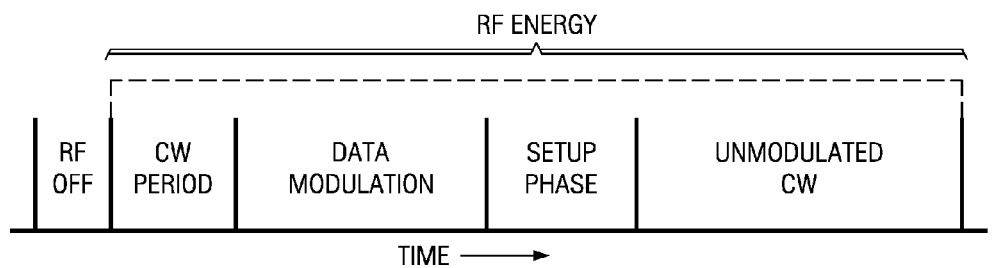

Turning now to FIGS. 46 and 47, illustrated are diagrams of an interrogation sequence in accordance with an interrogator. The interrogation sequence contains a period in which no energy is transmitted (designated "RF OFF"), followed by a period in which an unmodulated or continuous wave message ("CW") is transmitted (designated "CW Period"), followed by known message patterns wherein modulation is added for use by a receiving RFID tag to first synchronize a clock of the RFID tag with the interrogator (designated "Data Modulation"), followed by the message content and message integrity control information (e.g., checksums or cyclic redundancy check codes, designated "Setup Phase"). Upon completion of the transmitted command, the interrogator continues to send continuous wave energy as an unmodulated CW message (designated "Unmodulated CW"). It is this energy that is then modulated via impedance matching/mismatching (also known as "backscatter") by the RFID tag. The interrogator then detects this modulated energy, and decodes the information sent by the RFID tag.

The duration of the initial no-transmission and continuous wave periods (collectively known as the "preamble") each typically have minimum durations defined by applicable standards. Due to the requirements mentioned above of typically being able to read an RFID tag as quickly as possible, and also of reading as many RFID tags within a given time period as possible, current commercial practice is to maintain both the no-transmission and continuous wave periods near the minimums specified by the standards. The interrogation system as provided herein may make use of increasing the aforementioned time periods to achieve greater sensitivity in detecting the presence of RFID tags.

As illustrated in FIG. 47, an interrogator is attempting to detect a passive (no onboard power) RFID tag. The region designated "RF Energy" illustrates that portion of the timeline when RF energy is being transmitted by the interrogator. Often a situation exists when significant signal attenuation may exist between the interrogator and the RFID tag so that the energy necessary to activate the RFID tag is insufficient or the energy reflected back to the interrogator is beyond the sensitivity thereof causing an RFID tag to be undetected. This attenuation may be due to a large distance in free space between the interrogator and the RFID tag, or may be due to an adverse environment providing significant attenuating characteristics.

In either case, under these conditions, the total energy received by the RFID tag during the continuous wave message period (designated "CW Period") of the preamble may be insufficient to adequately charge the RFID tag and allow the RFID tag to even begin to operate or, correspondingly, the RFID tag may have sufficient energy to begin operation, but be unable to complete its transmission because of insufficient energy. Experience with RFID tags has determined that energy requirements necessary to modulate the signal, by impedance matching/mismatching, are relatively high as compared to the energy requirements for the RFID tag's onboard processor to operate. Thus, there exists a range of conditions in which sufficient energy is available for the RFID tag to begin transmission, but not complete the transmission and fully respond during the unmodulated CW period (designated "Unmodulated CW"). The result is system failure as regards to detecting and identifying that RFID tag.

Figure 48:
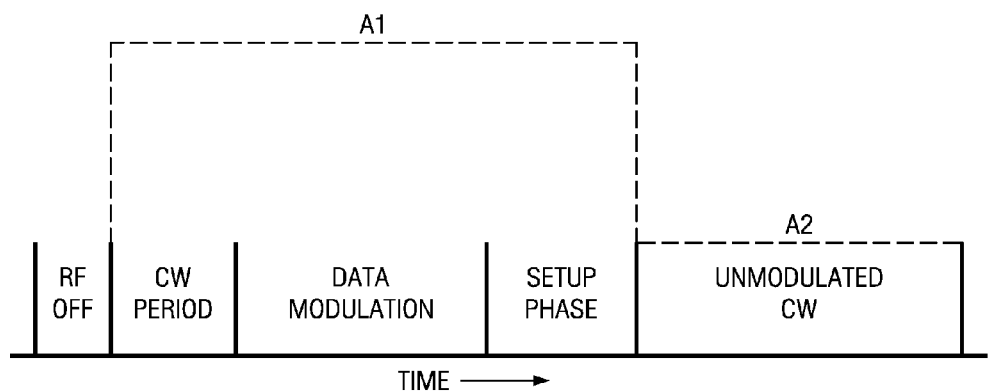
FIG. 48 illustrates an embodiment of an interrogation sequence in accordance with an interrogator constructed according to the principles of the present invention.

Turning now to FIG. 48, illustrated is an embodiment of an interrogation sequence in accordance with an interrogator constructed according to the principles of the present invention, which will increase the energy available to the RFID tag via a method referred to as "precharging." In this case, the period of the continuous wave message (designated "CW Period") in the preamble has been extended as compared to the interval used in current commercial practices. For example, the period of the continuous wave message may be extended by at least one millisecond. Based upon experience with RFID tags, it has been observed that the RFID tags exhibit the ability to accumulate energy over a period of time. The interrogation sequence shown extends the period of continuous wave transmission, allowing additional time for the RFID tag to accumulate enough energy to power itself, begin transmission and possibly to complete the transmission. As described earlier, even a partial transmission may be useful in some instances.

Additionally, as illustrated in FIG. 48, the average amplitude also varies with time with the periods representing the continuous wave message (designated "CW Period"), the data modulation message (designated "Data Modulation") and the setup phase message (designated "Setup Phase") having a larger average amplitude (designated "A1") than the period representing the unmodulated CW period (designated "Unmodulated CW") with an average amplitude (designated "A2"). In so doing, additional energy is incident on the RFID tag, increasing the likelihood of the RFID tag having adequate energy to decode the modulated data from an interrogator and then respond during the period associated with the unmodulated CW message. By reducing the power, the average power over the entire process is also reduced. An interrogator such as that described in the '450 Publication due to its increased sensitivity would be able to read the modulated reflected energy from the RFID tag during the interrogator's unmodulated CW transmission. This regime is, by definition, of relatively short duration, thereby allowing the interrogator to comply with aggregate power emission limitations.

Alternatively, it is not necessary to reduce the power and maintain the increased level throughout the entire process. Additional embodiments consisting of various other combinations of high and low power periods to augment RFID tag precharging while maintaining low average power are comprehended within the context of this invention.

Yet another embodiment for precharge capability according to the principles of the present invention is to send, as rapidly as possible, a series of messages within the interrogation sequence that the RFID tag cannot respond to, followed immediately by an interrogation command. This method results in a situation wherein the RFID tag has an extended opportunity to accumulate energy prior to being required to transmit, although it is not as effective as the extended continuous wave method described above due to the periods of no transmission contained within the preambles on each of the individual messages. The advantage of this method is that it is easily implemented on many existing interrogators.

Thus, a sensing subsystem of the interrogator transmits an unmodulated continuous wave message and detects a modulated version of the continuous wave message from the RFID tag. A control and processing subsystem of the interrogator discerns a presence of the RFID tag from the modulated version of the continuous wave message and decodes information from the RFID tag. The sensing subsystem is configured to vary instantaneous power of an excitation signal to an RFID tag to vary an energy incident on the RFID tag. The control and processing subsystem is configured to control the sensing subsystem to vary the instantaneous power as a function of time periods within an interrogation cycle or sequence and to maintain an average power thereof below a predetermined value. There may be a series of actions wherein the interrogator energizes the RFID tag and receives a response therefrom in a single interrogation. There also may be a series of actions wherein the interrogator modulates and unmodulates a signal to the RFID tag before getting a response therefrom or a period of time wherein no RF energy is transmitted, then the RFID tag is charged, followed by a command from the interrogator to setup and listen.

For a better understanding of communication theory and radio frequency identification communication systems, see the following references "RFID Handbook," by Klaus Finkenzeller, published by John Wiley & Sons, Ltd., 2nd edition (2003), "Introduction to Spread Spectrum Communications," by Roger L. Peterson, et al., Prentice Hall Inc. (1995), "Modern Communications and Spread Spectrum," by George R. Cooper, et al., McGraw-Hill Book Inc. (1986), "An Introduction to Statistical Communication Theory," by John B. Thomas, published by John Wiley & Sons, Ltd. (1995), "Wireless Communications, Principles and Practice," by Theodore S. Rappaport, published by Prentice Hall Inc. (1996), "The Comprehensive Guide to Wireless Technologies," by Lawrence Harte, et al, published by APDG Publishing (1998), "Introduction to Wireless Local Loop," by William Webb, published by Artech Home Publishers (1998), "Digital Communications," by John C. Proakis, 3rd Edition, McGraw-Hill, Inc. (1995), "Antenna Engineering Handbook," by Richard Johnson and Henry Jasik, McGraw-Hill, Inc. (1992), "Wideband Wireless Digital Communications," by Andreas F. Molisch, Pearson Education (2000), and "The Mobile Communications Handbook," by Jerry D. Gibson, published by CRC Press in cooperation with IEEE Press (1996). For a better understanding of conventional readers, see the following readers, namely, an "MP9320 UHF Long-Range Reader" provided by SAMSys Technologies, Inc. of Ontario, Canada, an "MR-1824 Sentinel-Prox Medium Range Reader" by Applied Wireless ID of Monsey, N.Y. (see also U.S. Pat. No. 5,594,384 entitled "Enhanced Peak Detector," U.S. Pat. No. 6,377,176 entitled "Metal Compensated Radio Frequency Identification Reader," and U.S. Pat. No. 6,307,517 entitled "Metal Compensated Radio Frequency Identification Reader"), "2100 UAP Reader," provided by Intermec Technologies Corporation of Everett, Wash. and "ALR-9780 Reader," provided by Alien Technology Corporation of Morgan Hill, Calif. The aforementioned references, and all references herein, are incorporated herein by reference in their entirety.

Thus, an interrogator, an interrogation system and method of operating the same have been introduced herein. In an aspect, the interrogator includes an RFID sensing subsystem configured to detect an RFID object, and a control and processing subsystem configured to control an interrogation sequence of the RFID sensing subsystem by precharging the RFID object prior to detecting the RFID object.

The control and processing subsystem can control the interrogation sequence in many ways. For instance, the control and processing subsystem may vary an amplitude of a portion of the interrogation sequence. The control and processing subsystem is also configured to extend a duration of a continuous wave message of the interrogation sequence in accordance with precharging the RFID object.

In a related aspect, the interrogation sequence includes a continuous wave message, a data modulation message, a setup phase message and an unmodulated continuous wave message. In accordance therewith, the continuous wave message, the data modulation message and a setup phase message may have a first amplitude and the unmodulated continuous wave message may have a second amplitude.

In another related aspect, the RFID sensing subsystem is configured to transmit an unmodulated continuous wave message and detect a modulated version of the continuous wave message from the RFID object. In accordance therewith, the control and processing subsystem is configured to discern a presence of the RFID object from the modulated version of the continuous wave message and decode information from the RFID object.

Further refinements may also be provided to the interrogation systems as introduced herein. For instance, a method is described to increase the detection sensitivity of an interrogator such as described in the '450 Publication by an approach dealing with clock frequency errors in the responses transmitted by RFID tags. Passive and semi-active RFID tags operate on the principle of an interrogator sending out interrogating signals or an interrogation command by modulating an RF carrier and then receiving a response from an RFID tag by having that RFID tag modulate its backscatter characteristics in a controlled manner. In so doing, a unique modulated response is sent back to the interrogator where it is detected and decoded. Due to small size and low cost, interrogation systems like this are desirable in many applications including supply chain management, inventory control, and the general counting of and/or accounting for items in various industries and market segments.

Recent advancements in interrogators such as disclosed in the '450 Publication have greatly improved the ability of a sensitivity of the interrogator for such a passive or semi-active system's ability to be able to accurately and reliably receive and decode a very weak RFID tag to interrogator (also referred to as "Tag-to-Reader") signal. However, experience with commercially-available RFID tags has shown that the RFID tags sometimes transmit their response to an interrogation using a clock frequency that deviates from that specified by the interrogator. Correlation-based detectors, such as described in the '450 Publication, are acutely sensitive to deviations from the expected response clock rate and lose sensitivity when the RFID tag's response clock rate differs from the expected rate. Therefore, what is needed is an improved method for constructing a correlator that is tolerant of RFID tag response clock frequency variations.

In one aspect, an interrogator constructed according to the principles of the present invention is able to apply the correlation and non-coherent integration mechanisms described in the '450 Publication in situations in which the RFID tag response to the interrogator does not occur at the clock frequency specified by the interrogator by correlating not only against a synthetic tag signature with the correct clock, but also correlating against several synthetic tag signatures with clock errors approximating typical RFID tag response clock errors. The results of these parallel correlations are then compared, and the best response is selected. The process of creating a synthetic tag response signature with a clock slower or faster than normal is called "signature scaling." Use of signature scaling in the correlation and integration of these previously unusable RFID tag responses results in a substantial increase in interrogator sensitivity.

Figure 49:
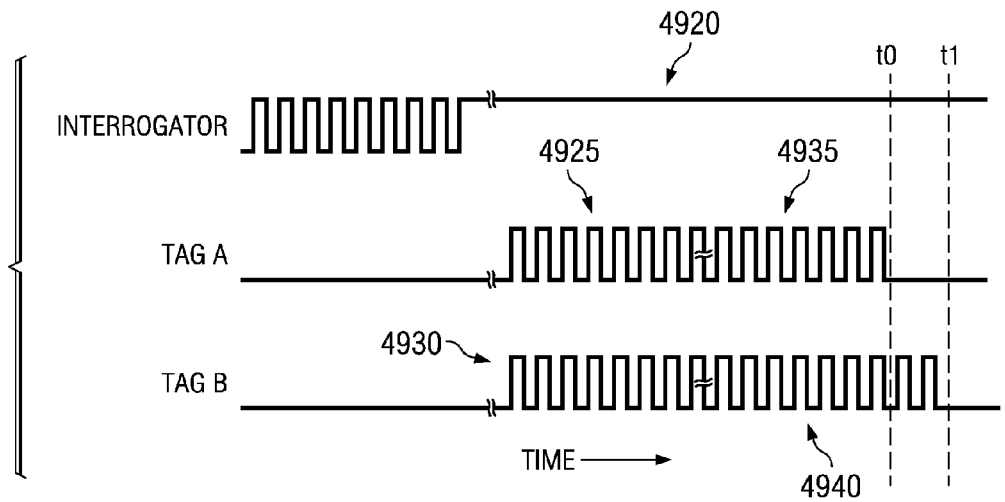
FIG. 49 illustrates waveform diagrams of an embodiment of an interrogation sequence from an interrogator, along with two RFID tag response waveforms from RFID tags designated Tag A and Tag B in accordance with the principles of the present invention.

Turning now to FIG. 49, illustrated are waveform diagrams of an embodiment of an interrogation sequence from an interrogator, along with two RFID tag response waveforms from RFID tags designated Tag A and Tag B in accordance with the principles of the present invention. As part of the interrogation sequence, an interrogator sends a known sequence of pulses intended to allow the RFID tag to synchronize its internal clock and thereby transmit its response at the frequency desired by the interrogator (the waveform shows a portion of a typical timing component of an interrogation request). The response waveforms for Tag A and Tag B show that the RFID tags are quiescent, but are receiving the timing pulses and synchronizing their internal clocks during this time. In this example, Tag A is assumed to have correctly set its internal clock by measuring the frequency of the timing pulses from the interrogator, but Tag B has derived a frequency with an approximate one percent error. Though a one percent error is not obvious in the first part of this FIGURE, its consequences are readily revealed later in time.

After transmission of the interrogation sequence, the interrogator enters a mode in which it transmits a continuous wave at the RFID tag modulation frequency to provide both power for the RFID tag and a signal that the RFID tag may modulate via backscattering. The section of the waveform for the interrogation sequence designated 4920 shows this continuous wave transmission. After an interval specified by the applicable RFID tag technology standard, the RFID tag begins transmitting its response, again, by modulating (e.g., backscattering) the continuous wave being transmitted by the interrogator. During the initial part of the response, no difference is discernable at the scale of this drawing between the response of Tag A as shown at 4925 and Tag B as shown at 4930.

By the end of response transmission, however, a difference is discernable between the response of Tag A at 4935 and that of Tag B at 4940. Due to the approximately one percent error in determining the proper response frequency, the response from Tag B has taken about one bit-time longer than the correct response of Tag A. The difference between the correct end of transmission time, t0, and the incorrect end of transmission time, t1, is the absolute error in the RFID tag response clock. This value, when divided by the transmission time of the complete RFID tag response using a correct clock, yields the clock error ratio.

Experience with RFID tags has shown that the response clock measurements are inaccurate in a significant percentage of RFID tag responses. The interrogator described in the '450 Publication provides a significant improvement in detection of RFID tags by, among other means, using correlation against a synthetic RFID tag signature. Correlation is acutely sensitive to clock rate between the synthetic tag signature and the received tag response, consequently correlation fails or exhibits decreased sensitivity in those cases in which the RFID tag responds at a clock frequency significantly different than that specified by the interrogator.

Figure 50:
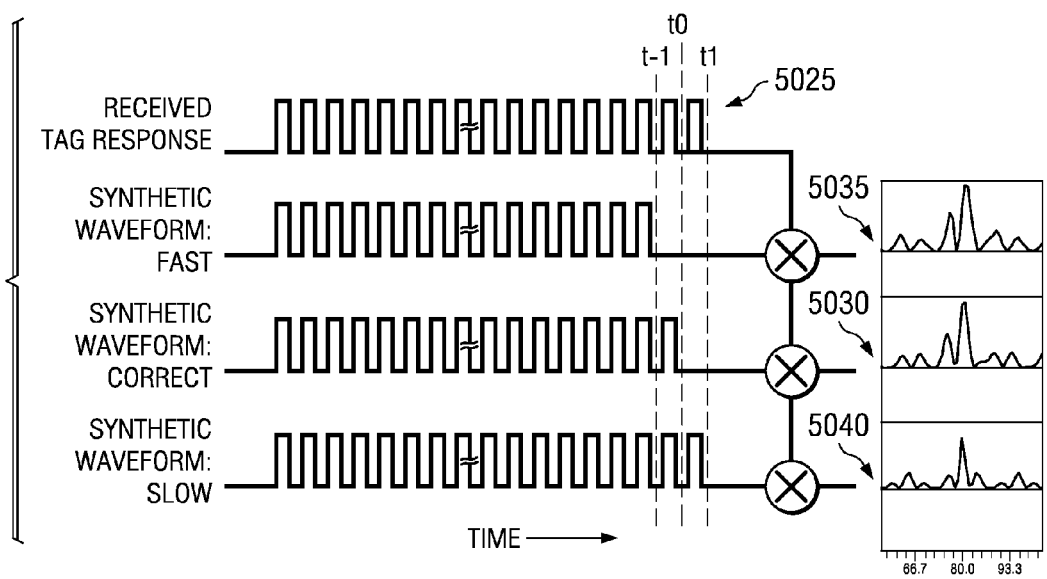
FIG. 50 illustrates waveform diagrams of an embodiment of an interrogation sequence from an interrogator, response for an RFID tag, and correlation signals from a correlation subsystem of an interrogator in accordance with the principles of the present invention.

Turning now to FIG. 50, illustrated are waveform diagrams of an embodiment of an interrogation sequence from an interrogator, response for an RFID tag, and correlation signals from a correlation subsystem of an interrogator in accordance with the principles of the present invention employing multiple correlators. In this embodiment, correlation is attempted between the synthetic reference code or signal at the expected clock rate and the received signal, as per the '450 Publication, but correlation is also attempted between synthetic reference codes, signals or waveforms generated with clock rates varying from the expected clock rate. Experience with RFID tags has shown that response clock frequency errors are bounded, and that a relatively small number of clock rate variant synthetic waveforms (and consequently a small number of additional correlations) are advantageous to detect the majority of RFID tag clocking errors. The response received from an RFID tag (using a clock rate approximately 0.5 percent slow in this case) is shown in the received RFID tag response. The synthetic waveform fast shows a synthetic signature with approximately a −0.5 percent error. The synthetic waveform correct shows a synthetic signature with a correct clock, and the synthetic waveform slow shows a synthetic signature with approximately a +0.5 percent error. The timing marks designated 5025 illustrate the relative differences in clock rates.

Per the '450 Publication, the RFID tag response waveform is correlated against a synthetic waveform at the correct clock rate, with the result shown at 5030. However, parallel correlations are also performed against synthetic tag signatures with a slightly fast clock, at 5035, and a slightly slow clock, at 5040. Note that the correlation result from the slow clock displays a valid correlation triangle, while the correlation results from the fast and correct synthetic waveforms display a malformation characteristic of clock errors in which two temporally separated correlation triangles appear to be overlaid, forming a characteristic "bat ears" shape. In this case, the correlation results are examined using methods described in the '450 Publication, resulting in positive detection despite the error in the RFID tag's response.

Thus, a control and processing system or subsystem for an interrogator, an interrogation system, and a method of verifying a presence of an RFID object has been introduced herein. In one aspect, the control and processing system includes a memory configured to store a reference code (e.g., a synthetically derived reference code). The control and processing system includes a correlation subsystem configured to correlate the reference code at a first clock rate and a second clock rate with a reply code from an RFID object and provide correlation signals therefrom. The correlation subsystem may include multiple correlators. A decision subsystem of the control and processing system is configured to verify a presence of the RFID object as a function of the correlation signals. Regarding an operation of the control and processing system, the reference code may be provided during an initialization stage of operation and the reply code may be provided during a post-initialization stage of operation.

In one aspect, the correlation subsystem is configured to correlate in a time domain employing an exclusive OR function or correlate employing a Fast Fourier Transform and a convolution theorem. In another aspect, the correlation subsystem includes a correlator configured to correlate at least two bits of the reference code with at least two bits of the reply code to derive correlation triangles. A correlation threshold sense of the correlation subsystem is configured to compare the correlation triangles to a threshold criteria to derive pulses to ascertain peaks of the correlation triangles. A summer of the correlation subsystem is configured to average a plurality of pulses from the correlation threshold sense to provide the correlation signals.

In another aspect, the decision subsystem includes a threshold detector configured to compare the correlation signals to a threshold. The decision subsystem is also configured to verify the presence of the RFID object by employing a statistical analysis on a result therefrom.

To further refine a sensitivity of an interrogation system, a method is proposed to detect the presence of an RFID tag within the interrogation field in cases in which the RFID tag does not transmit a full response to an interrogation. Radio frequency identification is one of the fastest growing areas within the field of automatic identification and data collection. A reason for the proliferation of RFID systems is that RFID tags may be affixed to a variety of diverse objects (also referred to as "RFID objects") and a presence of the RFID tags may be detected without actually physically viewing or contacting the RFID tag. As a result, multiple applications have been developed for the RFID systems and more are being developed every day.

The parameters for the applications of the RFID systems vary widely, but can generally be divided into three significant categories. First, an ability to read the RFID tags rapidly. Another category revolves around an ability to read a significant number of the RFID tags simultaneously (or nearly simultaneously). A third category stems from an ability to read the RFID tags reliably at increased ranges or under conditions wherein the radio frequency signals have been substantially attenuated or distorted, or in environments in which there is a substantial amount of ambient radio frequency noise or interference occurring within the frequency range used by the interrogator and tags.

While significant progress has been made in the area of reading multiple RFID tags almost simultaneously (see, for instance, U.S. Pat. No. 6,265,962 entitled "Method for Resolving Signal Collisions Between Multiple RFID Transponders in a Field," to Black, et. al., issued Jul. 24, 2001, which is incorporated herein by reference), there is still substantial room for significant improvement in the area of reading the RFID tags reliably at increased ranges, or under conditions when the radio frequency signals have been substantially attenuated, or in environments in which a substantial amount of ambient radio frequency noise or interference exists within the frequency range used by the interrogator and RFID tags. In some environments, the energy transmitted by the interrogator is attenuated to the extent that insufficient energy exists for an RFID tag to complete transmission, yet detection of a partial transmission provides definitive evidence of the presence of an RFID tag in the interrogation field and, therefore, valuable information in certain applications. Therefore, what is needed is a method to reliably detect partial transmissions from RFID tags.

In one aspect, an interrogator constructed according to the principles of the present invention is able to detect the presence of an RFID tag within the interrogation field even if the RFID tag has insufficient power to transmit a complete response. Experience with RFID tags has shown that the energy required to activate an RFID tag is relatively low as compared to the energy required for the RFID tag to backscatter energy from the interrogator by switching impedances on the RFID tag's antenna. Thus, in situations wherein energy from the transmitter is heavily attenuated, an RFID tag may receive sufficient energy to activate and begin transmitting, but the act of transmitting soon exhausts all available energy and the RFID tag deactivates before the transmission is complete. Thus, the partial tag integration capability described in the '450 Publication is extended, thereby allowing the interrogator to correlate as little as only the first few bits of the RFID tag's response (typically a common value among a class of RFID tags) against a synthetic signature (see the '450 Publication) and determine, to a high degree of reliability, the presence of an RFID tag.

Figure 51:
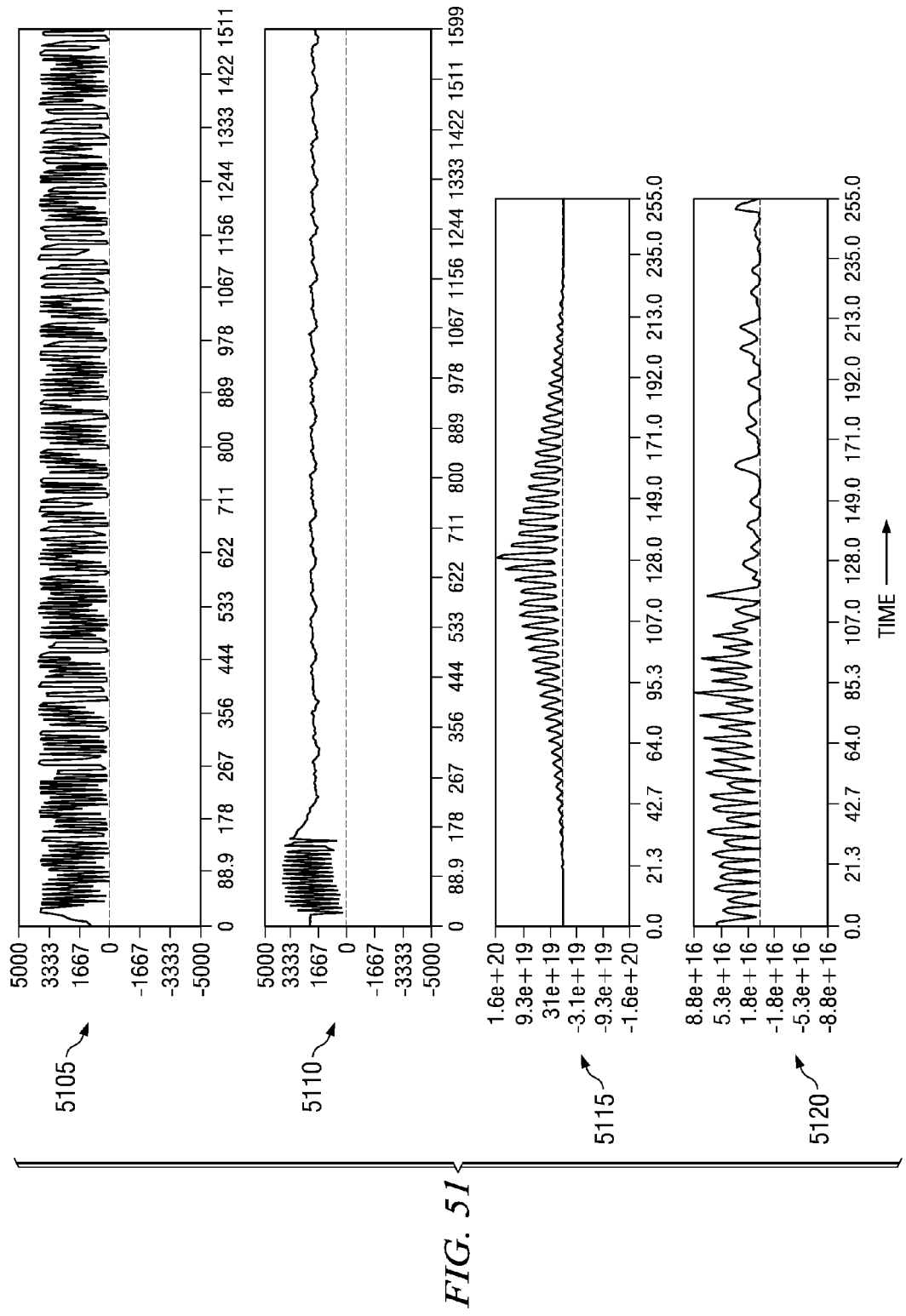
FIG. 51 illustrates waveform diagrams of an embodiment of full RFID tag responses and a partial RFID tag response in accordance with the principles of the present invention.

Turning now to FIG. 51, illustrated are waveform diagrams of an embodiment of full RFID tag responses and a partial RFID tag response in accordance with the principles of the present invention. As described above, partial RFID tag responses are common when the interrogator's signal is heavily attenuated, resulting in insufficient energy reaching the RFID tag for a complete response. In such cases, the RFID tag frequently will begin transmission, only to fail and cease operating during the transmission due to exhaustion of stored energy. The full RFID tag response waveform 5105 shows a complete response from an RFID tag, while the partial RFID tag response waveform 5110 shows a partial response, in which the RFID tag had insufficient power to continue transmitting after the 8th bit of the preamble.

In certain situations it is useful to determine if an RFID tag exists within the interrogation field, even if the RFID tag's information cannot be completely read. Using the correlation method as described in the '450 Publication, it is possible to correlate against the RFID tag response preamble (e.g., may include a pilot tone along with a fixed number of bits independent of the RFID tag's identification), which is common to RFID tags of a specific type. The partial correlation result when RFID tag present waveform 5115 shows the characteristic result of correlating the eight bit response in accordance with the partial tag response waveform 5110 with an eight bit synthetic tag signature using the methods described in the '450 Publication. The partial correlation result when no RFID tag present waveform 5120 shows the results of the same type of correlation when no RFID tag response was received. Additionally, it may be advantageous to perform correlation on the pilot tone wherein the RFID tag modulates the carrier by a fixed constant frequency for a period of time before sending any specifically encoded data bits.

Inspection of the results of partial correlation, using techniques measuring, among other factors, symmetry, the monotonicity, and the peak spacing, are sufficient to reliably differentiate the two RFID tag response waveforms 5115, 5120 and detect the presence of a partially firing RFID tag to a high degree of accuracy. Even correlating only an eight bit preamble as illustrated will provide a nine decibel increase in sensitivity when an RFID tag is present, and substantially increases the probability that the presence of an RFID tag will be detected within the interrogation field. Additional detection enhancement is possible should more or other portions of the backscatter waveform be available for processing, which is comprehended by this invention.

Additionally, multiple correlators, as discussed above in signature scaling, may also be employed to further enhance the sensitivity of partial tag response detection. This is because as an RFID tag no longer has adequate energy to continue proper response to an inquiry, it may nevertheless continue for several more cycles. The frequency of those last cycles, however, will likely differ sufficiently from the initial cycles so that they will not contribute to the gain improvement due to correlation. Multiple correlators as discussed above in signature scaling along with the inclusion of additional correlators so as to cover a broader frequency range will capture those final cycles. Then, because in this instance multiple responses may exist, systems that combine the responses of multiple correlators can be used to increase the strength of the detected response. As an example, the simple noncoherent addition of all responses will provide a stronger response. The simple example above is only meant to illustrate the concepts of this invention and other methods are certainly possible using this data, and this invention comprehends them as well.

Systems and methods are introduced to both increase the detection sensitivity and the discrimination capability of a correlation-based detector as described in the '450 Publication by an approach that correlates a received signal against a synthetic signal containing either only the clock waveform of the RFID tag, or the data waveform of the RFID tag. As mentioned above, passive and semi-active RFID tags operate on the principle of an interrogator sending out interrogating signals by modulating an RF carrier and then receiving a response from an RFID tag by having that RFID tag modulate its backscatter characteristics in a controlled manner. In so doing, a unique modulated response is sent back to the interrogator or reader to be detected and decoded. Due to their small size and low cost, systems like this are desirable in many applications, including supply chain management, inventory control, and the general counting of and/or accounting for items in various industries and market segments.

Additionally, recent advancements in interrogator architecture such as disclosed in the '450 Publication have greatly improved the ability of an interrogator's sensitivity for such a passive or semi-active system's ability to be able to accurately and reliably receive and decode a very weak Tag-to-Reader signal. The attenuation and radio frequency noise/interference in some environments may be so severe that attempting correlation with a synthetic signature for a specific RFID tag's informational content may not be feasible due to decreased sensitivity, and certain applications exist in which it is valuable to detect the presence of an RFID tag within the interrogation field even when it is not possible to uniquely identify that RFID tag through reception of its complete identification by the interrogator. Other applications exist in which it is necessary to distinguish between the signatures of two RFID tags with substantially identical data contents under conditions of attenuation and radio frequency noise/interference. What is needed, therefore, is a system of correlating with a synthetic tag signature that provides a high detection value for any RFID tag within the interrogator's field, and a method of improving discrimination capability for the RFID tags having substantially identical data values.

In one aspect, an interrogator constructed according to the principles of the present invention is able to detect the presence of any RFID tag in the interrogation field, with a single interrogation command, under conditions in which the complete RFID tag response is unreadable due to attenuation or radio frequency noise or other interference, by detecting and correlating on the presence of the clock information signal that is part of every RFID tag response using correlation techniques taught in the '450 Publication regardless of information content. Two advantages accrue through the use of this mechanism. First, it provides an efficient method of determining if any RFID tag within a specific air interface standard exists within the interrogation field, regardless of RFID tag encoding. Second, it provides a method of determining if an RFID tag exists within the interrogation field even if attenuation or noise or other effects are such that the information content of the RFID tag response cannot be detected.

In another aspect, an interrogator constructed according to the principles of the present invention is able to discriminate between the signals of two RFID tags with substantially identical data values by detecting and correlating on the presence of the data component or information of the RFID tag response using correlation techniques taught in the '450 Publication. This method provides the advantage of additional detection accuracy for situations in which similarly numbered RFID tags should be detected to a very high degree of accuracy.

Figure 52:
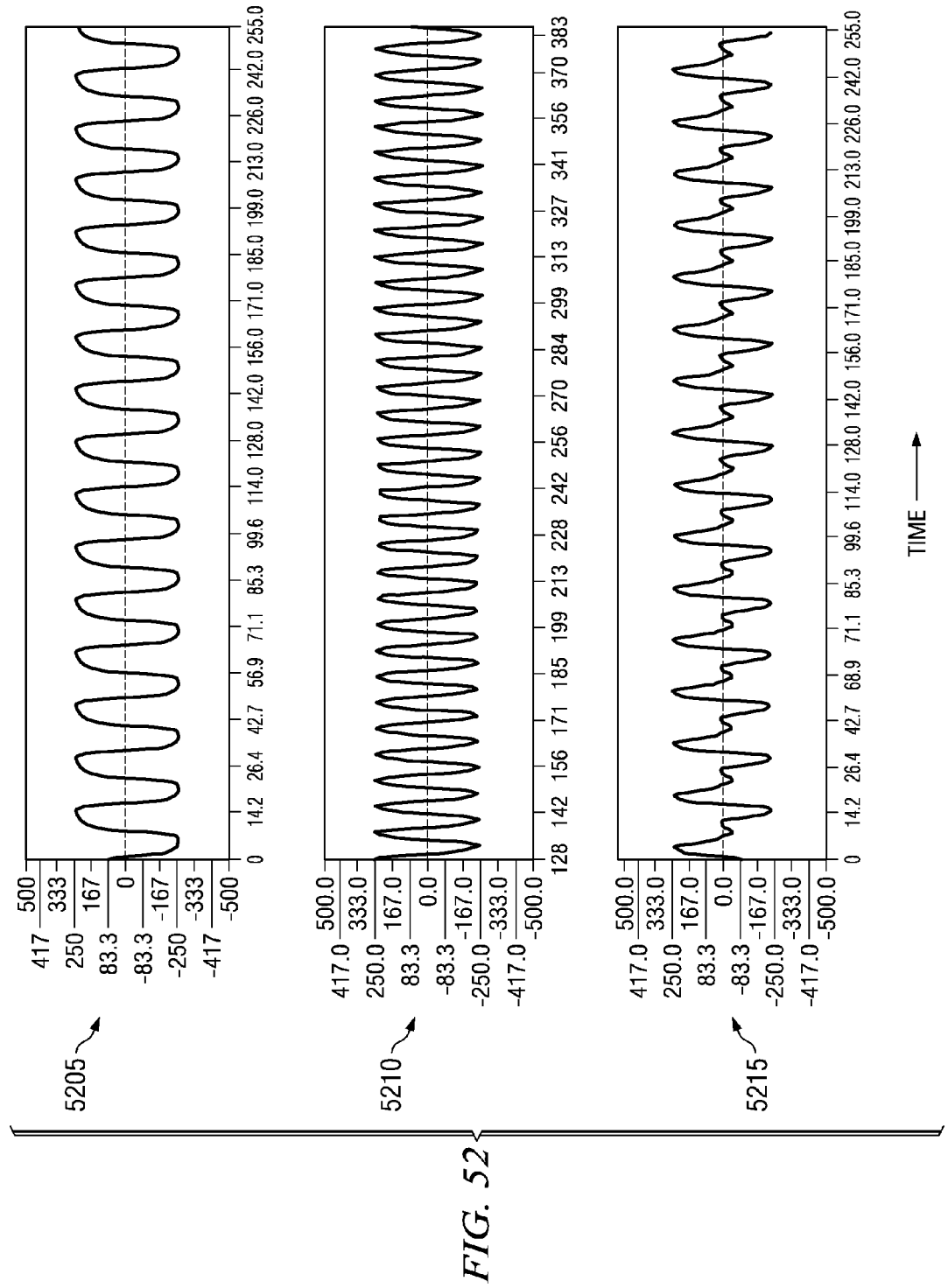
FIG. 52 illustrates waveform diagrams of an embodiment for a string of modulated binary zeros and for a string of modulated binary ones as encoded using frequency shift keying in accordance with the principles of the present invention.

Turning now to FIG. 52, illustrated are waveform diagrams of an embodiment for a string of modulated binary zeros (waveform designated 5205) and for a string of modulated binary ones (waveform designated 5210) as encoded using frequency shift keying in accordance with the principles of the present invention. In this example, a binary zero has a single zero-crossing, while a binary one has two zero crossings. Providing that there be at least one crossing per binary data bit ensures that the receiver (e.g., an RFID sensing subsystem within the interrogator) of this waveform can correctly decode it. Thus, one of these zero crossings is common to both zero and one symbols, and functions as an embedded timing reference, or "clock" for the receiver. Since each symbol has a common transition, regardless of whether a one or zero is being transmitted, there is a great deal of information in common between the signals transmitted by two different RFID tags, even if the data values within a reply code of the RFID tags themselves are completely different. This characteristic of an RFID tag response encoding can be exploited to improve both reception sensitivity and reception discrimination. The waveform designated 5215 shows averaging the modulated one and zero waveforms above, hereinafter known as the "clock" waveform.

Figure 53:
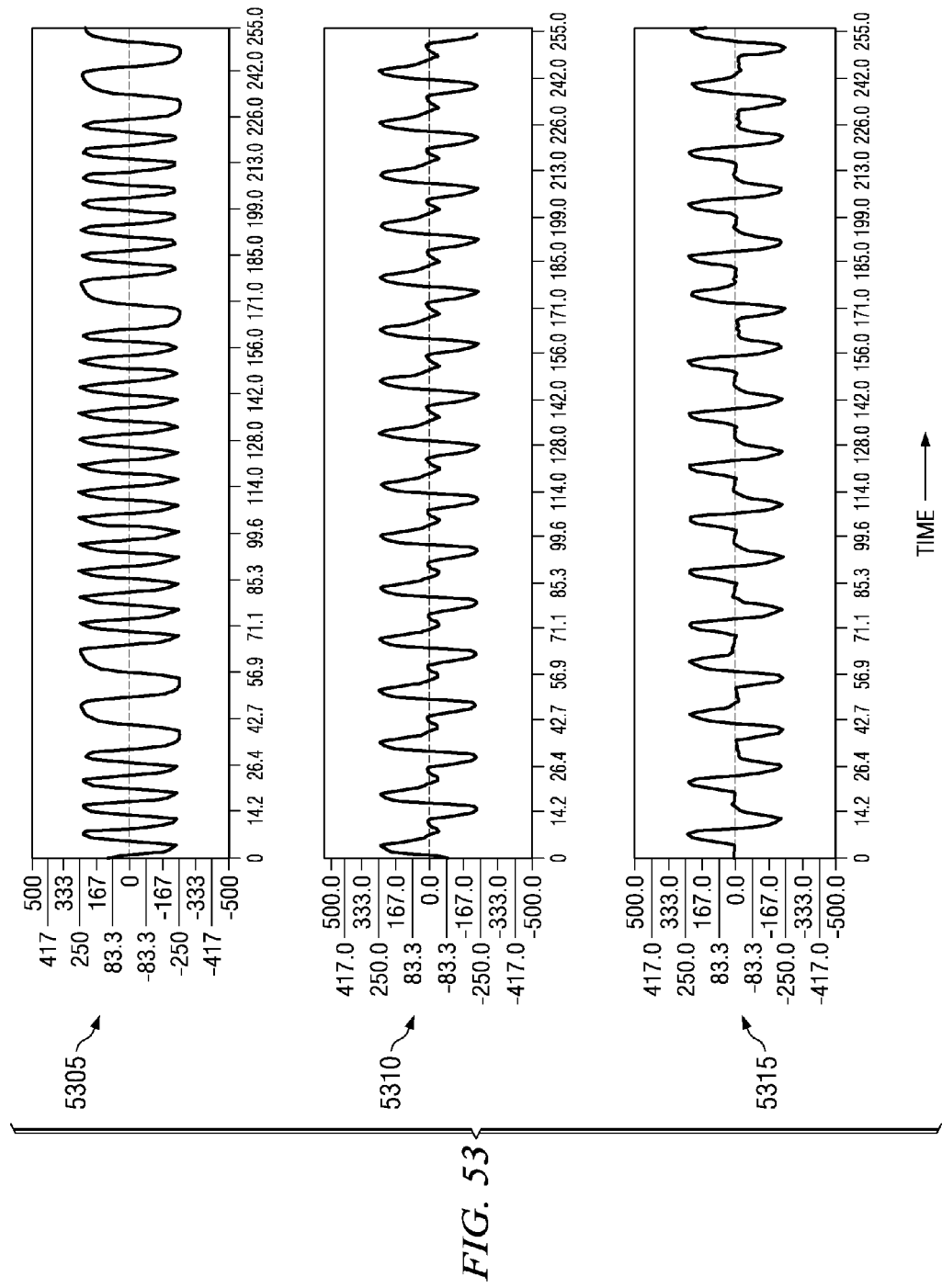
FIG. 53 illustrates waveform diagrams of an embodiment of reference codes or RFID tag signatures including data and clock signals or information, clock-only signals or information, and data-only signals or information in accordance with the principles of the present invention.

Turning now to FIG. 53, illustrated are waveform diagrams of an embodiment of reference codes or RFID tag signatures including data and clock signals or information (waveform designated 5305), clock-only signals or information (waveform designated 5310), and data-only signals or information (waveform designated 5315) in accordance with the principles of the present invention. A synthetically derived data and clock reference code may be used for correlation as in the '450 Publication and provides a balance between the ability to detect an RFID tag and the ability to discriminate between two RFID tags with substantially similar data information.

Correlating with the clock-only information will produce a positive result if any RFID tag within an entire class of RFID tags responds, and will produce a usable correlation result under conditions of attenuation and interference that would otherwise preclude correlation for a specific RFID tag data value. Thus, clock-only correlation provides benefits in situations such as described in the '450 Publication to confirm, for instance, that no RFID tag exists within the interrogator's field, as well as in other similar situations.

Correlating with the data-only information correlates the received reply code or portion thereof against a signal that has had the common clock information removed for the reference code. This has the effect of increasing the difference in correlation results between two RFID tags with similar data information, since the clock information no longer contributes to the correlation result. Data-only correlation provides benefits in situations to discriminate, for instance, between two or more RFID tags with similar data information.

A method is proposed to improve the performance of non-coherent integration correlation based detection systems, such as described in the '450 Publication, by analyzing the energy distribution within the correlation results to generate a probability of detection value that can be used by other statistical methods to detect or identify RFID tags with a high degree of certainty. As mentioned above, passive and semi-active RFID tags operate on the principle of an interrogator sending out interrogating signals by modulating an RF carrier and then receiving a response from an RFID tag by having that RFID tag modulate its backscatter characteristics in a controlled manner. In so doing, a unique modulated response is sent back to the interrogator or reader wherein it is detected and decoded. Due to their small size and low cost, systems like this are desirable in many applications including supply chain management, inventory control, and the general counting of and/or accounting for items in various industries and market segments.

Thus, an interrogator, an interrogation system, and a method of verifying a presence of an RFID object has been introduced herein. In one aspect, the interrogator includes an RFID sensing subsystem configured to receive a partial response from an RFID object including a portion of a reply code. The interrogator also includes a control and processing subsystem including a correlation subsystem configured to correlate a portion of a reference code with the portion of the reply code and provide a correlation signal therefrom. The control and processing subsystem also includes a decision subsystem configured to verify a presence of the RFID object as a function of the correlation signal.

In a related aspect, the portion of the reply code may include clock or data information and the portion of the reference code may include synthetically derived clock or data information. In accordance therewith, the correlation subsystem is configured to correlate the synthetically derived clock or data information with the clock or data information of the reply code and provide a correlation signal therefrom. Regarding an operation of the interrogator, the reference code may be provided during an initialization stage of operation and the portion of the reply code may be provided during a post-initialization stage of operation.

In one aspect, the correlation subsystem includes multiple correlators and the correlation subsystem is configured to correlate in a time domain employing an exclusive OR function or employing a Fast Fourier Transform and a convolution theorem. In another aspect, the correlation subsystem includes a correlator configured to correlate at least two bits of the reference code with at least two bits of the reply code to derive a correlation triangle. A correlation threshold sense of the correlation subsystem is configured to compare the correlation triangle to a threshold criteria to derive a pulse to ascertain a peak of the correlation triangle. A summer of the correlation subsystem is configured to average a plurality of pulses from the correlation threshold sense to provide the correlation signal. The correlation subsystem may also be configured to employ multiple amplitude bits of the portion of the reference code and the portion of the reply code.

In another aspect, the decision subsystem includes a threshold detector configured to compare the correlation signal to a threshold. The decision subsystem may also be configured to verify the presence of the RFID object by employing a statistical analysis on a result therefrom.

Recent advancements in RFID interrogation architecture such as disclosed in the '450 Publication have greatly improved the ability of a sensitivity of the interrogator for such a passive or semi-active system's ability to be able to accurately and reliably receive and decode a very weak Tag-to-Reader signal. The attenuation and radio frequency noise/interference in some environments may be so severe that the results of a single correlation, or a small number of correlations, are inadequate to declare, with a high degree of certainty, the presence or absence of any RFID tag, or of a specific RFID tag. What is needed, therefore, is a means for analyzing the correlation results between a sampled waveform and a synthetically derived reference code or signature and to determine a detection probability that can be used by other statistical processing mechanisms to detect the presence of an RFID tag with a high degree of certainty, or to identify a specific RFID tag with a high degree of certainty.

In one aspect, an interrogator constructed according to the principles of the present invention can detect the presence of any RFID tag within the interrogation field under highly attenuative or high ambient radio frequency noise/interference conditions by examination of the energy distribution within the correlation response (see, e.g., the '450 Publication). Using this method in conjunction with the correlation and integration methods described in the '450 Publication allows statistical methods to be used to determine the presence and/or identity of an RFID tag within the interrogation field to a high degree of certainty.

In another aspect, an interrogator constructed according to the principles of the present invention can discriminate between the responses of RFID tags with similar informational content within the interrogation field under highly attenuative or high ambient radio frequency noise/interference conditions by examination of the energy distribution within the correlation response (see, e.g., the '450 Publication). Using this method in conjunction with the correlation and integration methods described in the '450 Publication allows statistical methods to be used to determine the presence and/or identity of an RFID tag within the interrogation field to a high degree of certainty.

Figure 54:
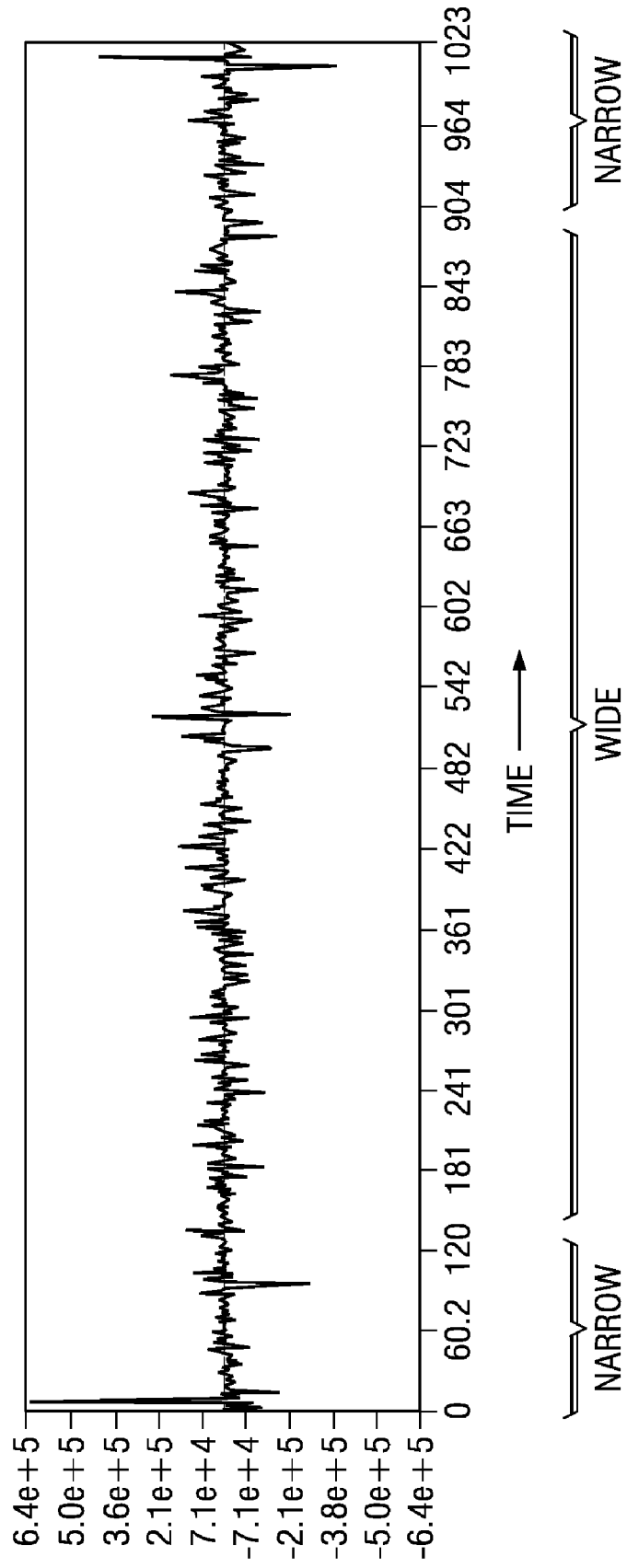
FIG. 54 illustrates a waveform diagram of an embodiment of a non-coherently integrated correlation response for an RFID tag matching a reference code or signature in accordance with an interrogator constructed according to the principles of the present invention.

Turning now to FIG. 54, illustrated is a waveform diagram of an embodiment of a non-coherently integrated correlation response for an RFID tag matching a reference code or signature in accordance with an interrogator constructed according to the principles of the present invention. Here two values are calculated for the correlation response, namely, a "narrow-band" signal to noise ratio ("SNR") and a "wide-band" signal to noise ratio ("SNR"). Based upon implementation and application constraints, the correlation response is partitioned into two parts, namely, data in the two end areas (designated "Narrow") and the data in the center (designated "Wide"). The data in the end areas of the correlation response are referred to as the "narrow-band" SNR values, and the data in the center of the waveform are referred to as the "wide-band" SNR values. The narrow-band SNR is the ratio of the peak value within the narrow-band area to the average value within the narrow-band area, using absolute values.

$$SNR_{narrow} = |narrow|_{max} / |narrow|$$

Similarly, the wide-band SNR is the ratio of the peak value within the wide-band area to the average value within the wide-band area, using absolute values.

$$SNR_{wide} = |wide|_{max} / |wide|.$$

Figure 55:
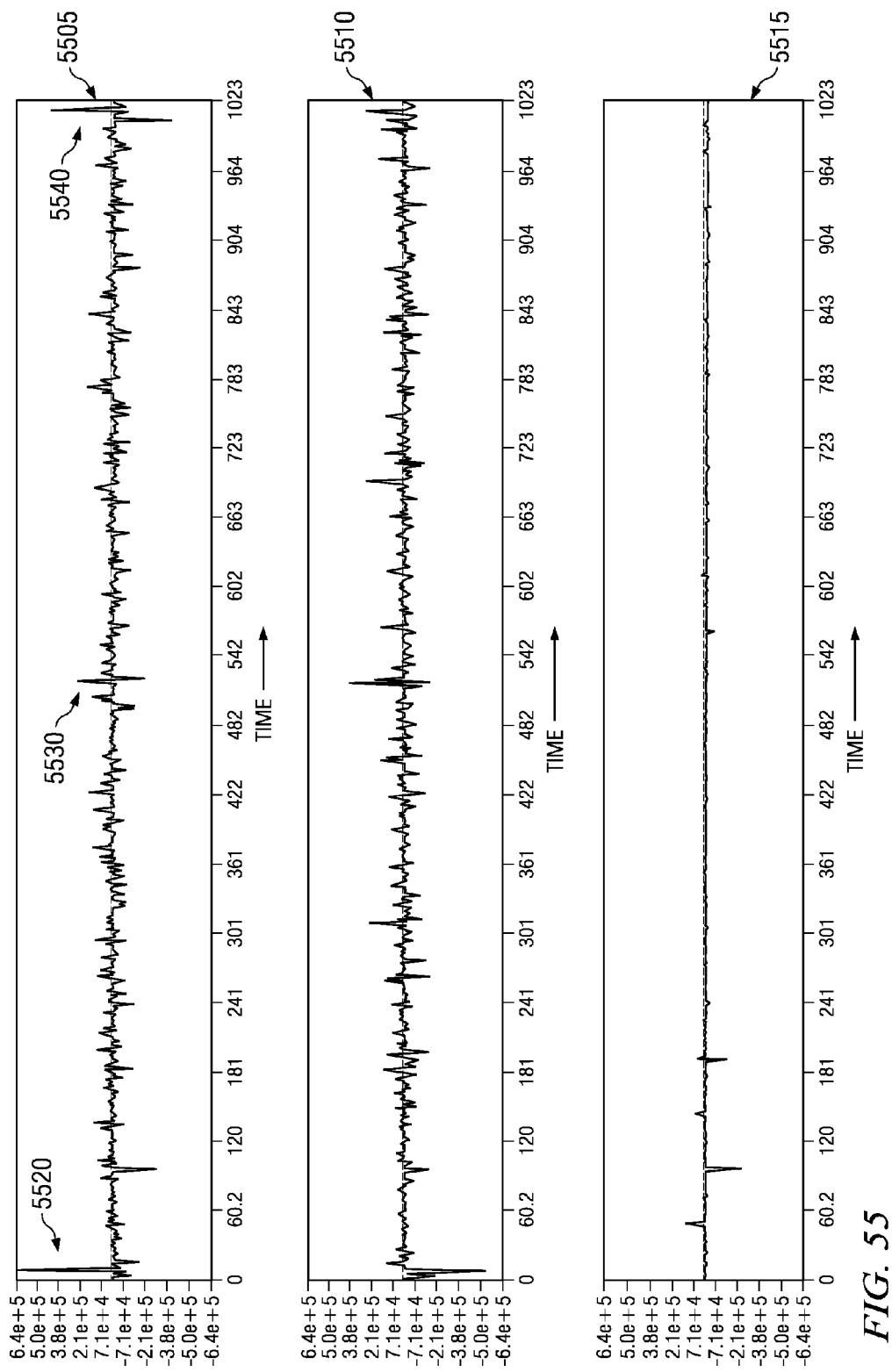
FIG. 55 illustrates waveform diagrams of an embodiment of a non-coherently integrated correlation response for an RFID tag that matches a reference code or signature, for an RFID tag with a similar reply code to the reference code, and for no RFID tag present in accordance with an interrogator constructed according to the principles of the present invention.

Turning now to FIG. 55, illustrated are waveform diagrams of an embodiment of a non-coherently integrated correlation response for an RFID tag that matches a reference code or signature (waveform designated 5505), for an RFID tag with a similar reply code to the reference code (waveform designated 5510), and for no RFID tag present (waveform designated 5515) in accordance with an interrogator constructed according to the principles of the present invention. Note that on the waveforms a significant portion of the correlation data (the "correlation triangle") is split between the two ends of the waveform, while the information of least interest occupies the center of the waveform. Thus, on the good correlation results, the waveform 5505 for the RFID tag shows significant results of the correlation at ends (designated 5520, 5540) thereof, and the least significant information is at the center (designated 5530) thereof.

The waveform 5510 for the RFID tag with a similar reply code to the reference code demonstrates about a three decibel difference from the RFID tag in the waveform 5505. Note that the magnitude of the peaks at the ends of the waveform is significantly smaller than that in the waveform 5505. Not as obvious is the fact that the average of the peaks in the center portion of the waveform is higher than the same average for the waveform 5505. The waveform 5515, where no RFID tag is present, provides a more extreme case.

Comparison of narrow-band SNR values to wide-band SNR values provides an indication of the quality of the match, with greater difference between the narrow-band SNR and wide-band SNR indicating a stronger match to the reference waveform. This information is then suitable for use with statistical analysis methods using multiple samples to determine the presence and/or identity of an RFID tag.

Thus, a control and processing system or subsystem for an interrogator, an interrogation system, and a method of verifying a presence of an RFID object has been introduced herein. In one aspect, the control and processing system includes a memory configured to store a reference code (e.g., a synthetically derived reference code). In one aspect, the control and processing system includes a correlation subsystem configured to correlate the reference code with a reply code from an RFID object and provide a correlation signal therefrom. The correlation signal includes a narrow-band area having a narrow-band SNR value and a wide-band area having a wide-band SNR value. The control and processing system also includes a decision subsystem configured to verify a presence of the RFID object as a function of the correlation signal wherein a probability of a match between the reference code and the reply code increases with a greater difference between the narrow-band SNR value and the wide-band SNR value. Regarding an operation of the control and processing system, the reference code may be provided during an initialization stage of operation and the reply code may be provided during a post-initialization stage of operation.

In a related aspect, the narrow-band SNR value is a ratio of an absolute value of a peak value within the narrow-band area to an absolute value of an average value within the narrow-band area. The wide-band SNR value is a ratio of an absolute value of a peak value within the wide-band area to an absolute value of an average value within the wide-band area. Also, the narrow-band area is typically located proximate an end of the correlation signal and the wide-band area is typically located proximate a center of the correlation signal.

In one aspect, the correlation subsystem includes multiple correlators and the correlation subsystem is configured to correlate in a time domain employing an exclusive OR function or correlate employing a Fast Fourier Transform and a convolution theorem. In another aspect, the correlation subsystem includes a correlator configured to correlate at least two bits of the reference code with at least two bits of the reply code to derive correlation triangles. A correlation threshold sense of the correlation subsystem is configured to compare the correlation triangles to a threshold criteria to derive pulses to ascertain peaks of the correlation triangles. A summer of the correlation subsystem is configured to average a plurality of pulses from the correlation threshold sense to provide the correlation signals.

In another aspect, the decision subsystem includes a threshold detector configured to compare the correlation signal to a threshold. The decision subsystem may also be configured to verify the presence of the RFID object by employing a statistical analysis on a result therefrom.

A method is proposed to improve the RFID tag detection capabilities of the non-coherent integration correlation system described in the '450 Publication under conditions of signal attenuation or radio frequency noise and interference so severe that a single or small number of interrogations will not produce the level of accuracy required to declare an RFID tag present or absent within the interrogation field. As mentioned above, passive and semi-active RFID tags operate on the principle of an interrogator sending out interrogating signals by modulating an RF carrier and then receiving a response from an RFID tag by having that RFID tag modulate its backscatter characteristics in a controlled manner. In so doing, a unique modulated response is sent back to the interrogator or reader wherein it is detected and decoded. Due to their small size and low cost, systems like this are desirable in many applications including supply chain management, inventory control, and the general counting of and/or accounting for items in various industries and market segments.

Recent advancements in RFID interrogation architecture such as disclosed in the '450 Publication have greatly improved the ability of a sensitivity of the interrogator for such a passive or semi-active system's ability to be able to accurately and reliably receive and decode a very weak Tag-to-Reader signal. The attenuation and radio frequency noise/interference in some environments may be so severe that the results of a single correlation, or a small number of correlations, are inadequate to declare, with a high degree of certainty, the presence or absence of any RFID tag, or of a specific RFID tag. What is needed, therefore, is a method to process the results of many probabilistic results and obtain an indication of the presence or absence of an RFID tag within the interrogator's field, or to identify a specific RFID tag, with a defined degree of certainty.

In one aspect, an interrogator constructed according to the principles of the present invention can accumulate the results for samples that show an RFID tag "possibly present," and test the accumulated value against an empirically derived threshold. In order to prevent unbounded accumulation of "possibly present" samples, the accumulation method decrements or decays the accumulated value based upon the raw number of samples examined. It is only when the accumulated value exceeds a constant that the RFID tag is declared present. The decay constant and detection threshold constant may be selected to trade accuracy against sensitivity. Preferably, a minimum number of samples are employed before a result can be declared.

Figure 56:
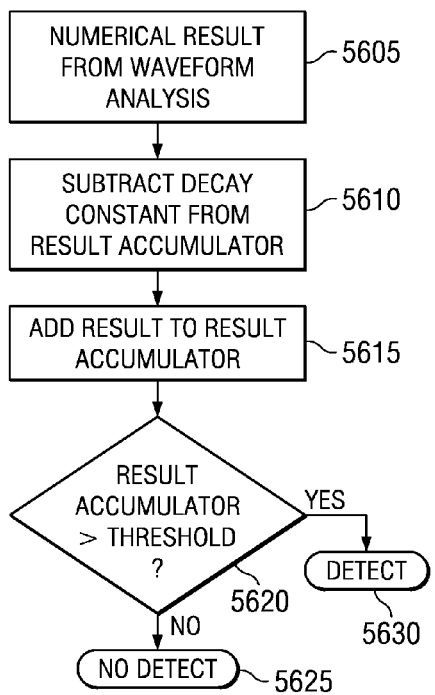
FIGS. 56 and 57 illustrate flow diagrams of embodiments of methods of operating an interrogation system according to the principles of the present invention.
Figure 57:
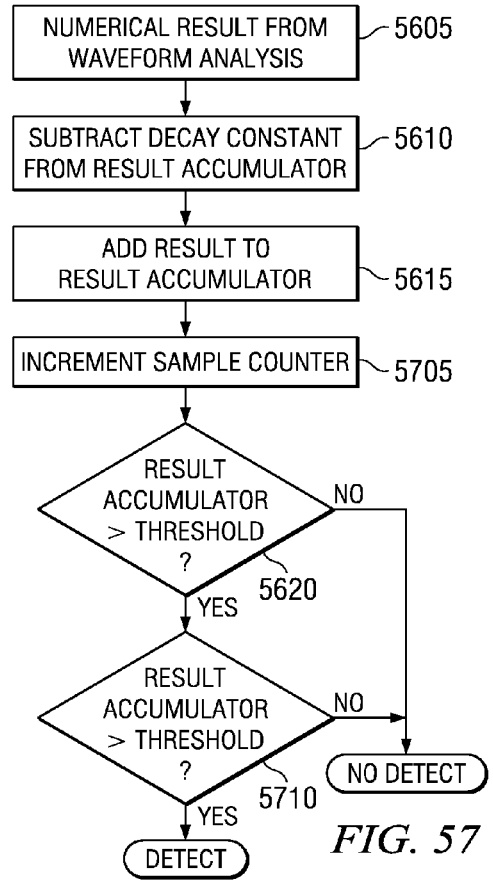

Turning to FIGS. 56 and 57, illustrated are flow diagrams of embodiments of methods of operating an interrogation system according to the principles of the present invention. Here, a waveform sample is obtained and analyzed using a method that produces a statistically significant, but not definitive indication of RFID tag presence, expressed as a result dimensionless number in a step 5605. This number is then used as an input to a process as set forth below. The method first "decays" or decrements the existing value of the result accumulator by an amount known as the "decay constant" in a step 5610, then adds the result number to the result accumulator in a step 5615. The new value of the result accumulator is tested to see if it exceeds the constant "detection threshold" in a step 5620. If it does, detection is reported in a step 5630, otherwise, no detection is reported in a step 5625.

In another embodiment illustrated with respect to FIG. 57, the method described in FIG. 56 is modified to ensure that a minimum number of samples are considered prior to declaring detection. A "sample counter" indicating the number of samples included in the accumulated result is incremented in a step 5705. When the result accumulator exceeds the detection threshold, an additional test is performed to ensure the minimum number of samples has been reached in a step 5710 prior to declaring detection.

Additionally, combining the concepts discussed above can create systems with greatly enhanced overall detection capabilities and with capabilities greater than any of the above concepts when considered individually. This enhanced capability is referred to as deep scan. As an example, combining the teachings of the '450 Publication with, for instance, the power management and partial RFID tag response detection can provide a deep scan system. Of course, other concepts may also be combined with the deep scan system to further enhance detection sensitivity.

The present invention is directed, in general, to communication systems and, more specifically, to an identification system for a metal instrument and an interrogation system employing the same. In accordance therewith, the present invention provides a metal instrument including an RFID chip and a coupler configured to couple the RFID chip to the metal instrument to allow the metal instrument to serve as an antenna therefor. The metal instrument may also include an insulator and strap, and an inductive loop. The metal instrument may also include a depression for the RFID chip and coupler, and protected by an encapsulant. The metal instrument may be a medical instrument and the RFID chip may include information associated with the metal instrument.

Figure 58:
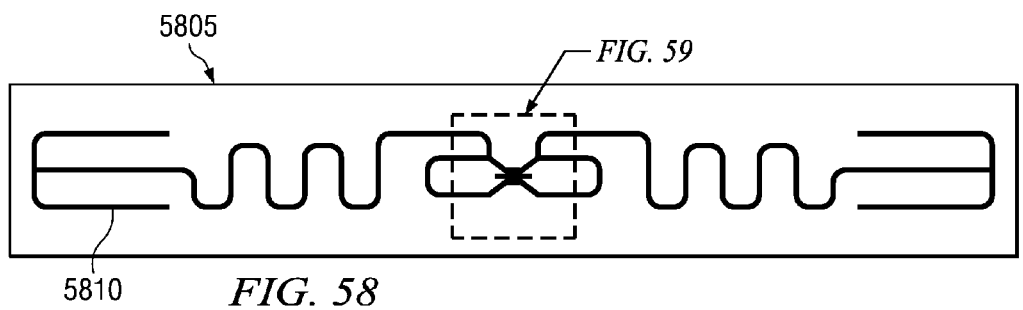
FIGS. 58 and 59 illustrate diagrams of embodiments of an RFID tag according to the principles of the present invention.
Figure 59:
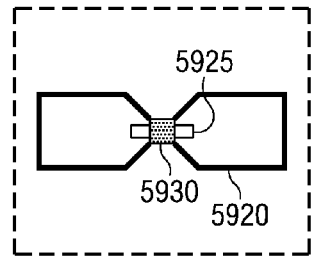

Turning now to FIGS. 58 and 59, illustrated are diagrams of embodiments of an RFID tag according to the principles of the present invention. The RFID tag includes an outer covering or encapsulant 5805 that protects the tag from the environment. Also, the RFID tag includes an antenna 5810 that receives signals from an interrogator, and in the case of a passive tag responds to the interrogator by matching and mismatching the same antenna. Central to the RFID tag is an assembly that contains the active semiconductor element. Regarding FIG. 59, the assembly is shown in greater detail including a supportive element (often called a strap) 5920 upon which an RFID chip 5930 is placed. Conductive elements 5925 perform the electrical connection. This is but one example of an RFID tag, and other architectures may be employed as well.

Figure 60:
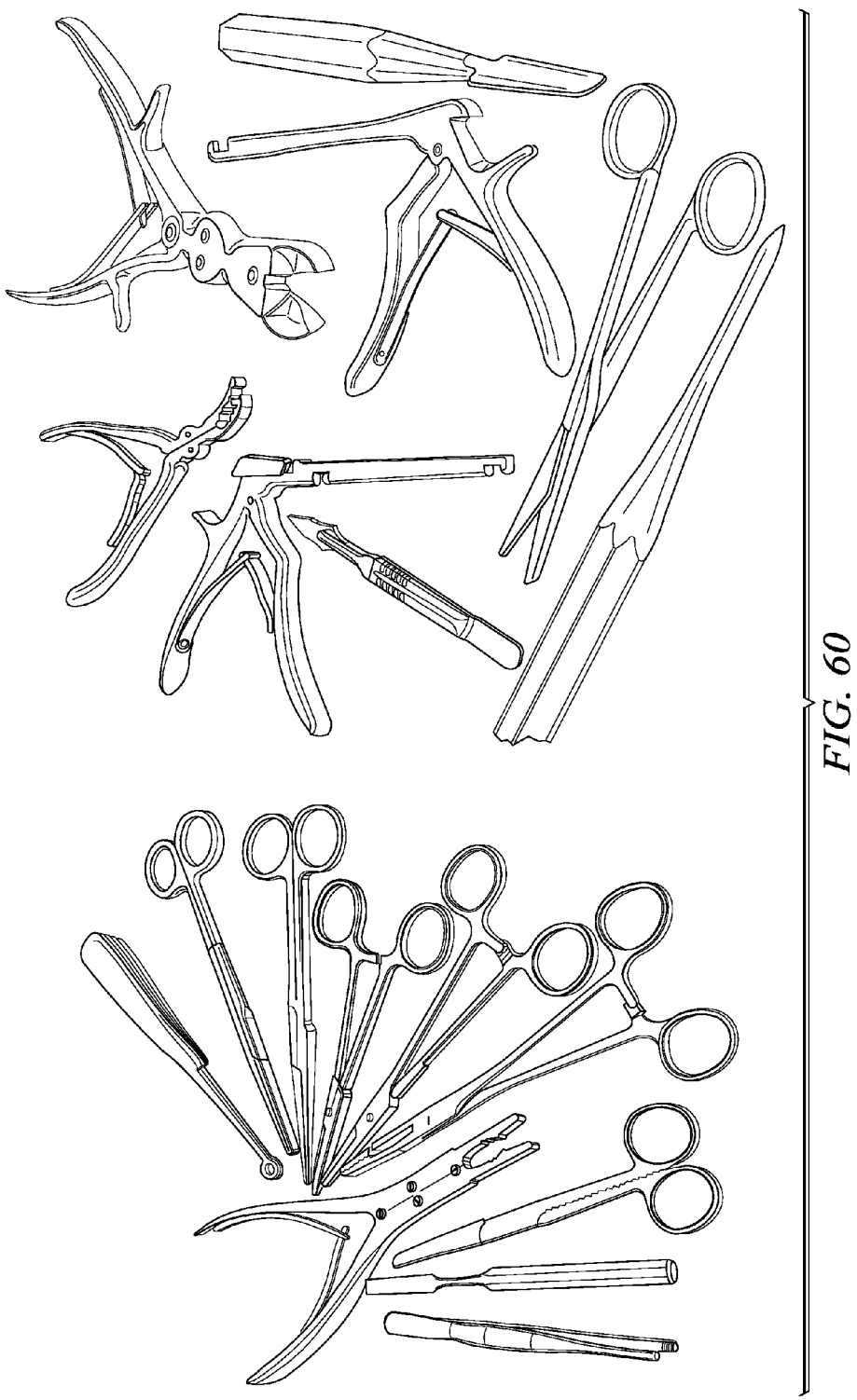
FIG. 60 illustrates pictorial representations of metal instruments (e.g., medical instruments) employable with the interrogation system of the present invention.

Turning now to FIG. 60, illustrated are pictorial representations of metal instruments (e.g., medical instruments) employable with the interrogation system of the present invention. It can be seen that the medical instruments are of various sizes and shapes, but in this case, made principally of metal.

Figure 61:
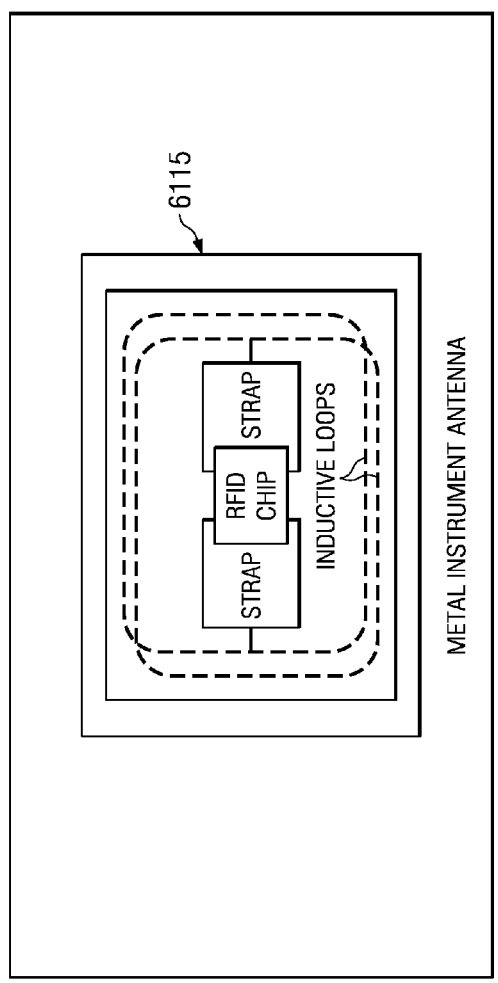
FIGS. 61 and 62 illustrate top and side views of an embodiment of a metal instrument including an RFID tag according to the principles of the present invention.
Figure 62:
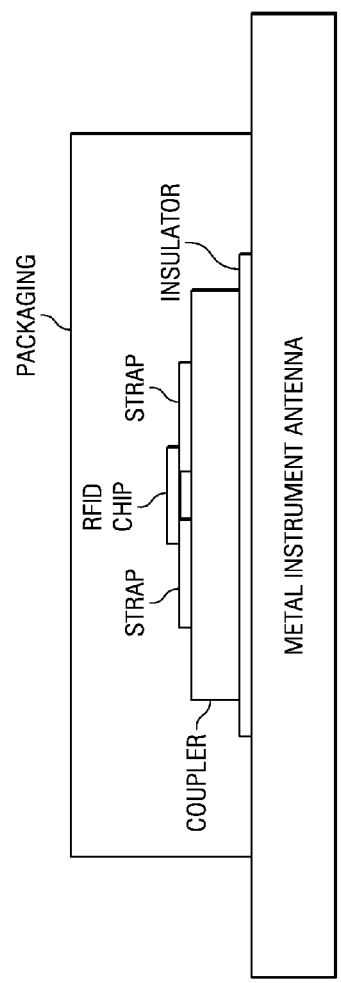

Turning now to FIGS. 61 and 62, illustrated are top and side views of an embodiment of a metal instrument including an RFID tag according to the principles of the present invention. The RFID tag includes an RFID chip mounted on a strap and placed on an insulator on to which are placed (by printing or other means) inductive loops, all of which are attached to a metal foundation of the metal instrument. The inductive loops may function as near field elements. The inductive loops may act as electromagnetic launching elements for launching energy into and from the metal foundation of the metal instrument so that the metal foundation itself becomes the antenna or a portion thereof. In those instances wherein the metal foundation is used as at least a portion of the antenna, a coupler, acting as an impedance transformer, may be necessary to more efficiently get the RFID energy into and out of the RFID chip. The subassembly including the coupler may also be bonded onto the surface of the metal foundation. A depression 6115 within the metal foundation may also be provided whereby the subassembly is placed and then covered with a suitable packaging such as a dielectric material and/or encapsulant for protection.

Figure 63:
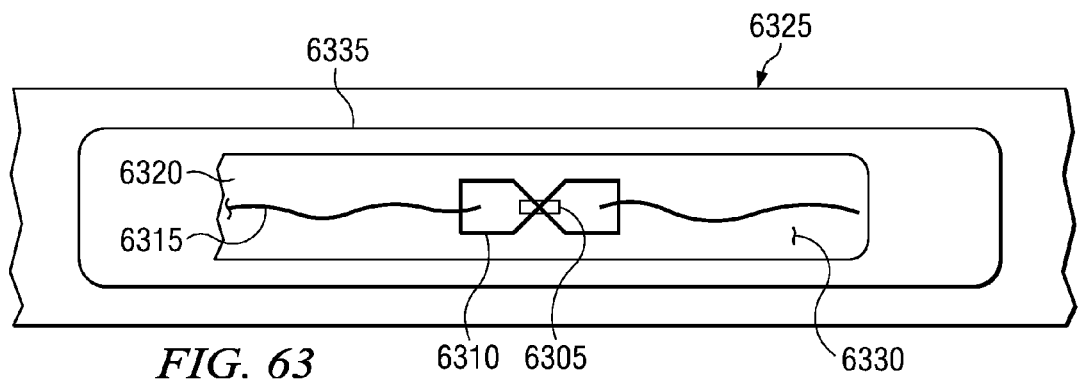
FIG. 63 illustrates a side view of an embodiment of a metal instrument including an RFID tag according to the principles of the present invention.

Turning now to FIG. 63, illustrated is a side view of an embodiment of a metal instrument including an RFID tag according to the principles of the present invention. The RFID tag includes an RFID chip 6305 and a strap 6310 along with an antenna 6315 mounted within a cavity 6320 hollowed out from a long portion of a metal foundation 6325 of the metal instrument. The RFID tag may be suspended within the cavity 6320 by an insulator or dielectric material 6330 so as to form a sufficient distance from the metal foundation 6325 of the metal instrument so as to allow proper electromagnetic field launch. The cavity 6320 is then filled with dielectric material or encapsulant (a portion of which is designated 6335) to protect the RFID tag and may also assist in providing a proper impedance match. In this embodiment, the cavity 6320 functions as a reflector of the radio frequency energy similar in manner to a reflector antenna as little or no physical connection exists between the antenna 6315 and the metal foundation 6325.

Thus, a metal instrument for use with an interrogator and an interrogation system has been introduced herein. In one aspect, the metal instrument (e.g., a medical instrument) includes a metal foundation, an RFID chip, and a coupler configured to couple the RFID chip to the metal foundation to allow at least a portion of the metal foundation to serve as an antenna thereby forming at least a portion of an RFID tag with the RFID chip. The coupler may be bonded to a surface of the metal foundation.

In other aspects, the metal instrument includes an insulator located between the coupler and the metal foundation, and a strap located between the RFID chip and the coupler. Additionally, the metal instrument also includes an inductive loop about the RFID chip located on the insulator coupled to the RFID chip. The metal instrument also includes a depression in the metal foundation for the RFID chip and the coupler. The metal instrument also includes an encapsulant configured to encapsulate the RFID chip and the coupler. Additionally, the RFID chip includes information associated with the metal instrument.

In another aspect, an interrogation system includes a metal instrument including a metal foundation, an RFID chip, and a coupler configured to couple the RFID chip to the metal foundation to allow at least a portion of the metal foundation to serve as an antenna thereby forming at least a portion of an RFID tag with the RFID chip. The interrogation system also includes a sensing subsystem configured to provide a signal having at least one of a metal signature representing a presence of the metal foundation and an RFID signature representing a presence of the RFID tag. The interrogation system also includes a control and processing subsystem configured to process the signal to discern a presence of at least one of the metal foundation and the RFID tag.

In another aspect, the metal instrument (e.g., a medical instrument) includes a metal foundation with a cavity (e.g., hollowed from a long portion of the metal foundation), an insulator within the cavity, and an RFID tag separated from the metal foundation within the cavity by the insulator. The cavity is configured to act as a reflector of radio frequency energy associated with the RFID tag.

In other aspects, the RFID tag includes an RFID chip and a strap. Also, the cavity is filled with an encapsulant to protect the RFID tag or to enhance an impedance match for the RFID tag. The RFID tag is separated from the metal foundation within the cavity by a distance to allow an electromagnetic field launch. Additionally, the RFID chip includes information associated with the metal instrument.

In another aspect, an interrogation system includes a metal instrument including a metal foundation with a cavity, an insulator within the cavity, and an RFID tag separated from the metal foundation within the cavity by the insulator. The cavity is configured to act as a reflector of radio frequency energy associated with the RFID tag. The interrogation system also includes a sensing subsystem configured to provide a signal having at least one of a metal signature representing a presence of the metal foundation and an RFID signature representing a presence of the RFID tag. The interrogation system also includes a control and processing subsystem configured to process the signal to discern a presence of at least one of the metal foundation and the RFID tag.

Considering surgical procedures, studies have shown that approximately 76 percent of all items unintentionally retained within a patient as the result of a procedure are categorized as surgical sponges. The surgical sponges are all too often left within the patient, even though the medical staff exercises extraordinary procedures to prevent this. Medical emergencies and time pressures provide a fertile environment for what is still a manual procedure.

Figure 64:
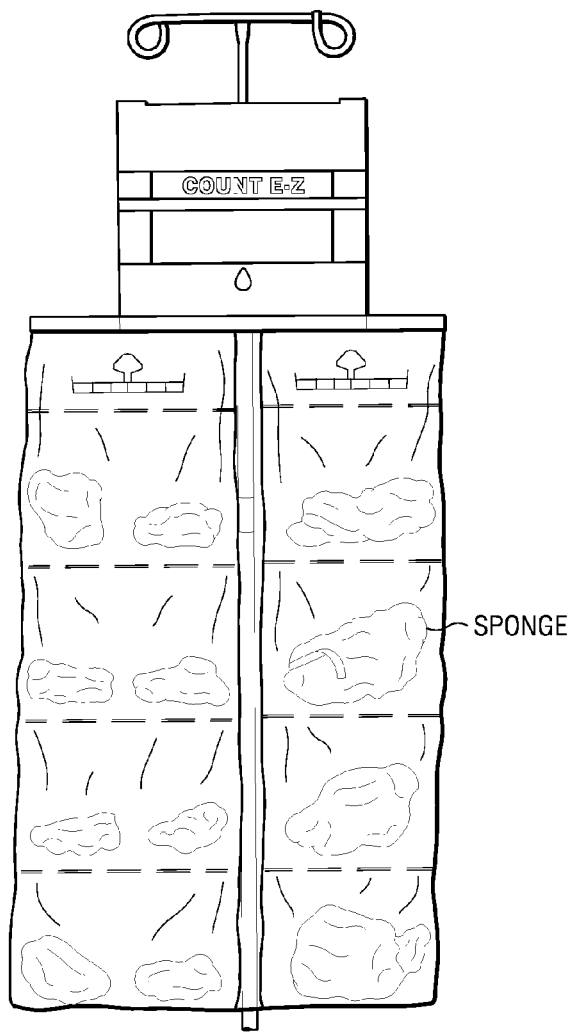
FIG. 64 illustrates a pictorial representation of an exemplary counting system for surgical sponges.

Turning now to FIG. 64, illustrated is a pictorial representation of an exemplary counting system for surgical sponges. The sponge counter system, essentially a plastic sheet with pockets and suspended on a pole, is used to separate and count sponges (one of which is designated "SPONGE"). These manual systems require active control of the individual(s) responsible for counting, and are prone to error as blood and fluid soaked sponges can easily be lumped together and therefore appear as a single sponge so that multiple sponges can erroneously be placed into a single pocket. Finding such an erroneously placed sponge and correcting the action can take considerable time as it is not known whether or not the sponge may still be retained within the patient. Additionally, even when found, the risk to the patient has been increased as the time when the surgical opening can be closed must be delayed until the count is correct. Not finding a sponge that has inadvertently been left in a patient during a surgical procedure is sufficiently common to have been given the clinical name of gossipyboma. Multiple cases exist within the literature of gossipyboma causing major suffering, irreparable damage to the health of the patient, and even including death.

Therefore, what is needed is an accurate enabling system that provides the means for surgical sponges to be automatically detectable prior to the procedure, during the procedure when they are intracorporeal, and post procedure when they are either soiled, or have never been used so that full accountability is always accurately maintained. In accordance therewith, a sponge according to the present invention includes an RFID tag, special encapsulation for the RFID tag, and a means to affix the RFID tag to the sponge. Additionally, the sponge may include a radiopaque object, special encapsulation for the object, and a means to affix the object to the sponge. The sponge may also include a designator (e.g., surface designation) as set forth herein.

A tagged sponge system is described that includes at least one surgical sponge, one encapsulated RFID tag, and the means to permanently affix the RFID tag to the sponge. The RFID tag provides the means by which the sponge is at all times detectable when used in conjunction with interrogators.

Figure 65:
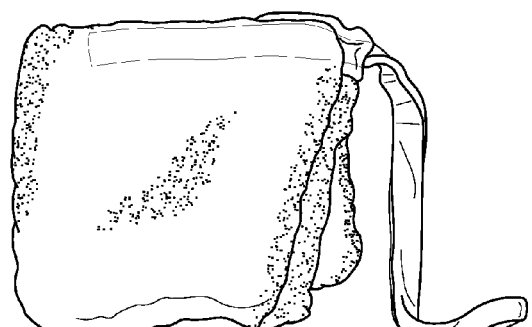
FIGS. 65 to 68 illustrate pictorial representations of several types of surgical sponges.

Turning now to FIGS. 65 to 68, illustrated are pictorial representations of several types of surgical sponges. These examples are not meant to be exhaustive, but only serve to show some of the various types and shapes consistent with a surgical sponge. The sponge of FIG. 65 is commonly referred to as a LAP sponge or a 4×4 including several layers of washed cotton sewn together and typically has a loop 6510 sewn into it. This loop 6510 is permeated with a radiopaque material, typically barium sulphate. The purpose of this radiopaque loop 6510 is so that a sponge inadvertently left within a patient can be discovered through an x-ray procedure. Should an x-ray procedure be necessary to find an errant sponge, the time to accomplish this is in the range of 15 to 45 minutes. As operating room time is in the range of $45 to $90 per minute, the expense of requiring such an operation can be considerable. Additionally, these impregnated loops 6510 are typically judged to be only about 80 percent effective as a detection mechanism, so even though great effort and expense is incurred, the results can still be unacceptable and even disastrous.

Figure 66:
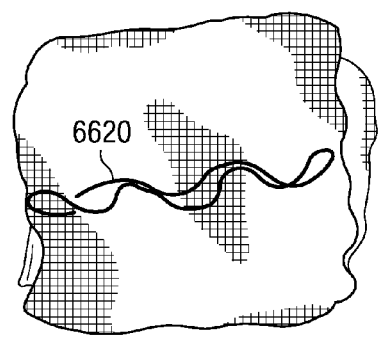

Turning now to FIG. 66, illustrated is another example of a surgical sponge, often referred to as a RAY-TEC. This sponge is approximately the same size as the LAP sponge (four inches square), but contains less cotton material. Additionally, radiopacity is accomplished here via impregnated threads 6620. Given that loop 6510 is only about 80 percent effective, the much smaller threads 6620 are therefore deemed to be less than 80 percent effective, once again indicating a significant problem.

Figure 67:
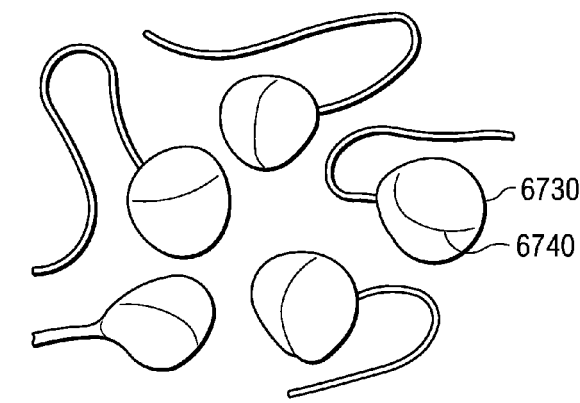

Turning now to FIG. 67, illustrated are examples of what are often called tonsil sponges 6730. These are spherical in shape and can be used to separate muscle tissues or organs and are typically 0.5 inches in diameter. When used in this manner they can be obstructed (i.e., hidden from view) by that same muscle tissue or organ. Radiopacity is achieved here by colored threads 6740, which once again are relatively sparse.

Figure 68:
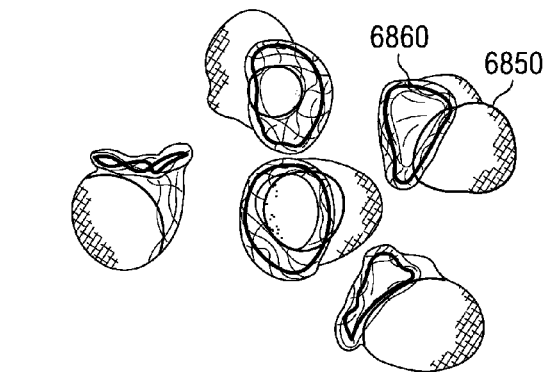

Turning now to FIG. 68, illustrated is another example of a spherical sponge 6850 referred to as a cherry dissector with radiopacity threads 6860 that are typically used in manners similar to the tonsil sponges. All these FIGUREs illustrate the need for detectability if left within the patient by the presence of radiopaque elements, but also show the inadequacy of current systems.

Figure 69:
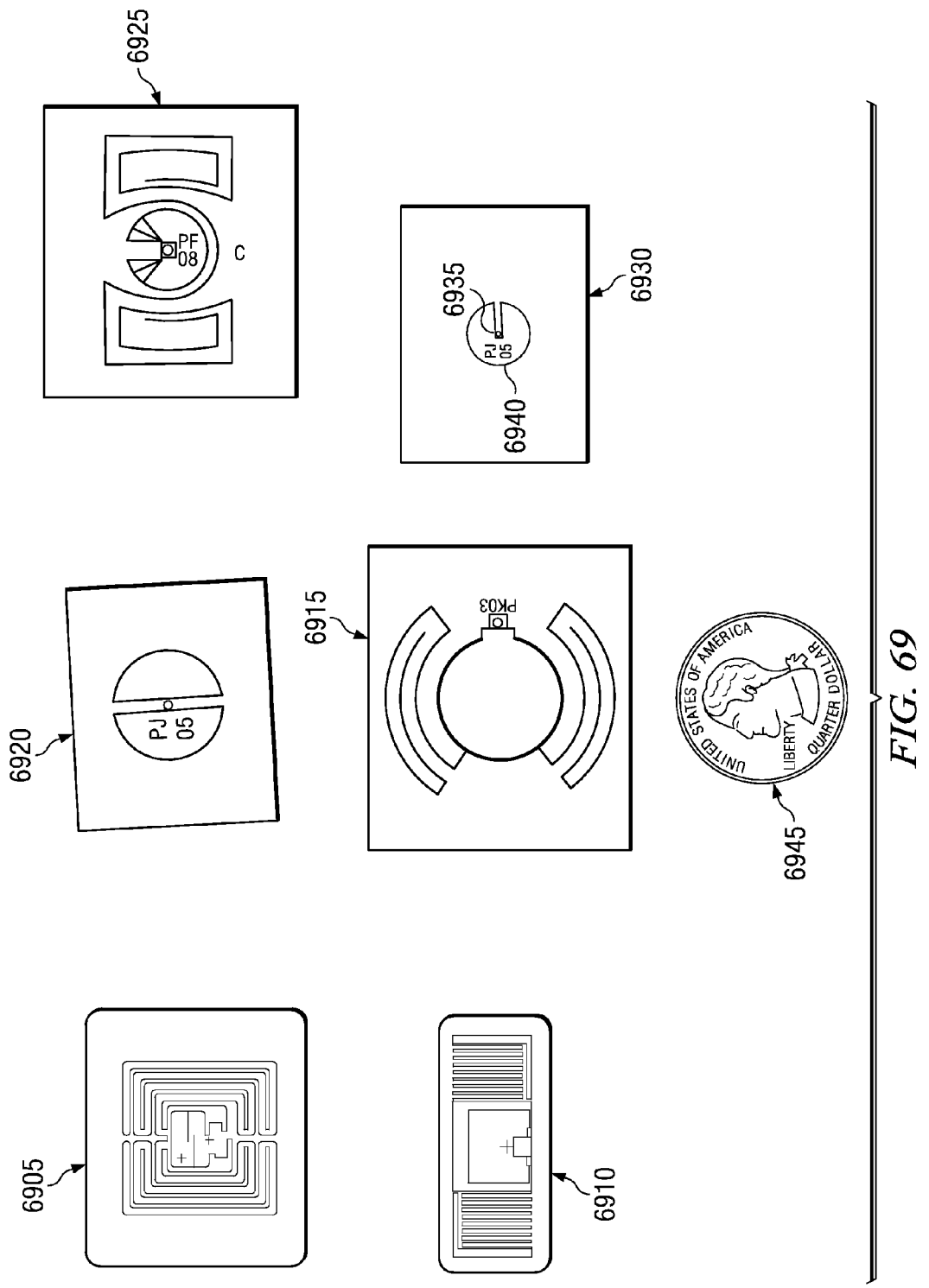
FIG. 69 illustrates pictorial representations of RFID tags.
Figure 70:
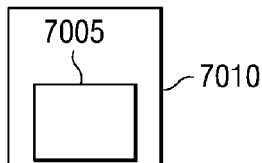
FIGS. 70 to 77 illustrate diagrams of embodiments of a sponge in accordance with the principles of the present invention.

Turning now to FIG. 69, illustrated are pictorial representations of RFID tags. These particular tags are UHF EPC Gen I and Gen II passive tags, but they are presented only as examples and other types of RFID tags may be employed as well. Both far field RFID tags 6905, 6910 and near field RFID tags 6920, 6930 are shown along with designs that encompass both near and far field RFID tag characteristics 6915, 6925. Specifically referring to RFID tag 6930, the structure includes a silicon chip 6935 connected to an antenna 6940. The chip 6935 and antenna 6940 along with a structure for holding same, often referred to as the inlay is what typically constitutes a passive RFID tag. A U.S. quarter 6945 is included as a reference for the size of these RFID tags.

Turning now to FIGS. 70 to 77, illustrated are diagrams of embodiments of a sponge in accordance with the principles of the present invention. A sponge is a reusable or consumable (or disposable) item that includes at least one layer of material and may be an absorbent surgical sponge. Beginning with FIG. 70, an encapsulant 7010 is added to protect an RFID tag 7005 from bodily fluids and other fluids used during a surgical procedure. The encapsulants used would typically comply with United States Pharmacopeia ("USP") Class IV, V, or VI standards or the standards as specified in ISO 10993 Biological Evaluation of Medical Devices to assure safety and biologic compatibility when within a patient. Many sources of such material exist and examples of companies manufacturing such materials are Master Bond, Dymax Corp., Loctite (Henkel Technologies), and Fisher-Moore. The RFID tag 7005 is completely encapsulated by the above referenced material. In some embodiments, encapsulant thickness may vary beyond that simply employed for RFID tag protection. Based on the type of RFID tag employed, near field or far field, the added thickness may be employed to launch the proper field mode.

Figure 71:
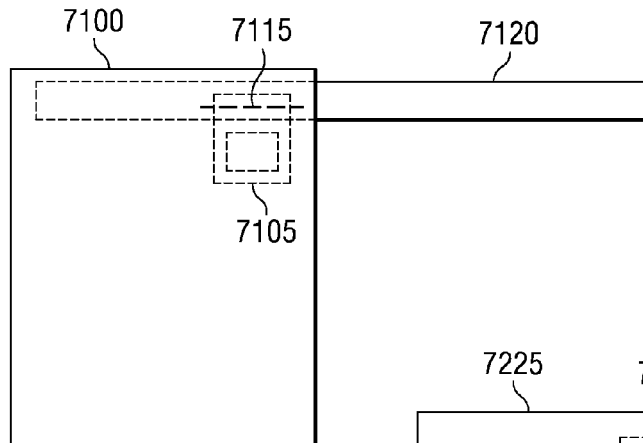
Figure 72:
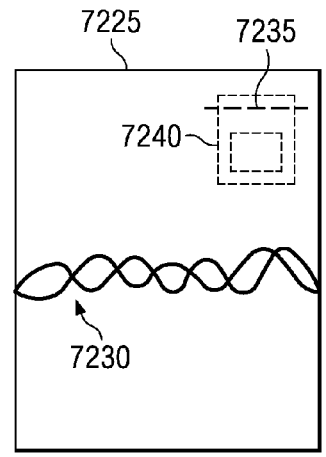

Turning now to FIG. 71, illustrated is a diagram of a LAP sponge 7100 with an encapsulated RFID tag 7105. In this embodiment, attachment occurs by sewing (designated by a seam 7115) the RFID tag 7105 onto the sponge 7100 in the same area as a radiopaque object (e.g., radiopaque loop) 7120 is attached. The sewing operation is performed on the encapsulant portion of the RFID tag 7105 thereby avoiding the actual antenna and chip areas. As illustrated, the sponge 7100 is formed from multiple layers of absorbent material and the RFID tag 7105 is located within an interior space of the sponge 7100. Additionally, FIG. 72 is an illustration of a RAY-TEC sponge 7225 with an RFID tag 7240 attached thereto. In this embodiment, attachment occurs by sewing (designated by a seam 7235) the RFID tag 7240 directly onto the sponge 7225 and in a region different from radiopaque threads 7230. As illustrated, the sponge 7225 is formed from multiple layers of absorbent material and the RFID tag 7240 is located within an interior space of the sponge 7225. Additionally, ends of the ends of the layers are bound and the interior space is formed therebetween. In both embodiments above, the RFID tag was sewn, but this invention comprehends embodiments where the RFID tag is affixed in any manner including bonded by an adhesive agent as well.

As mentioned above, since these sponges consist of multiple layers, the RFID tags are embedded among and within an interior space of the layers and may be affixed to an external layer of the sponge. Additionally, this invention comprehends an embodiment where the surface of the encapsulant consists of a specified roughness or texture so that it additionally adheres to the sponge by attaching to individual fibers in a manner similar to Velcro. Additionally, this invention comprehends embodiments wherein the RFID tag is embedded within, or attached directly to, for instance, the radiopaque loop 7120 of FIG. 71 and thereby attached to the sponge at the same time as the loop 7120 is so affixed.

Figure 73:
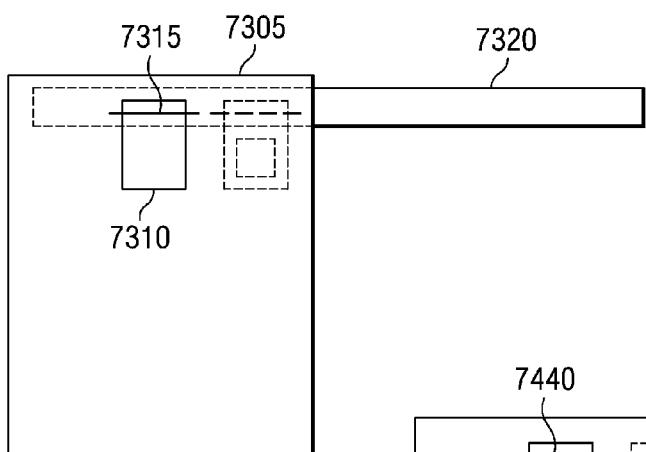
Figure 74:
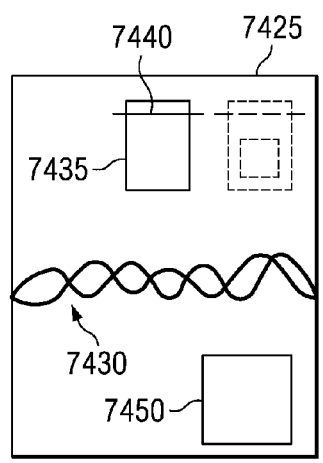

Turning now to FIG. 73, illustrated is an embodiment of an RFID tagged LAP sponge 7305 as described above in FIG. 71 with an encapsulated metal tag 7310 attached to the sponge 7305 by sewing (designated by a seam 7315). The purpose of the metal tag 7310 is to enhance the radiopacity of the LAP sponge 7305 forming a radiopaque element in addition to a radiopaque loop 7320. Additionally, FIG. 74 is an illustration of an embodiment of an RFID tagged RAY-TEC sponge 7425 as described above in FIG. 72 with an encapsulated metal tag 7435 attached to the sponge 7425 by sewing (designated by a seam 7440) also to enhance the radiopacity in addition to radiopaque threads 7430. In these embodiments, attachment occurs by sewing the metal tag directly onto the sponges and in a region proximately close to the areas where the RFID tags have been attached.

Additionally, this invention comprehends embodiments where the metal tag is not purely metal, but a metallic compound or some other radiopaque compound. Additionally, this invention comprehends embodiments wherein the metal tag is bonded by an adhesive agent as well. Additionally, since these sponges consist of multiple layers, this invention comprehends an embodiment wherein the metal tag is embedded among and within an interior space of the layers and may be sewn to an external layer of the sponge. Additionally, this invention comprehends an embodiment where the surface of the encapsulant consists of a specified roughness or texture so that it additionally adheres to the sponge by attaching to individual fibers in a manner similar to Velcro. Additionally, this invention comprehends embodiments where the RFID tag and the metal tag are encapsulated together into a single module. Additionally, this invention comprehends embodiments where the metal tag is embedded within, or attached to, a radiopaque loop 7120 of FIG. 71 and thereby attached to the sponge at the same time as the radiopaque loop 7120 is so affixed.

The sponges may also include a designator 7450 as indicated on the RAY-TEC sponge 7425 of FIG. 74. The designator 7450 may provide a surface designation by use of a highly visible indicator with a color, shape or pattern that is non standard (not currently used in the surgical or medical environment and clearly visible and readily identifiable) and, from a distance, clearly distinguishes the sponge 7425 as unique and appropriate. A unique surface color covering a significant percentage of the surface area of the sponge 7425 may be used (die, colored thread woven into the product, a sewn band of a unique color). A unique color preferably with a luminance having a high contrast ratio (e.g., greater than 10:1) may be beneficial. Also, preferably hydrophobic or liquiphobic colorant or material that maintains its color and differentiation under the majority of conditions expected in a healthcare setting would be beneficial. It should also be understood that an encapsulated RFID or metal tag may also be designated with a unique color, pattern or properties described above. The designator 7450 may also have other designations such as a bar code. The designator 7450 may also provide an indication beyond an RFID tag or metal tag that the sponge includes such an RFID tag or metal tag.

Figure 75:
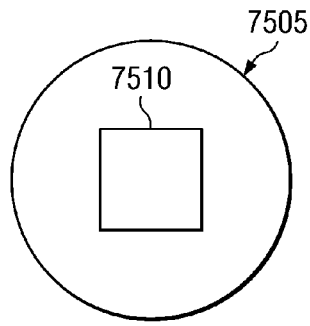
Figure 76:
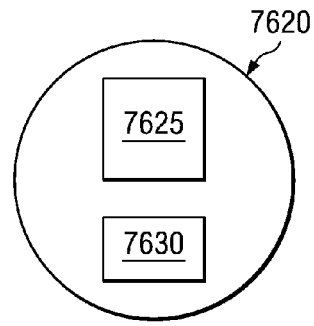
Figure 77:
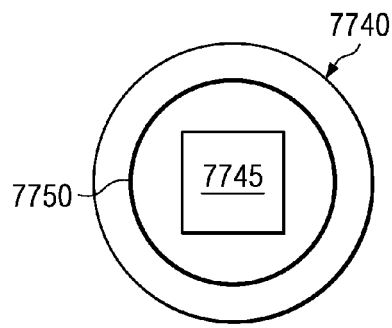

Turning now to FIG. 75, illustrated is a front view of an embodiment of a tagged tonsil sponge or cherry dissector sponge 7505 including an encapsulated RFID tag 7510 as described above. Turning now to FIG. 76, illustrated is a front view of an embodiment of a tagged tonsil sponge or cherry dissector sponge 7620 including an encapsulated RFID tag 7625 and an encapsulated radiopaque element 7630 as described above. Turning now to FIG. 77, illustrated is a front view of an embodiment of a tagged tonsil sponge or cherry dissector sponge 7740 including an encapsulated RFID tag 7745 and an encapsulated radiopaque element 7750 surrounding the RFID tag 7745. This invention comprehends embodiments of FIGS. 76 and 77 wherein the RFID tag and radiopaque element consist of a single module.

Thus, a sponge for use with an interrogator and an interrogation system has been introduced herein. In one aspect, the sponge (e.g., a LAP sponge or a RAY-TEC sponge) includes first and second layers of absorbent material that forms an interior space, and an RFID tag affixed (e.g., sewn or bonded by an adhesive agent) to the absorbent material within the interior space.

In other aspects, the sponge also includes a radiopaque object affixed to at least one of the first and second layers of the absorbent material and the RFID tag is affixed to the radiopaque object. Additionally, ends of the first and second layers are bound and the interior space is formed therebetween. The RFID tag includes an RFID chip and an antenna. The RFID tag is surrounded by an encapsulant and the RFID tag is affixed to the absorbent material through the encapsulant. The sponge also includes an encapsulated metal tag affixed through an encapsulant thereof to at least one of the first and second layers of the absorbent material. The metal tag may also be encapsulated with the RFID tag in a module affixed to at least one of the first and second layers of the absorbent material. The sponge may also include a designator affixed to at least one of the first and second layers of the absorbent material that is visible from outside of the interior space. The designator may be a liquiphobic designator with a luminance having a high contrast ratio.

In another aspect, the sponge includes at least one layer of material, an RFID tag affixed (e.g., sewn or bonded by an adhesive agent) to the material, and a designator (e.g., affixed to the material) that provides an indication beyond the RFID tag that the sponge includes the RFID tag. The designator may be a liquiphobic designator with a luminance having a high contrast ratio.

In other aspects, the sponge includes a radiopaque object affixed to the material and the RFID tag is affixed to the radiopaque object. The RFID tag is surrounded by an encapsulant and the RFID tag is affixed to the material through the encapsulant. The sponge includes an encapsulated metal tag affixed through an encapsulant thereof to the material. The metal tag may also be encapsulated with the RFID tag in a module affixed to the material.

In another aspect, an interrogation system includes a sponge including at least one layer of material, an RFID tag affixed to the material, a metal tag affixed to the material, and a designator that provides an indication beyond the RFID tag that the sponge includes the RFID tag. The interrogation system also includes a sensing subsystem configured to provide a signal having at least one of a metal signature representing a presence of the metal tag and an RFID signature representing a presence of the RFID tag. The interrogation system also includes a control and processing subsystem configured to process the signal to discern a presence of at least one of the metal tag and the RFID tag.

Figure 78:
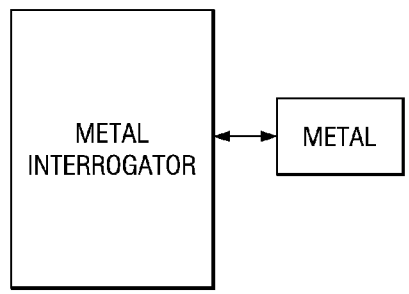
FIGS. 78 and 79 illustrate block diagrams of exemplary environments for application of a metal interrogator in accordance with the principles of the present invention.
Figure 79:
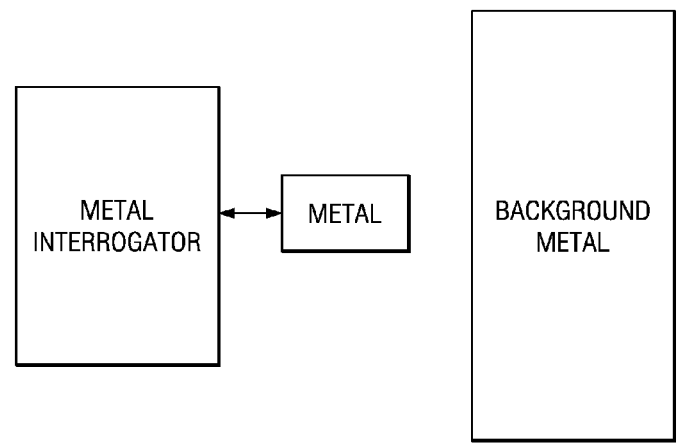

The present invention pertains to methods and apparatus for an improved metal detection assembly or metal interrogator including metal sensing systems and subsystems and the associated control and processing systems and subsystems. The design goals of devices of this class of equipment as shown in FIG. 78 may include not only high sensitivity, but also discrimination ability; for example, maximizing sensitivity to certain classes of target metals, while maximizing rejection of certain other classes or "background metal objects" as shown in FIG. 79.

Figure 80:
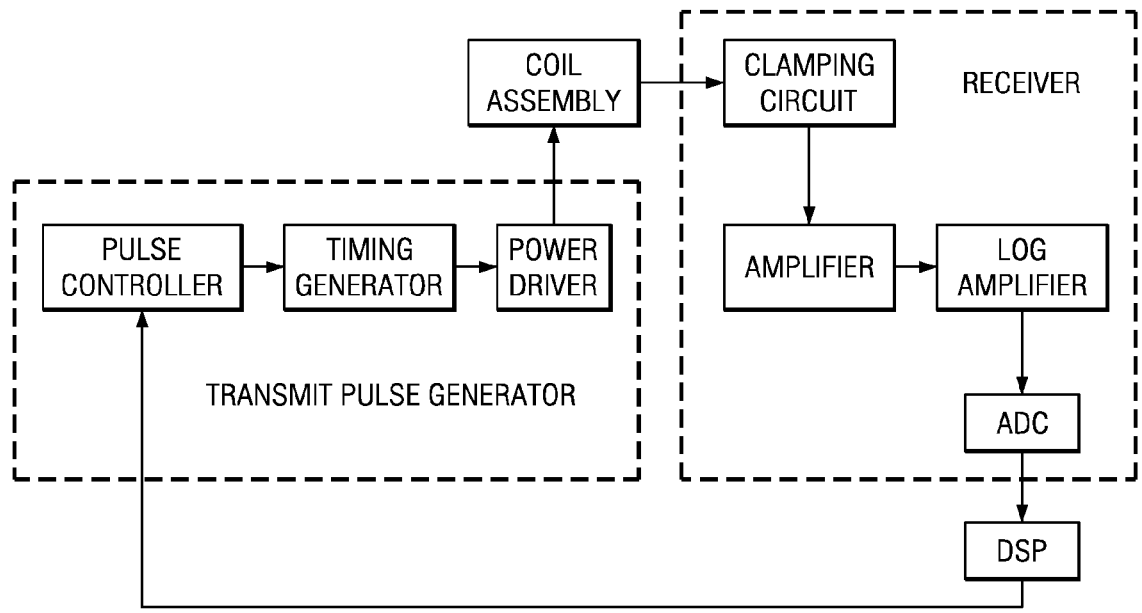
FIGS. 80 and 81 illustrate block diagrams of an embodiment of a metal interrogator constructed according to the principles of the present invention.
Figure 82:
FIGS. 82 to 89 illustrate diagrams of embodiments of antenna arrays employable with a metal interrogator constructed according to the principles of the present invention.
Figure 83:
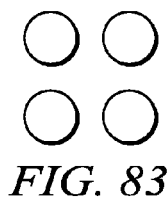
Figure 84:
Figure 85:
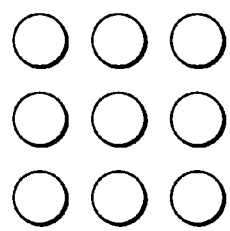
Figure 86:
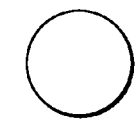
Figure 87:
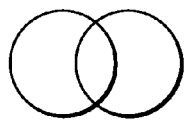
Figure 88:
Figure 89:
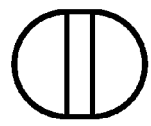

The metal interrogator is a refinement in what is known in the art as a pulse induction metal detection. An exemplary embodiment of the metal interrogator includes, among other things, an antenna array (also referred to as a coil assembly or coil(s), and antenna(s)), a metal sensing subsystem (including a transmit pulse generator with a pulse controller, timing generator and a power driver, and receiver) and a control and processing subsystem (including a digital signal processor "DSP"). The antenna array may be a single coil, or multiple coils with a system of relays connecting a selected coil to the driver and receiver. As described herein, an antenna array or coil assembly (designated "Coil Assy") in FIG. 80 is also referred to as a coil for the sake of brevity. FIGS. 82 to 85 illustrate examples of single and multiple antenna array configurations. The antenna arrays of FIGS. 82 to 84 illustrate the use of separate transmit and receive coils. As provided herein, reference will be made to embodiments that use an N-channel metal-oxide semiconductor field-effect transistor ("MOSFET") as the active element in the power driver. Of course, different types of active devices may also be used if the polarity of power supplies and if the direction/polarity of diodes are reversed, or multiple transistors may be used in parallel, or specific pulse shaping may also be desirable.

Figure 81:
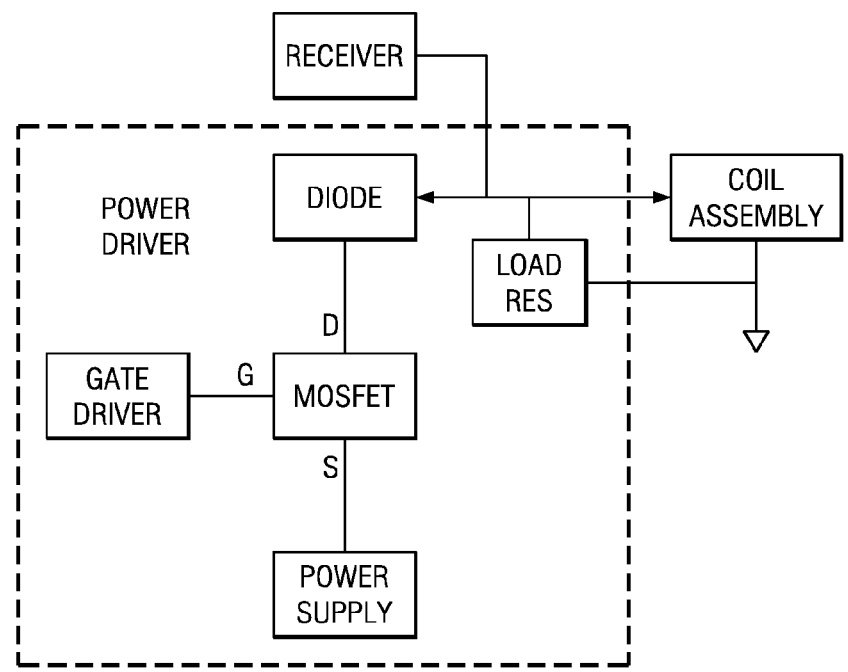

Turning now to FIGS. 80 and 81, illustrated are block diagrams of an embodiment of a metal interrogator constructed according to the principles of the present invention. The metal interrogator includes a control and processing subsystem (e.g., a digital signal processor ("DSP")) that through application of a timing generator of a transmit pulse generator feeds a control pulse of selected length to a gate terminal of a switch such as a MOSFET (e.g., an N-channel MOSFET) of the power driver causing the MOSFET, acting as a switching element, to turn ON for a short length of time. A direct current ("DC") power supply of the power driver with high short-term pulse current capability provides pulse energy to be fed into the magnetic field in the vicinity of the coil assembly. Its negative terminal is connected to a source terminal of the N-channel MOSFET, and its positive terminal is connected to one terminal of the coil assembly. The other terminal of the coil assembly goes to a drain terminal of the N-channel MOSFET, either directly or through a divorcing diode (designated "Diode") of the power driver to be described shortly. The energizing circuit within this embodiment is a loop of three elements including the power supply, coil assembly, and N-channel MOSFET, or correspondingly, a loop of four elements if the divorcing diode is in use, between the drain of the MOSFET and the coil assembly.

In this embodiment, the non-switched terminal of the coil assembly is referenced to ground potential, thereby making the power supply for the coil assembly a negative voltage supply, and also determines the form of pulse for the gate of the N-channel MOSFET. Of course, the coil assembly may not be specifically grounded. The potential for the power supply of the coil assembly may be, for example, −12 volts or −24 volts. A peak current reached by the end of the energizing pulse may reach, for example, 5, 10, 30 or 40 amps, and may be programmed through the choice of the pulse length and coil inductance. Exemplary pulse lengths are within the range of 5-40 microseconds.

The divorcing diode (again, designated "Diode") detects the effects of a response (e.g., decaying eddy currents) from the target metal object very early after the MOSFET switch turns OFF. The diode is selected using criteria of very fast reverse recovery time, high pulse current carrying capability, and low reverse capacitance. The cathode of the diode goes to the drain terminal of the N-channel MOSFET, and the anode goes to the coil assembly. While the MOSFET is turned ON, the diode is forward biased, and the large current building in the coil assembly passes therethrough. When the MOSFET switch turns OFF, the original current path through the MOSFET's conducting channel region becomes blocked, but because of the energy now stored in the magnetic field around the coil assembly, the current in the coil keeps flowing. At first, the current still flows mostly through the MOSFET. Even though the MOSFET is now an open switch, it has a parasitic capacitance on the order of hundreds of picofarads. The current goes to charge this capacitance, and as a result the drain voltage rises, perhaps to around +400 volts. Typically, a high voltage MOSFET is chosen to allow this, because higher voltages mean the energy comes out of the coil's magnetic field faster. The voltage may rise to the point where the MOSFET's internal limiting breakdown diode limits the energy, absorbing much of the coil's stored energy or, in another embodiment, an optional auxiliary circuit (not shown) may be added to limit the peak and absorb some of the energy, possibly even for re-use.

After a time, perhaps on the order of a microsecond, the energy in the coil's magnetic field and its terminal current reaches zero. This is an important transition toward the goal of making the applied pulse energy substantially disappear so that the tiny amounts of energy in the form of a response from the target metal object can be detected. However, the energy decay is not finished yet at this point, because now there are still substantial (on the order of 400 volts) parasitic and stray capacitances associated with the coil's switched terminal, and this means there is still stored energy. The circuit now takes on the characteristic of a capacitor-inductor resonator, capable of storing energy in resonant form, oscillating between magnetic energy in the coil assembly and electric field energy in the parasitic capacitance. A common solution is to have a load resistor placed across the coil terminals, chosen according to textbook formulas to approximate what is called "critical damping." An active circuit may be employed in place of the load resistor and actively control the speed at which energy dissipates.

An advantage of using the divorcing diode approach is that when the zero-current transition occurs, the diode becomes reverse-biased and therefore quickly becomes non-conductive. Instead of having on the order of 1000 picofarads of MOSFET drain capacitance connected to the coil assembly, the diode only presents on the order of 20 picofarads. The selection of the load resistor for the goal of critical damping should take this smaller value into account; and the result is a faster exponential decay of the residual energy. Furthermore, at the instant the diode begins to conduct, most of the residual energy in the system becomes isolated within the parasitic capacitance of the MOSFET, wherein it is trapped until the end of the detection cycle. The receiver includes a protective clamping circuit followed by an amplifier and, optionally, a logarithmic converter. The results are fed to an analog-to-digital converter ("ADC") and converted to sampled numerical waveforms for processing.

Figure 90:
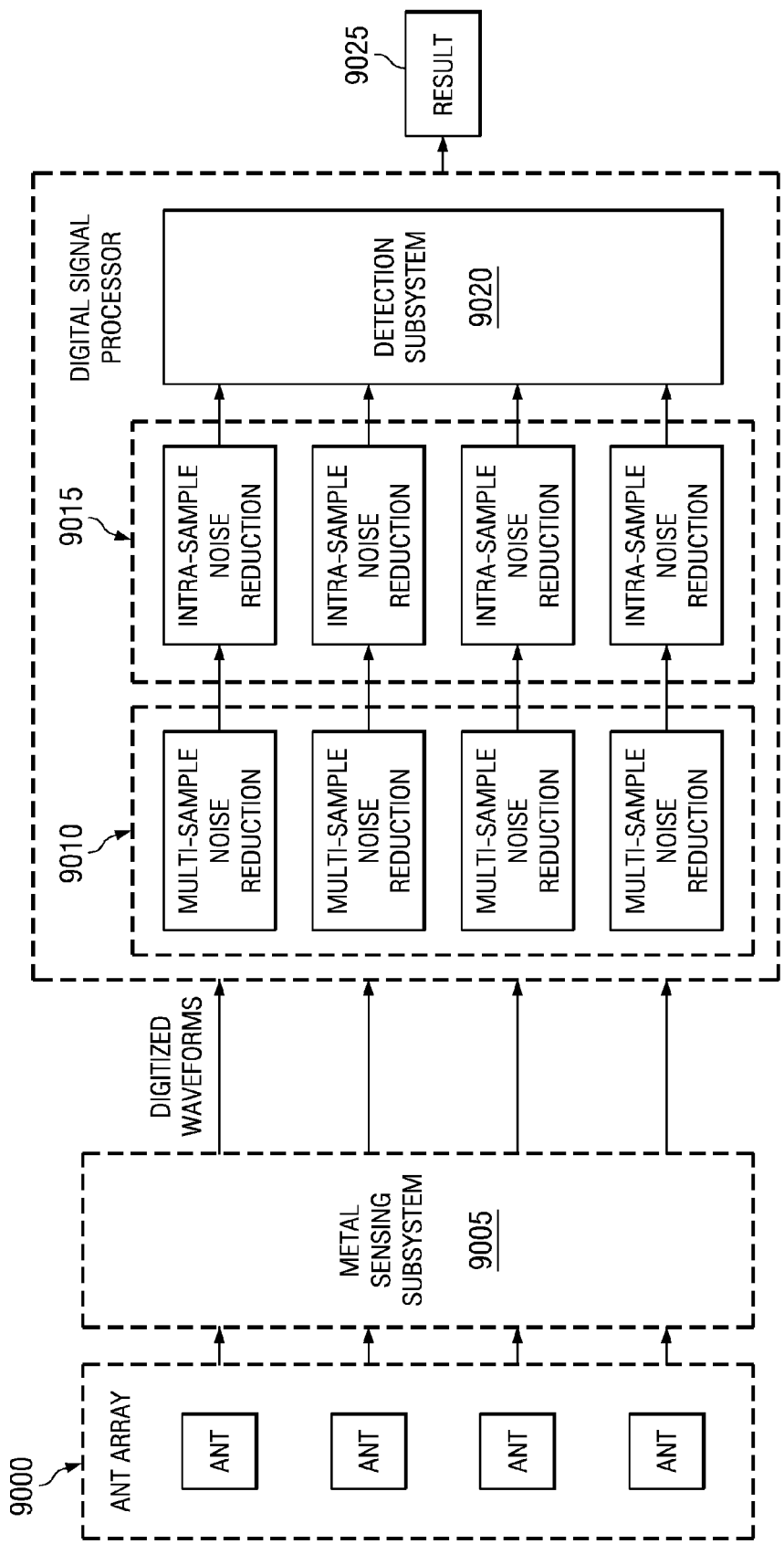
FIG. 90 illustrates a functional block diagram of portions of an embodiment of a metal interrogator constructed according to the principles of the present invention.

Turning now to FIG. 90, illustrated is a functional block diagram of portions of an embodiment of a metal interrogator constructed according to the principles of the present invention. An antenna array 9000 includes individual metal detection antennas (designated "Ant") coupled to a metal sensing subsystem 9005. As illustrated in FIG. 80, the metal sensing subsystem 9005 includes, in an exemplary embodiment, a transmit pulse generator and a receiver. Each of these antennas emit an electromagnetic pulse, then accept the decay characteristics of a response caused by the environment. The response is digitized within the metal sensing subsystem 9005, also referred to as a sample. Single or multiple samples may be taken from each antenna or a group of antennas. Two or more samples from a single antenna may be processed to reduce noise in a stage known as multi-sample noise reduction subsystems 9010. The resultant digital waveform from the multi-sample noise reduction subsystems 9010 may have further noise removal done by intra-sample noise reduction subsystems 9015. Other embodiments may reverse the order of these noise reduction subsystems, or perform only one stage or the other or no noise reduction. Then, a detection subsystem 9020 analyzes the resultant waveform or waveforms and produces a detection result 9025. In the illustrated embodiment, a digital signal processor including the multi-sample noise reduction subsystems 9010, the intra-sample noise reduction subsystems 9015 and the detection subsystem 9020 forms a control and processing subsystem for the metal interrogator.

Figure 91:
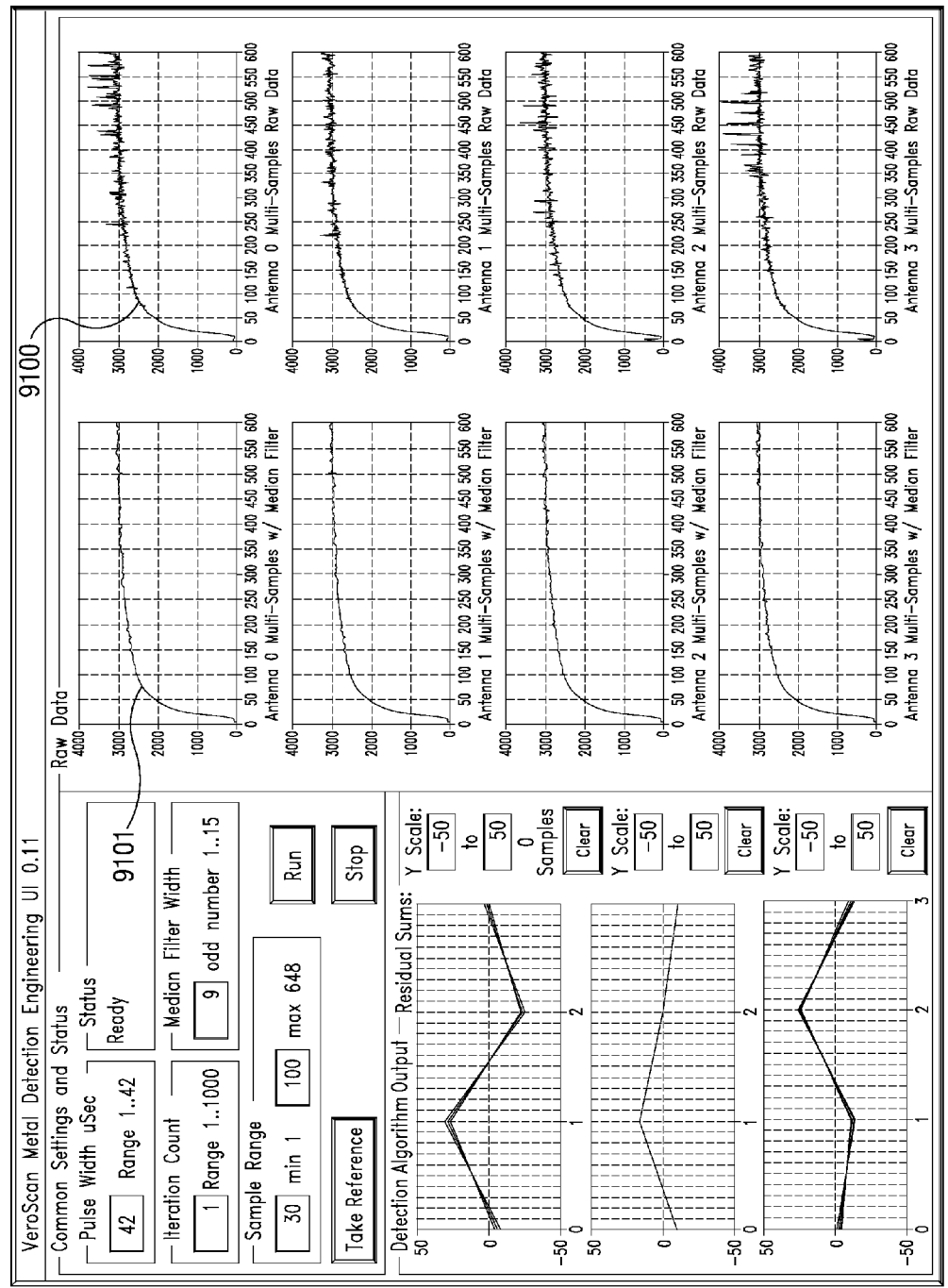
FIG. 91 illustrates digitized waveform diagrams demonstrating waveforms produced by a metal interrogator in accordance with the principles of the present invention.

Turning now to FIG. 91, illustrated are digitized waveform diagrams demonstrating waveforms produced by a metal interrogator in accordance with the principles of the present invention. Detection of a metal object within the area being scanned is accomplished by analysis of these waveforms. A waveform 9100 is illustrated from a single sampled response. Note the deviations from the smooth curve of the waveform, particularly in the latter (rightmost) parts of the sample. These irregularities are produced by environmental and uncorrected equipment noise and are collectively referred to as noise. The first stage of any metal detection process is the reduction of sample noise. Two general classes of noise reduction are used, namely, multi-sample noise reduction and intra-sample noise reduction.

Multi-sample noise reduction includes taking multiple samples from a single antenna within close temporal bounds. Since much of the noise seen in the waveform 9100 is random, noise should occur at different times within different samples, allowing multiple samples to be analyzed on a point by point basis to determine the invariant part of the sample. Illustrated in waveform 9101 is the result of deriving a sampled response with reduced noise from analysis of multiple sampled responses from the same antenna.

Figure 92:
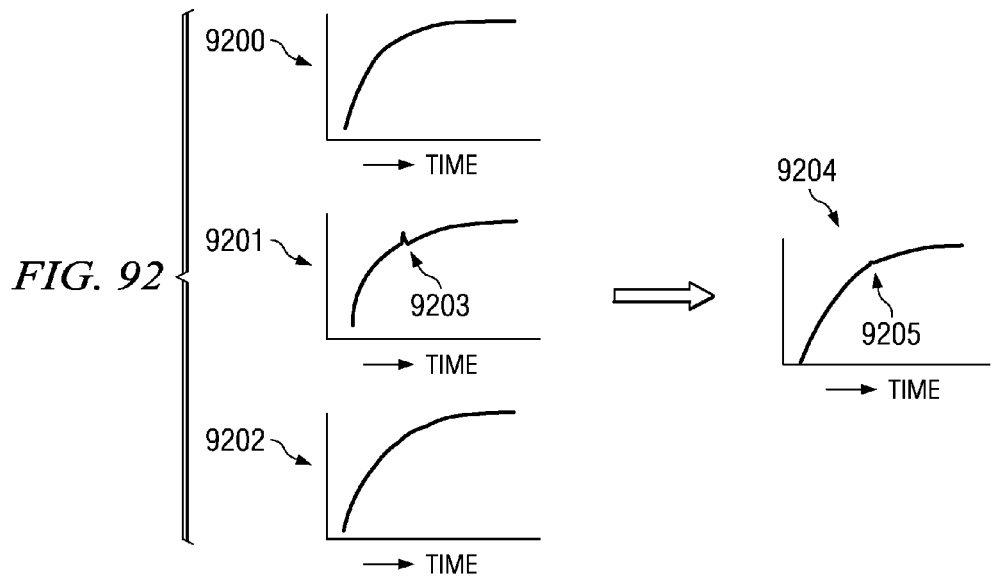
FIG. 92 illustrates exemplary waveform diagrams of three sampled responses taken from the same antenna within a short time interval in accordance with the principles of the present invention.

Turning now to FIG. 92, illustrated are exemplary waveforms diagrams 9200, 9201, 9202 of three sampled responses taken from the same antenna within a short time interval in accordance with the principles of the present invention. Note that waveform 9201 of the second sampled response has a noise spike 9203. Multi-sample noise reduction produces a waveform 9204 of the resultant single sampled response. Note that depending upon the noise reduction process used, the noise spike 9203 may be eliminated, or merely reduced as illustrated by noise spike 9205 in the waveform 9204 of the resultant single sampled response. Methods used to analyze multiple sampled responses from the same antenna to reduce noise include, but are not limited to, simple averaging, median filtering, and also performing an initial sort, and then discarding outliers via preprogrammed decisions. For example, this can be done assuming uniform, Gaussian, Cauchy, or other distributions. The selection of filtering method is driven by a need to reduce the number of samples to achieve a given reduction in noise. A person skilled in the art can derive other methods of noise reduction using multiple redundant sampled responses.

Figure 93:
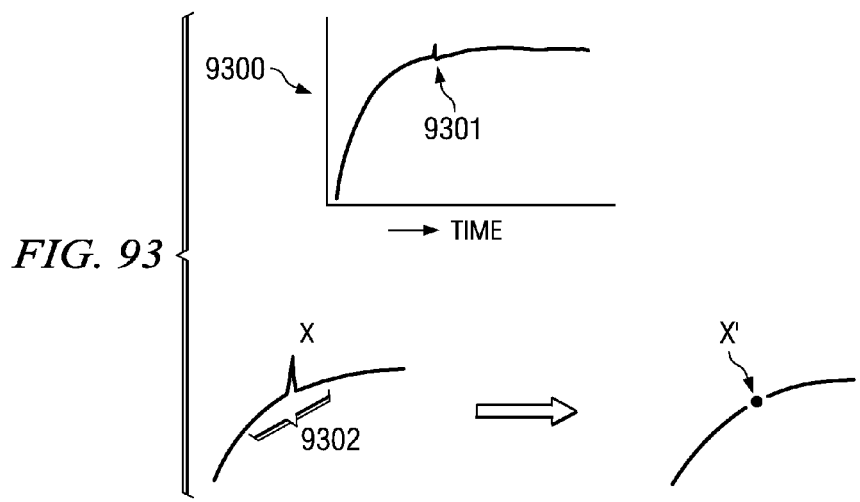
FIG. 93 illustrates waveform diagrams of intra-sample noise reduction that relies upon the fact that the resultant waveform from an induction pulse is an exponential curve in accordance with the principles of the present invention.

Turning now to FIG. 93, illustrated are waveform diagrams of intra-sample noise reduction that relies upon the fact that the resultant waveform from an induction pulse is an exponential curve in accordance with the principles of the present invention as exemplified in waveform 9300. Short duration random and non-random noise appears to be a spike 9301 on this otherwise smooth curve. Noise reduction methods that take advantage of the smoothness of the curve may be used here. These methods involve examining a "window" 9302 or range of adjacent data points on the curve (usually a small, odd number such as three or five) centered on a specific point X. These processes generate a new, reduced noise curve by setting point X' in the new curve to be a "reasonable" value given examination of the points adjacent to X. Thus, if a noise spike occurred at point X, the points immediately before and after X will probably be non-noise points, and the value of X can be inferred from these points. Typically, this is done by setting X to the average or median of the values of all points in the examination window 9302, but other methods exist and are obvious to one skilled in the art. A side-effect of this type of analysis is a shifting or delaying of the resultant sample, but this may be accounted for in the analysis system. Choice of window size is determined by anticipated noise spike duration (tends to drive the filter window wider) versus processing time (tends to drive the window narrower).

Detection systems take N noise-reduced sampled responses, where N is the number of distinct metal detection antennas, and produce a result that indicates the probability of a metal object of interest being near a particular antenna or antennas. This result may be combined with prior results via various methods as a further type of noise reduction. Three detection methods known as the residual method, the slope-differential method, and the curve crossing detection method may be employed without limitation.

Figure 94:
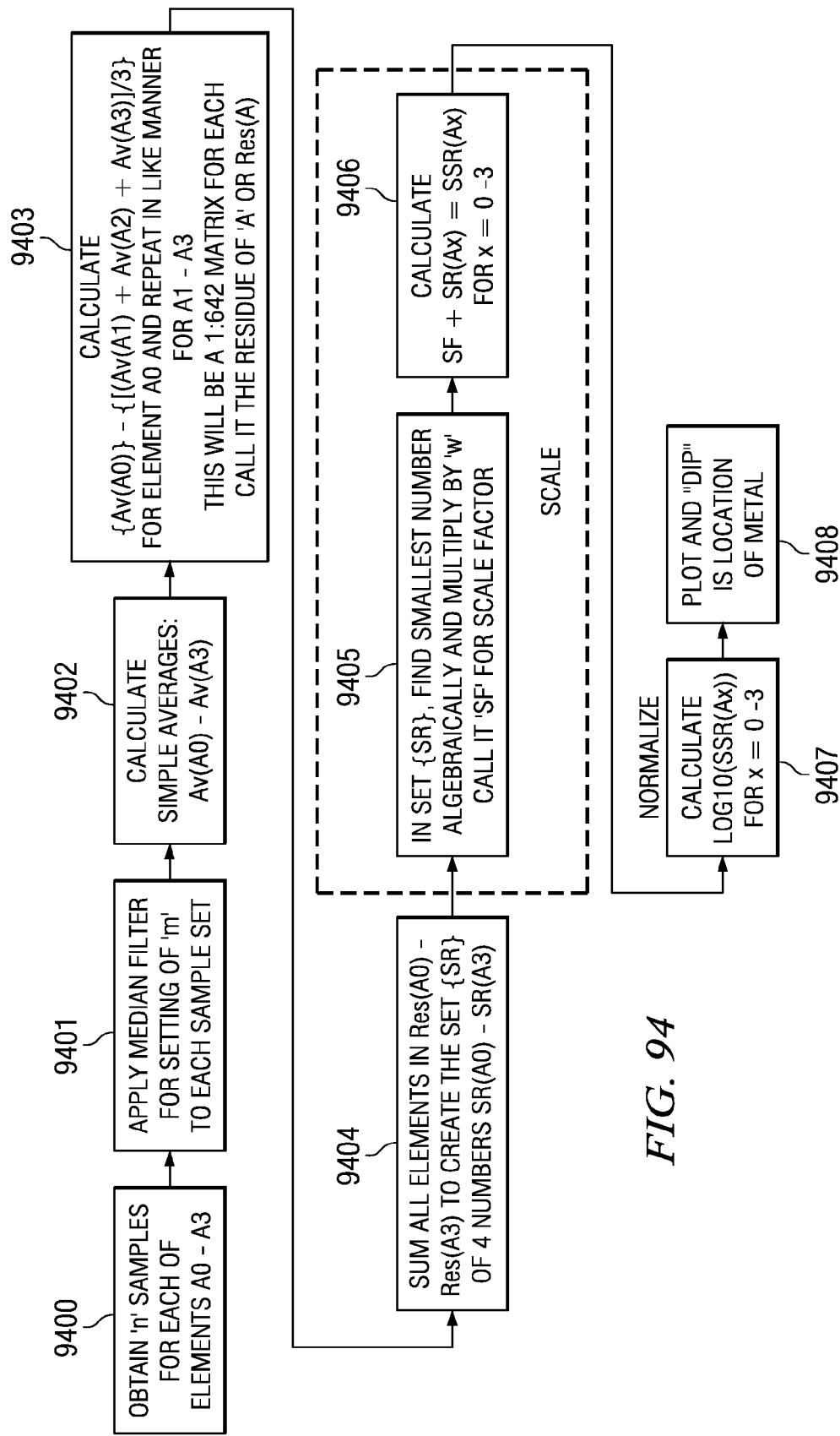
FIGS. 94 and 95 illustrate flow diagrams of embodiments of a residual method metal detection process for a metal interrogator in accordance with the principles of the present invention.
Figure 95:
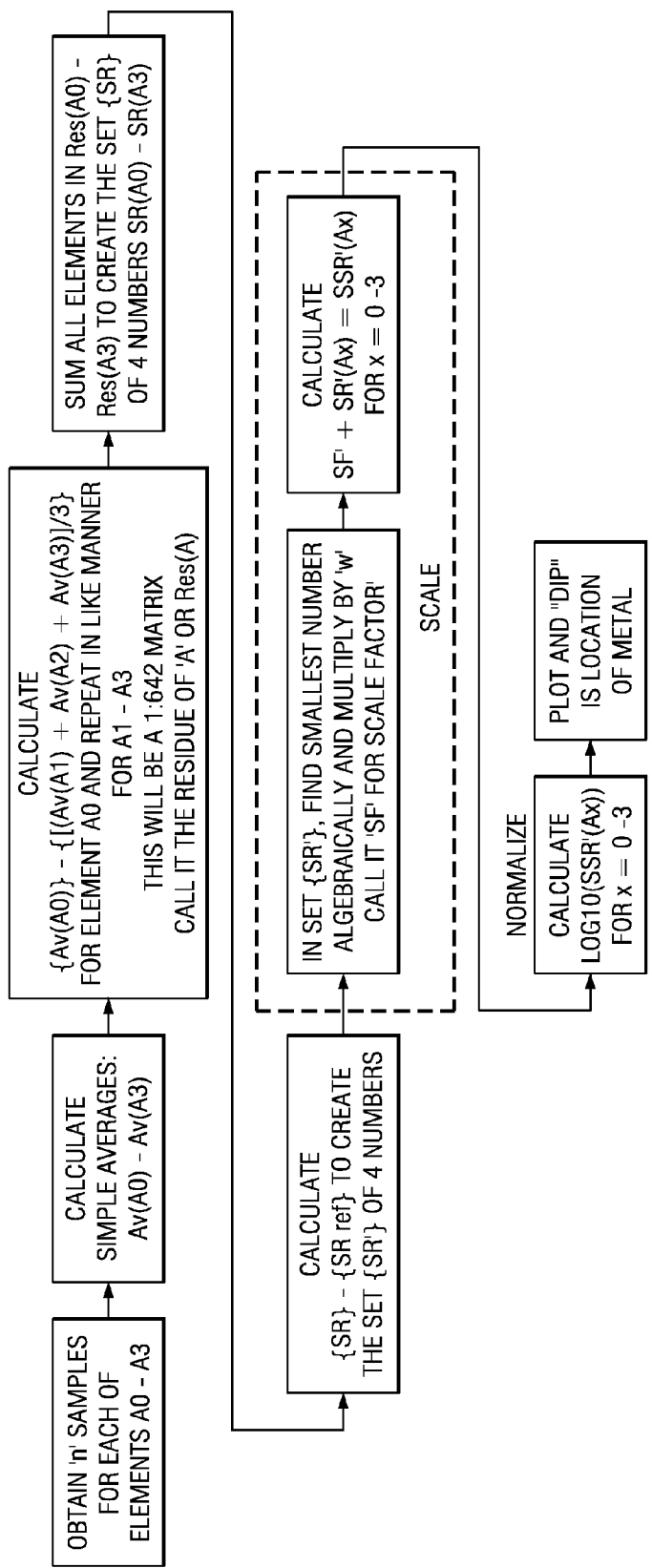

Turning now to FIGS. 94 and 95, illustrated are flow diagrams of embodiments of a residual method metal detection process for a metal interrogator in accordance with the principles of the present invention. The process of FIG. 94 is illustrated without using a reference and the process of FIG. 95 is illustrated using a reference. The discussion that follows describes the metal detection process in accordance without using a reference as illustrated in FIG. 94. In a step 9400, sampled responses are collected via an antenna array and metal sensing subsystem and, in a step 9401, noise reduction is performed on the sampled responses as discussed previously. In a step 9402, a control and processing system of the metal interrogator computes a "background" ambient signal level for each antenna by averaging the sampled responses for all antennas, preferably without the current antenna. This background ambient signal level is consistent on a pulse by pulse duration. The changes in this signal are typically larger than the variation in the response due to the presence of the target metal object. As a result, it may be advantageous to estimate the background ambient signal level on a pulse by pulse basis. This background ambient signal level is then subtracted point by point from the antenna's current sample.

Thus, the residual for antenna 0 in a four antenna array would be the difference between the antenna's sample and the average of the samples from antennas 1, 2 and 3. This effectively removes any signal common to all other antennas, thereby tending to reduce the effect of metal objects common to all antennas such as an operating room table. In a step 9403, the control and processing subsystem determines the area under the curve for each antenna's residual level. Since the presence of a metal object in an antenna's field reduces the initial portions of the curve, the integral of the curve is lower. In steps 9404, 9405 and 9406, the control and processing subsystem normalizes the integral values so that the lowest value is set to zero and, in a step 9407, the control and processing subsystem converts the values to a logarithmic scale to facilitate evaluation. In a step 9408, the control and processing subsystem detects the metal object by selecting the lowest of the integral values.

Figure 96:
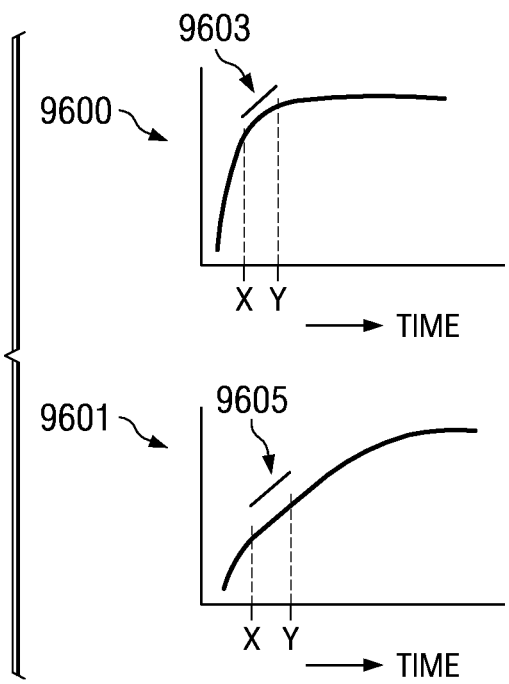
FIG. 96 illustrates waveform diagrams of sampled responses from two antennas, which are digitized and sampled, according to the principles of the present invention.

Turning now to FIG. 96, illustrated are waveform diagrams 9600, 9601 of sampled responses from two antennas, which are digitized and sampled, according to the principles of the present invention. Slope-differential analysis includes measuring the slope between two points X and Y, and comparing the resultant slopes 9603, 9605. Since the presence of a metal object in an antenna's scan field causes a resultant waveform with a flatter early (leftmost) portion, the presence of a metal object may be inferred from a lower slope. The choice of values of X and Y and the consequent slope location and slope length may be statically or dynamically altered within the scope of the present invention.

Figure 97:
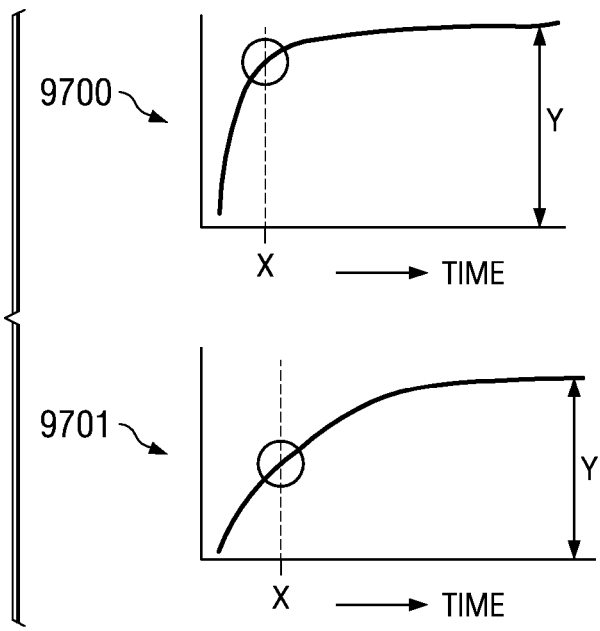
FIG. 97 illustrates waveform diagrams for sampled responses from two different metal detection antennas in accordance with the principles of the present invention.

Turning now to FIG. 97, illustrated are waveform diagrams 9700, 9701 for sampled responses from two different metal detection antennas in accordance with the principles of the present invention. A metal object is within the detection range of the antenna associated with the sampled response shown in waveform 9701, while the antenna associated with sampled response shown in the waveform 9700 has no metal object within range. Note the curve in waveform 9701 shows a lower amplitude than that of waveform 9700 during the earlier (leftmost) time interval, but shows a similar amplitude at a point late Y for the waveforms 9700, 9701, respectively. The curve crossing detection method determines the amplitude of the curve at a point X. Sampled responses with a lower amplitude at point X than sampled responses from other antennas may be inferred to have a metal object within detection range. Since the steady-state or rightmost portions of the waveforms 9700, 9701 are unaffected by metal objects, these may be used to dynamically determine the appropriate value of X as a self-calibration method. This logic may also be reversed, in which the value of X for a specific Y value is determined, where Y may be based upon a percentage of the final or rightmost parts of the curve. The full curve-crossing detection method may also contain logic to compensate for non-identical behavior among antennas and the presence of large metal objects (such as an operating table) within the scan field of all antennas. Additional exemplary antenna arrays shown in FIGS. 86 to 89 illustrate some of the various geometric structures that may be employed to enhance detection. The metal interrogator comprehends the use of multiple antenna arrays not shown in these FIGS.

Note that the detection processes described herein are illustrative and may be enhanced or modified by one skilled in the art. Such modifications may include, but are not restricted to, addition of calibration values to counteract differences in antenna characteristics, addition of calibration values used to define empty space or the lack of metal objects within the scan field, addition of logic to infer metal object location, size, orientation or composition, addition of logic to determine spatial placement of a metal object within a larger scan area (such as a surgical patient), changes to excitation pulse width or amplitude, and permutations of antenna sequencing, sample temporal spacing and sample sequencing.

Thus, a metal interrogator for use with an interrogation system, and a method of operating the same has been introduced herein. In one aspect, the interrogator includes an antenna array having coils (e.g., a plurality of overlapping coils) that define multiple areas, and a metal sensing subsystem configured to transmit a pulse to each coil of the antenna array and receive a response (e.g., a decaying eddy current response) therefrom. The interrogator also includes a control and processing subsystem configured to estimate and subtract a background signal level from the response from each coil and provide a residual therefrom, thereby discerning a presence of a metal object in at least one of the multiple areas. The background signal level may include a background metal object proximate the metal object.

In other aspects, the metal sensing subsystem includes a transmit pulse generator including a pulse controller, a timing generator and a power driver. The transmit pulse generator is configured to transmit the pulse. The metal sensing subsystem also includes a receiver including a clamping circuit, amplifier and analog to digital converter. The receiver is configured to receive the response and provide a sampled response to the control and processing subsystem. The control and processing subsystem (e.g., a digital signal processor) is configured to estimate and subtract the background signal level from the sampled response.

In still other aspects, the control and processing subsystem includes a multi-sample noise reduction subsystem, an intra-sample noise reduction subsystem and a detection subsystem. The control and processing subsystem is configured to estimate the background signal level for each coil by averaging the responses for the coils. The control and processing subsystem is configured to subtract the background signal level point by point from the response. The control and processing subsystem is also configured to normalize an integral value of the residual. The control and processing subsystem is also configured to normalize an integral value of the residual for each coil and select a lowest value therefrom to discern the presence of the metal object.

Exemplary embodiments of the present invention have been illustrated with reference to specific electronic components. Those skilled in the art are aware, however, that components may be substituted (not necessarily with components of the same type) to create desired conditions or accomplish desired results. For instance, multiple components may be substituted for a single component and vice-versa. The principles of the present invention may be applied to a wide variety of applications to identify and detect objects. For instance, in a medical environment, instrument kits including a plurality of objects can be scanned in situ to log the contents thereof into an interrogator, and subsequently the instrument kit can be scanned by the interrogator to verify the contents, the integrity of the contents (including expiration dates for time sensitive objects) and the like. The increased sensitivity of the interrogator according to the principles of the present invention opens up many new opportunities (e.g., supply chain management in consumer related retail applications, security applications, etc.) for the interrogation system disclosed herein.

Also, although the present invention and its advantages have been described in detail, it should be understood that various changes, substitutions and alterations can be made herein without departing from the spirit and scope of the invention as defined by the appended claims. For example, many of the processes discussed above can be implemented in different methodologies and replaced by other processes, or a combination thereof, to form the devices providing reduced on-resistance, gate drive energy, and costs as described herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An interrogation system, comprising:
   a first fixed interrogator, located at a first station, configured to detect an object at a first time;
   a second fixed interrogator, located at a second station, configured to detect said object at a second time;
   a mobile interrogator, located at a third station, configured to detect said object at a third time as said mobile interrogator moves with respect to said object; and
   a base command unit configured to receive signals from said first and second fixed interrogators and said mobile interrogator to track a location of said object.

2. The interrogation system as recited in claim 1 wherein said object is selected from the group consisting of:
   a radio frequency identification object,
   a radio frequency object,
   a metal object,
   a bar coded object,
   an microelectromechanical systems object,
   an optical recognition object, and
   a dot-peening object.

3. The interrogation system as recited in claim 1 wherein said first and second fixed interrogators and said mobile interrogator employ antennas selected from the group consisting of:
   far field antennas,
   near field antennas,
   near field antenna arrays,
   ring antennas, and
   bi-static antennas.

4. The interrogation system as recited in claim 1 wherein said base command unit is configured to track a location of said object in real time.

5. The interrogation system as recited in claim 1 wherein said first and second fixed interrogators and said mobile interrogator are radio frequency identification interrogators and said object is a radio frequency identification object, said interrogation system further comprising another interrogator configured to detect a different object and said base command unit being configured to receive signals from said another interrogator to track a location of said different object.

6. The interrogation system as recited in claim 1 wherein said first, second and third locations are located in an operating room selected from the group consisting of:
- a back table,
- a soiled consumable and instrument station,
- a dirty basin station, and
- an operating station.

7. The interrogation system as recited in claim 1 wherein said mobile interrogator is an integrated radio frequency identification and other interrogator configured to detect a radio frequency identification object and a different object, said base command unit configured to receive signals from said mobile interrogator to track a location of said radio frequency identification and different objects.

8. The interrogation system as recited in claim 1 further comprising a charger for said mobile interrogator.

9. The interrogation system as recited in claim 1 wherein said base command unit communicates with another computer system.

10. The interrogation system as recited in claim 1 wherein said base command unit is coupleable to a display to show a location of said object.

11. The interrogation system as recited in claim 1 wherein said base command unit is a laptop computer.

12. The interrogation system as recited in claim 1 wherein said base command unit, comprises:
- an input/output device,
- device management module,
- an operating system,
- a processor,
- a memory,
- an external computer system interface,
- a power management module, and
- a remote communications module.

13. The interrogation system as recited in claim 1 wherein ones of said first and second fixed interrogators and said mobile interrogator, comprise:
- a device management module,
- a sensing subsystem,
- a power management module,
- a remote communications module, and
- a user interface module.

14. The interrogation system as recited in claim 1 wherein said object is a radio frequency identification object in the form of a sponge with a radio frequency identification tag.

15. The interrogation system as recited in claim 1 wherein said object is a radio frequency identification object and ones of said first and second fixed interrogators and said mobile interrogator generate radio frequency energy in accordance with a radio frequency identification sensing subsystem and a radio frequency power amplifier to detect said radio frequency identification object.

16. A method of operating an interrogation system, comprising:
- detecting an object at a first station with a first fixed interrogator at a first time;
- detecting said object at a second location with a second fixed interrogator at a second time;
- detecting said object at a third location with a mobile interrogator at a third time as said mobile interrogator moves with respect to said object;
- receiving signals from said first and second fixed interrogators and said mobile interrogator at a base command unit; and
- tracking a location of said object with said base command unit.

17. The method as recited in claim 16 wherein said object is selected from the group consisting of:
- a radio frequency identification object,
- radio frequency object,
- a metal object,
- a bar coded object,
- a microelectromechanical systems object,
- an optical recognition object, and
- a dot-peening object.

18. The method as recited in claim 16 wherein said first and second fixed interrogators and said mobile interrogator employ antennas selected from the group consisting of:
- far field antennas,
- near field antennas,
- near field antenna arrays,
- ring antennas, and
- bi-static antennas.

19. The method as recited in claim 16 wherein said first and second fixed interrogators and said mobile interrogator are radio frequency identification interrogators and said object is a radio frequency identification object, said method further comprising detecting a different object and said base command unit being configured to receive signals to track a location of said different object.

20. The method as recited in claim 16, further comprising:
- displaying a location of said object; and
- communicating with another computer system.

* * * * *